United States Patent
Ulrich et al.

(10) Patent No.: US 11,414,461 B2
(45) Date of Patent: Aug. 16, 2022

(54) METHOD AND COMPOSITION FOR DETERMINING SPECIFIC ANTIBODY RESPONSES TO SPECIES OF FILOVIRUS

(71) Applicant: **THE GOVERNMENT OF THE UNITED ST

A

Slide Barcode

| | BDBV | TAFV | RESTV | SUDV | EBOV | MARV |
|---|---|---|---|---|---|---|
| | | Nucleoprotein | | | | |
| BDBV | | 79.4 | 66.9 | 66.1 | 74.2 | 33.5 |
| TAFV | 26.6 | | 79.8 | 77.6 | 83.2 | 54.6 |
| RESTV | 18.4 | 17.9 | | 79.8 | 82.4 | 52.2 |
| SUDV | 16.2 | 10.4 | 17.5 | | 80.8 | 37.2 |
| EBOV | 14.1 | 12.1 | 15.0 | 10.4 | | 35.1 |
| MARV | 12.3 | 9.2 | 9.7 | 8.8 | 5.2 | |
| | Glycoprotein mucin-like domain | | | | | |

| Survivor group | Antigens Hits | | | | | | | | | |
|---|---|---|---|---|---|---|---|---|---|---|
| MARV | MARV-GP Mucin 0.0001249 | MARV-GP dTM 0.0001249 | MARV-NP 0.0001249 | MARV-VP40 0.008741 | BDBV-GP Mucin 0.008242 | | | | | |
| SUDV | SUDV-GP dTM 0.02861 | SUDV-NP 0.001968 | RESTV-GP dTM 0.0137 | RESTV-NP 0.01939 | TAFV-NP 0.02861 | | | | | |
| BDBV | BDBV-GP mucin 0.026 | BDBV-GP dTM 0.012 | BDBV-NP 0.028 | BDBV-VP40 0.006 | SUDV-NP 0.036 | RESTV-NP 0.011 | RESTV-GP dTM 0.038 | TAFV-VP40 0.015 | EBOV-NP 0.002 | EBOV-VP40 0.021 |

FIGURE 14

METHOD AND COMPOSITION FOR DETERMINING SPECIFIC ANTIBODY RESPONSES TO SPECIES OF FILOVIRUS

CROSS-REFERENCE TO RELATED APPLICATIONS

This application is a National Stage Application under 35 U.S.C. § 371 of International Application No. PCT/US2015/34080, filed Jun. 3, 2015, which claims priority to U.S. Provisional Patent Application No. 62/007,195, filed on Jun. 3, 2014, which is incorporated by reference herein in its entirety.

STATEMENT REGARDING FEDERALLY SPONSORED RESEARCH

The invention was made with support from the National Institute of Allergy and Infectious Diseases (R01AI96215), and the Defense Threat Reduction Agency (contract CB3948).

SEQUENCE LISTING

This application is submitted with a Sequence Listing text file that serves as both the computer readable form (CRF) and the paper copy required under 37 C.F.R. § 1.821. The sequence listing, which is incorporated by reference, includes a the entitled "SequenceListing.txt" which is 92 kilobytes in size and was created on Jun. 1, 2015.

BACKGROUND

Filoviruses, which include *marburgviruses* and *ebolaviruses*, cause severe viral hemorrhagic fever. The first outbreak of *Marburg virus* was recorded in 1967 in Germany and Yugoslavia, and was traced to infected African green monkeys from Uganda (1). Since then, major outbreaks of *marburgviruses* have occurred in sub-Saharan Africa. The first outbreaks of *Ebola virus* were documented in Sudan and The Democratic Republic of Congo in 1976 (2, 3). Because no licensed therapeutics or vaccines are currently available, cycles of filovirus outbreaks are a major concern in biodefense as well as public health. Filoviral hemorrhagic fever is characterized by rapid disease onset and mortality rates of up to 90% (4). Following an incubation period that can range from 2-21 days, infected patients commonly develop non-specific flulike symptoms of fever, vomiting, loss of appetite, headache, abdominal pain, fatigue, and diarrhea, while bleeding occurs in a smaller number of infections (1, 3, 5). Case fatalities are associated with reduced adaptive immune responses (6, 7) and the release of high levels of immune response mediators (8-10) that contribute to vascular dysfunction, coagulation disorders, shock and eventual multi-organ failure (2).

There is a persistent need for sensitive and reliable serological approaches for examining filoviral infections. Because genetic material from the pathogen is often missing, antibody detection methods are indispensable, especially for examining nonviremic patients and for disease surveillance. While ELISAs for detecting specific IgG and IgM based on live virus preparation were previously developed (11-13), the need for BSL-4 labs and associated safety issues are major limitations. Serological assays based on recombinant filovirus antigens are alternatives that do not require infectious agents, and several ELISAs were reported (14-18). For example, Nakayama and coworkers developed a GP-based ELISA representative of all six species of filoviruses and analyzed human patient sera from Ebola and Marburg virus outbreaks (Nakayama et al, 2010). However, these previous methods have only addressed a limited number of antigens and species of filoviruses. The Filoviridae family includes one species of *Marburg virus* (*Marburg marburgvirus*), with five species of *Ebola virus* (*Sudan, Zaire, Reston, Bundibugyo*, and *Taï Forest ebolavirus*) that are each a cause of severe hemorrhagic fevers in primates including humans (2). Further complicating assay development, the single-stranded, negative-sensed RNA genome (~19 kB) encodes seven structural proteins (1, 19, 20) that are each potential antigens: the nucleoprotein (NP), virion protein 35 (VP35), VP40, glycoprotein (GP), VP30, VP24, and RNA-dependent RNA polymerase (L). Major functions of each component of the viral proteome were previously characterized. The RNA genome is encapsulated by NP, and the ribonucleoprotein complex is associated with VP35, VP30, and L (21, 22). Transcription and replication of the viral genome requires L, NP, and VP35 (23), while transcription for *Ebola virus*, but not *Marburg virus*, requires VP30 as an additional co-factor (24, 25). VP40 is a matrix protein critical for virion assembly as well as budding from infected cells (26, 27), and VP24 appears to play a role in nucleocapsid assembly and inhibition of interferon signaling (28-30). Unlike *Marburg* GP, *Ebola* GP is expressed following RNA editing, while the unedited transcript encodes a soluble GP that is released from infected cells (31, 32). Further, trimeric GP complexes on the virion surface are receptors for fusion and entry into the host cell (33-35).

Compositions and methods that can provide for a fast, accurate, and comprehensive serological analysis would help faciliate identification and diagnosis of filovirus infection (e.g., one or more filovirus antibodies in a sample) in the general human population as well as potentially animal populations. Such compositions and methods would provide an important tool in the detection, management, and containment of filovirus outbreaks, and ultimately help to reduce mortality rates and public panic that are associated with these hemorrhagic fever viruses.

SUMMARY

In one aspect the disclosure provides a detection agent comprising one or more amino acid sequences of a filovirus protein, or a fragment thereof, and a substrate, wherein the one or more amino acid sequences of the filovirus protein is attached to the substrate.

In embodiments, the one or more amino acid sequences of a filovirus protein is from a filovirus selected from *Marburg marburgvirus, Sudan ebolavirus, Zaire ebolavirus, Reston ebolavirus, Bundibugyo ebolavirus*, and *Taï Forest ebolavirus*. In some embodiments the one or more amino acid sequences of a filovirus protein, or fragment thereof, is selected from nucleoprotein (NP), virion protein 40 (VP40), glycoprotein (GP), virion protein (VP35), virion protein (VP30), virion protein (VP24), RNA-dependent RNA polymerase (L), or any combination thereof of the same or different filovirus. In some embodiments the detection agent comprises from two or more amino acid sequences to twenty or more amino acid sequences (e.g., 2, 3, 4, 5, 5, 6, 7, 8, 9, 10, 11, 12, 13, 14, 15, 16, 17, 18, 19, or 20, or more amino acid sequences) from the same or different filovirus. In some embodiments the detection agent comprises at least three different amino acid sequences of at least three different filovirus proteins, or fragments thereof, and in further embodiments, the at least three different proteins may comprise NP, VP40, and GP, or fragments thereof. In some embodiments the detection agent comprises a protein having at least 90% sequence identity to the sequence of a filovirus protein.

In some embodiments, the detection agent may comprise a substrate is selected from the group consisting of a microarray, microparticles, and nanoparticles, and such substrates may be made of materials including glasses, plastics, chemical/biological polymers, metal (magnetic and non-magnetic) semiconductors, ceramics, and the like. In some embodiments the detection agent is a microarray.

In certain embodiments, the one or more amino acid sequences of a filovirus protein may be provided as a recombinant protein or a fragment thereof.

In an aspect the disclosure provides a method for detecting the presence of filovirus-specific antibody in biological sample obtained from a subject comprising:
  (a) incubating the biological sample with a detection agent comprising one or more amino acid sequences of a filovirus protein, or a fragment thereof, attached to a substrate under conditions that allow binding of the filovirus-specific antibody to the detection agent; and
  (b) detecting the filovirus-specific antibody bound to detection agent.

In another aspect the disclosure provides a method for identifying a subject infected with a filovirus, comprising:
  determining whether a filovirus-specific antibody is present in a sample obtained from the subject, wherein the determining comprises:
  (a) incubating the biological sample with a detection agent comprising one or more amino acid sequences of a filovirus protein, or a fragment thereof, attached to a substrate under conditions that allow binding of the filovirus-specific antibody to the detection agent; and
  (b) detecting the filovirus-specific antibody bound to the detection agent,
  wherein the detection of the filovirus-specific antibody identifies that the subject is infected with a filovirus.

In a further aspect, the disclosure provides a method for identifying whether a subject is infected with a filovirus, comprising:
  determining whether an antibody to the filovirus is present in a sample obtained from the subject, wherein the determining comprises:
  (a) contacting the sample with at least one protein, or a fragment thereof, from the filovirus to which the antibody can specifically bind; and
  (b) detecting specific binding between the at least one protein and the antibody,
  wherein the detection of specific binding identifies that the subject is infected with a filovirus.

In various embodiments of the above aspects relating to methods, the filovirus may be selected from the group consisting of *Marburg marburgvirus, Sudan ebolavirus, Zaire ebolavirus, Reston ebolavirus, Bundibugyo ebolavirus,* and *Taï Forest ebolavirus* or any combination thereof. In embodiments the methods comprise one or more amino acid sequences of a filovirus protein, or a fragment thereof, comprises nucleoprotein (NP), virion protein 40 (VP40), glycoprotein (GP), virion protein (VP35), virion protein (VP30), virion protein (VP24), RNA-dependent RNA polymerase (L), or any combination thereof.

In some embodiments the detection agent comprises from two or more amino acid sequences to twenty or more amino acid sequences (e.g., 2, 3, 4, 5, 5, 6, 7, 8, 9, 10, 11, 12, 13, 14, 15, 16, 17, 18, 19, 20, or more amino acid sequences) from the same or different filovirus or filovirus protein. In some embodiments the detection agent comprises at least three different amino acid sequences of at least three different filovirus proteins, or fragments thereof, and in further embodiments, the at least three different proteins may comprise NP, VP40, and GP, or fragments thereof. In some embodiments the detection agent comprises a protein having at least 90% sequence identity to the sequence of a filovirus protein.

In further embodiments, the methods can comprise the comparison the amount of an filovirus-specific antibody detected according to the method with one or more control values (e.g., measuring the amount of signal generated from incubating the detection agent with a normal (healthy and/or uninfected) biological sample).

In other aspects the disclosure provides a kit comprising, the detection agent as described herein; at least one reagent that can detect a filovirus-specific antibody bound to the detection agent; and instructions for use of the kit.

In yet a further aspect, the disclosure provides a method for making the detection agent described herein, the method comprising:
  expressing one or more recombinant polynucleotide sequences encoding an amino acid sequence of a filovirus protein, or a fragment thereof in an expression system; and
  fixing the encoded amino sequence of a filovirus protein, or a fragment thereof, on a surface of the substrate.

In embodiments of this aspect, the method may comprise an recombinant expression system including a prokaryotic cell, a eukaryotic cell, or in vitro translation, or any combination thereof. In further embodiments, the prokaryotic cell may comprise a bacterium such as, for example, *E. coli*. In other embodiments, the eukaryotic cell may be selected from the group consisting of yeast, an insect cell, and a mammalian cell.

Other aspects and embodiments will be apparent to those of skill in the art in view of the description and illustrative Examples that follow.

BRIEF DESCRIPTION OF THE DRAWING

FIG. 5. Scatter plot of individual antibody responses for primates challenged with *Zaire ebolavirus*. Bound IgG were detected fluorescently on a microarray scanner. Background-corrected fluorescence intensities were averaged across technical replicates on the microarrays. Pre-vaccination, dark circles; post-vaccination, open circles; post-viral challenge, dark triangles. *Bundibugyo* (B), *Taï Forest* (T), *Marburg* (M), *Reston* (R), *Sudan* (S), and *Zaire* (Z).

FIG. 6. Scatter plot of individual antibody responses for primates challenged with *Marburg marburgvirus*. Bound IgG were detected fluorescently on a microarray scanner. Background-corrected fluorescence intensities were averaged across technical replicates on the microarrays. Pre-vaccination, dark circles; post-vaccination, open circles; post-viral challenge, dark triangles. *Bundibugyo* (B), *Taï Forest* (T), *Marburg* (M), *Reston* (R), *Sudan* (S), and *Zaire* (Z).

FIG. 9. Antibody reactivity to filoviral proteins in a cohort of *ebola* and *marburg* survivors. Heat map displaying IgG reactivity associated with filoviral infection and controls. Hierarchical clustering by Euclidean distance average linkage method was used to visualize protein microarray results. Normalized and log 2-transformed data was applied for creating the heat map. The IDs of proteins are listed in the rows (*insect and **mammalian expressed), the cells represent individual sera samples, and the survivor and control groups are listed on the bottom of the colored bars. The blue bars show ACAM2000 healthy controls, the purple bars healthy controls from Uganda and the green bars three MARV, SUDV and BDBV survivor groups.

FIG. 12. Antibody responses by a replication defective recombinant EBOV/SUDV GP vaccinated subject to filoviral proteins. The bars represent mean values of four replicates (* insect and ** mammalian expressed).

FIG. 13. Comparison antibody responses to GP proteins.

FIG. 14. List of significant antibody responses to autologous and heterologous antigens and their p-values. The three survivor groups are on the left column and the antigen hits are listed on the right cells.

DETAILED DESCRIPTION

Figure 1A:
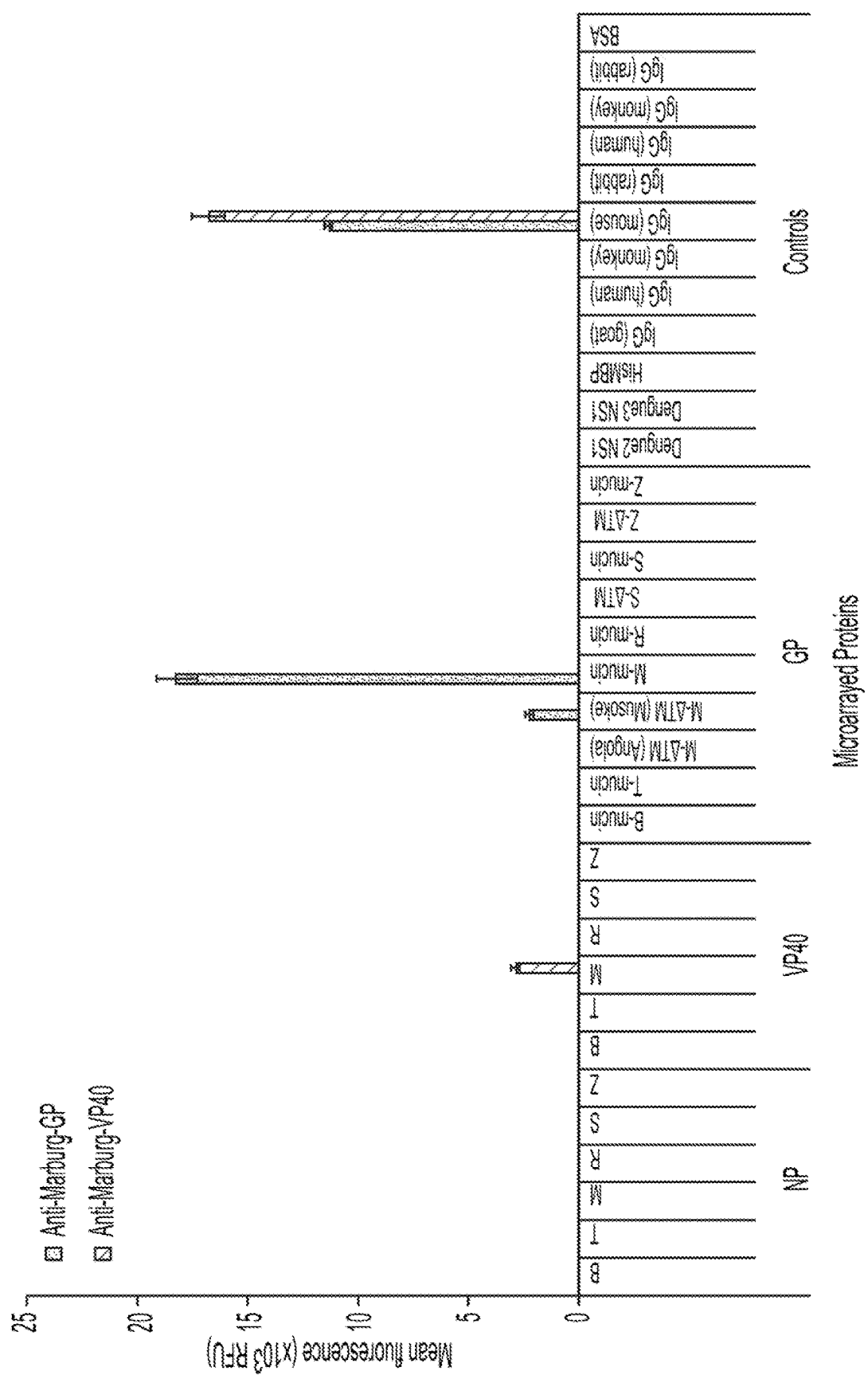
FIG. 1A-1C. Validation of filovirus microarray using control antibodies. A panel of antibodies against A) *Marburg virus*, B) *Zaire ebolavirus*, and C) *Sudan ebolavirus* proteins were tested on printed microarrays. All antibodies are mouse monoclonal except for anti-*Zaire*-NP and -VP40 which are both rabbit polyclonal. Bound antibodies were detected fluorescently on a microarray scanner. Background-corrected fluorescence intensities were averaged across technical replicates on the microarrays. Bars represent mean fluorescence (RFU)±SEM. All GP ΔTMs were expressed in insect cells except for *Marburg*-GP ΔTM (Musoke) which was expressed in mammalian cells. Bundibugyo (B), Taï Forest (T), Marburg (M), Reston (R), Sudan (S), and Zaire (Z).

As discussed in further detail below, the inventors have developed compositions of matter (e.g., detection agents, kits, etc.) and methods that can provide for fast, accurate, comprehensive and convenient (e.g., point-of-care assays) detection of filovirus antibodies in biological samples such as, for example, sera. The efficacy of the compositions and methods relating to the general technology is demonstrated through the illustrative embodiments disclosed in the Examples. For example, certain embodiments provide for the preparation and use of protein microarrays as the detection agent disclosed and described herein, and by including one or more amino acid sequences of at least one filovirus protein (e.g., GP or fragments thereof), or combinations of filovirus proteins and/or fragments thereof (e.g., NP, GP, and VP40, as discussed below), allow for the detection of an antibody to one or more filovirus (e.g., *Ebola* and/or *Marburg virus*) species. Further, and unexpectedly, the inventors have identified that in particular embodiments one or more amino acid sequences of filovirus proteins and/or fragments thereof, may be recombinantly expressed in expression systems, including prokaryotic cells, (e.g., *E. coli*) without any loss of filovirus-specific antibody binding activity or specificity.

In practicing the technology disclosed herein, many conventional techniques in molecular biology, protein biochemistry, cell biology, immunology, and microbiology are used. These techniques are well-known and are explained in, e.g., *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y., 1989); DNA Cloning: A Practical Approach, Vols. I and H, Glover, Ed. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, *Meth. Enzymol*., (Academic Press, Inc., 1984); *Gene Transfer Vectors for Mammalian Cells*, Miller & Calos, Eds. (Cold Spring Harbor Laboratory, NY, 1987); and *Meth. Enzymol*., Vols. 154 and 155, Wu & Grossman, and Wu, Eds., respectively. Methods to detect and measure the levels of protein complexes are well-known in the art and include ELISA assays, and co-immunoprecipitation assays.

All references referred to within the body of the application are incorporated herein by reference in their entirety.

Definitions

Virus as used herein refers to a small infectious agent that replicates only inside the living cells of other organisms. Viruses can infect all types of life forms, from animals and plants to microorganisms, including bacteria and archaea. Virus particles (known as virions) typically consist of two or three parts: i) the genetic material made from either DNA or RNA, long molecules that carry genetic information; ii) a protein coat that protects these genes; and in some cases iii) an envelope of lipids that surrounds the protein coat when they are outside a cell. The shapes of viruses range from simple helical and icosahedral forms to more complex structures. The average virus is about one one-hundredth the size of the average bacterium.

Filoviruses generally refer to viruses of the viral family called Filoviridae and infection can cause severe hemorrhagic fever in humans and nonhuman primates. So far, three members of this virus family have been identified: *Marburgvirus, Ebolavirus*, and *Cuevavirus*. Five species of *Ebolavirus* have been identified: *Taï Forest* (formerly Ivory Coast), *Sudan, Zaire, Reston* and *Bundibugyo*. *Ebola-Reston* is the only known Filovirus that does not cause severe disease in humans; however, it can still be fatal in monkeys and it has been recently recovered from infected swine in South-east Asia. Structurally, filovirus virions (complete viral particles) may appear in several shapes, a biological feature called pleomorphism. These shapes include long, sometimes branched filaments, as well as shorter filaments shaped like a "6", a "U", or a circle. Viral filaments may measure up to 14,000 nanometers in length, have a uniform diameter of 80 nanometers, and are enveloped in a lipid (fatty) membrane. Each virion contains one molecule of single-stranded, negative-sense RNA. New viral particles are created by budding from the surface of their hosts' cells; however, filovirus replication strategies are not completely understood.

The genus *Ebolavirus* (or "*Ebola*" or "*Ebola virus*") is a virological taxon included in the family Filoviridae, order Mononegavirales. The members of this genus are generally referred to as *ebolaviruses*. The five known virus species are named for the region where each was originally identified: *Bundibugyo ebolavirus, Reston ebolavirus, Sudan ebolavirus, Taï Forest ebolavirus* (originally *Côte d'Ivoire ebolavirus*), and *Zaire ebolavirus*.

The genus *Marburgvirus* (or "*Marburg*" or "*Marburg virus*") refers to the species, *Marburg marburgvirus*, which includes two known *marburgviruses, Marburg virus* (MARV) and *Ravn virus* (RAVV). Both viruses cause *Marburg virus* disease, a form of hemorrhagic fever, in humans and nonhuman primates.

*Cuevavirus* is a genus in the family Filoviridae that has one identified species, *Lloviu cuevavirus* (LLOV or "*cueva virus*"). Studies indicate that LLOV is a distant relative of the more widely known *Ebola* and *Marburg viruses*.

DNA is used herein (Deoxyribonucleic acid) is a molecule that encodes the genetic instructions used in the development and functioning of all known living organisms and many viruses. DNA is a nucleic acid; alongside proteins and carbohydrates, nucleic acids compose the three major macromolecules essential for all known forms of life. Most DNA molecules consist of two biopolymer strands coiled around each other to form a double helix. The two DNA strands are known as polynucleotides since they are composed of simpler units called nucleotides. Each nucleotide is composed of a nitrogen-containing nucleobase—either guanine (G), adenine (A), thymine (T), or cytosine (C)—as well as a monosaccharide sugar called deoxyribose and a phosphate group. The nucleotides are joined to one another in a chain by covalent bonds between the sugar of one nucleotide and the phosphate of the next, resulting in an alternating sugar-phosphate backbone. According to base pairing rules (A with T and C with G), hydrogen bonds bind the nitrogenous bases of the two separate polynucleotide strands to make double-stranded DNA.

Proteins are large biological molecules, or macromolecules, consisting of one or more long chains of amino acid residues (e.g., "peptide", "polypeptide", or "amino acid sequence"). Proteins perform a vast array of functions within living organisms, including catalyzing metabolic reactions, replicating DNA, responding to stimuli, and transporting molecules from one location to another. Structural differences in proteins typically arise based on differences between secondary structure (primarily sequence of amino acids), which is dictated by the nucleotide sequence of their genes, and tertiary and/or quaternary structure (protein folding, three-dimensional structure, and domain interactions), all of which can determine activity.

An antigen (Ag), abbreviation of antibody generator, is any structural substance which serves as a target for the receptors of an adaptive immune response, TCR or BCR or its secreted form antibody, respectively. Each antibody is specifically selected after binding to a certain antigen because of random somatic diversification in the antibody complementarity determining regions (a common analogy used to describe this is the fit between a lock and a key). In summary, an antigen is a molecule that binds to Ag-specific receptors but cannot induce an immune response in the body by itself. Antigen was originally a structural molecule that binds specifically to the antibody, but the term now also refers to any molecule or a linear fragment that can be recognized by highly variable antigen receptors (B-cell receptor or T-cell receptor) of the adaptive immune system.

An antibody (AB), also known as an immunoglobulin (Ig), is a large, Y-shape protein produced by plasma cells that is used by the immune system to identify and neutralize pathogens such as bacteria and viruses. The antibody recognizes a unique molecule of the harmful agent, called an antigen, via the variable region. Each tip of the "Y" of an antibody contains a paratope that is specific for one particular epitope (similarly analogous to a key) on an antigen, allowing these two structures to bind together with precision. Using this binding mechanism, an antibody can tag a microbe or an infected cell for attack by other parts of the immune system, or can neutralize its target directly (for example, by blocking a part of a microbe that is essential for its invasion and survival). The ability of an antibody to communicate with the other components of the immune system is mediated via its Fc region (located at the base of the "Y"), which contains a conserved glycosylation site involved in these interactions. The production of antibodies is the main function of the humoral immune system.

A microarray as used herein refers to the technology generally identified as a multiplex lab-on-a-chip. Typically a microarray comprises a 2D array on a solid substrate (usually a glass slide or silicon thin-film cell) that assays large amounts of biological material using high-throughput screening miniaturized, multiplexed and parallel processing and detection methods. A protein microarray (or protein chip) is a high-throughput method used to track the interactions and activities of proteins, and to determine their function, and determining function on a large scale. Its main advantage lies in the fact that large numbers of proteins can be tracked in parallel. The chip consists of a support surface such as a glass slide, nitrocellulose membrane, bead, or microtitre plate, to which an array of capture proteins is bound. Probe molecules, typically labeled with a fluorescent dye, may added to the array. Any reaction between the probe and the immobilized protein emits a fluorescent signal that is read by a laser scanner. Protein microarrays may be rapid, automated, economical, and highly sensitive, consuming small quantities of samples and reagents. Methodology relating to protein microarrays was introduced as early as 1983, illustrated using antibody-based microarrays (also referred to as antibody matrix).

Mucin are a family of high molecular weight, heavily glycosylated proteins (glycoconjugates) produced by epithelial tissues in most organisms of Kingdom Animalia. Mucins' key characteristic is their ability to form gels; therefore they are a key component in most gel-like secretions, serving functions from lubrication to cell signalling to forming chemical barriers. They often take an inhibitory role. Some mucins are associated with controlling mineralization, including nacre formation in mollusks, calcification in echinoderms and bone formation in vertebrates. They bind to pathogens as part of the immune system. Overexpression of the mucin proteins, especially MUC1, is associated with many types of cancer. Although some mucins are membrane-bound due to the presence of a hydrophobic membrane-spanning domain that favors retention in the plasma membrane, most mucins are secreted onto mucosal surfaces or secreted to become a component of saliva.

The cell is the basic structural, functional, and biological unit of all known living organisms. Cells are the smallest unit of life that can replicate independently, and are often called the "building blocks of life". A prokaryote is a single-celled organism that lacks a membrane-bound nucleus (karyon), mitochondria, or any other membrane-bound organelles. A eukaryote is any organism whose cells contain a nucleus and other organelles enclosed within membranes.

Recombinant protein is a protein produced by a recombinant DNA that encodes for the protein sequence. Recombinant DNA (rDNA) molecules are DNA molecules formed by laboratory methods of genetic recombination (such as molecular cloning) to bring together genetic material from multiple sources, creating sequences that would not otherwise be found in biological organisms. Once a recombinant DNA is inserted into bacteria, these bacteria will make protein based on this recombinant DNA. This protein is known as "Recombinant protein".

Infection is the invasion of an organism's body tissues by disease-causing agents, their multiplication, and the reaction of host tissues to these organisms and the toxins they produce. Infectious disease, also known as transmissible disease or communicable disease is illness resulting from an infection. Infections discussed herein are typically caused filoviruses.

Detection Agent

In a general aspect, the disclosure provides a detection agent comprising one or more amino acid sequences of a filovirus protein, or a fragment thereof, and a substrate wherein the one or more amino acid sequences of the filovirus protein is attached to substrate. In certain embodiments, the one more amino acid sequences of a filovirus protein may comprise a sequence of a protein from a filovirus selected from *Marburg marburgvirus, Sudan ebolavirus, Zaire ebolavirus, Reston ebolavirus, Bundibugyo ebolavirus*, and *Taï Forest ebolavirus*.

In some embodiments, the one or more amino acid sequences of a filovirus protein, or fragment thereof, may comprise a sequence from a nucleoprotein (NP), virion protein 40 (VP40), glycoprotein (GP), virion protein (VP35), virion protein (VP30), virion protein (VP24), RNA-dependent RNA polymerase (L), or a fragment thereof, or any combination thereof. Any amino acid sequence that provides for binding and recognition of a filovirus specific antibody may be used in connection with the detection agent. In some embodiments, the amino acid sequence may exhibit little to no cross-reactivity to filovirus specific antibodies that are directed to a particular type of filovirus or a particular filovirus protein. In certain embodiments the one or more amino acid sequences of a filovirus protein comprises GP, or fragment thereof. The GP or fragment thereof may comprise a mucin-like domain fragment of GP (GP-mucin) or a GP ectodomain (GPΔTM). While the detection agent comprises at least one amino acid sequence of a filovirus protein, it may also comprise a plurality of such amino acid sequences. In some embodiments the detection agent comprises from two or more amino acid sequences to twenty or more amino acid sequences (e.g., 2, 3, 4, 5, 5, 6, 7, 8, 9, 10, 11, 12, 13, 14, 15, 16, 17, 18, 19, 20, or more amino acid sequences) that may be selected from the same or different filovirus and/or the same or different filovirus protein. As a further example, in some embodiments, such as those illustrated in the non-limiting Examples, the detection agent may include at least three different amino acid sequences of at least three different filovirus proteins, or fragments thereof (e.g., NP, VP40, and GP, or fragments thereof).

In some embodiments, the amino acid sequences comprising the detection agent can comprise a sequence that is not identical to the protein sequence from which it is derived. Some minor changes in the primary amino acid sequence and/or post-translational modification and processing of the sequence may be allowable as long as the sequence modification does not interfere with the ability of the filovirus-specific antibody to bind. In some embodiments, the detection agent can comprise one or more amino acid sequences having at least 90% sequence identity (e.g., 90%, 91%, 92%, 93%, 94%, 95%, 96%, 97%, 98%, or 99%) to the filovirus protein from which it is derived. In some embodiments, the amino acid sequences may comprise an NP sequence having at least 90% sequence identity to the sequence selected from the group consisting of SEQ ID NO:4 (*Zaire* NP); SEQ ID NO: 10 (*Sudan* NP); SEQ ID NO: 16 (*Bundibugyo* NP); SEQ ID NO: 22 (*Taï Forest* NP); SEQ ID NO: 28 (*Reston* NP); and SEQ ID NO: 34 (*Marburg* NP); a VP40 sequence having at least 90% sequence identity to the sequence selected from the group consisting of SEQ ID NO: 2 (*Zaire* VP40); SEQ ID NO: 8 (*Sudan* VP40); SEQ ID NO: 14 (*Bundibugyo* VP40); SEQ ID NO: 20 (*Taï Forest* VP40); SEQ ID NO: 26 (*Reston* VP40); and SEQ ID NO: 32 (*Marburg* VP40); and/or a GP-mucin domain having at least 90% sequence identity to the sequence selected from the group consisting SEQ ID NO: 6 (*Zaire* GP-mucin); SEQ ID NO: 12 (*Sudan* GP-mucin); SEQ ID NO: 18 (*Bundibugyo* GP-mucin); SEQ ID NO: 24 (*Taï Forest* GP-mucin); SEQ ID NO: 30 (*Reston* GP-mucin); and SEQ ID NO: 36 (*Marburg* GP-mucin). In further embodiments, the detection agent may comprise an NP sequence selected from the group consisting of SEQ ID NO: 4 (*Zaire* NP); SEQ ID NO: 10 (*Sudan* NP); SEQ ID NO: 16 (*Bundibugyo* NP); SEQ ID NO: 22 (*Taö Forest* NP); SEQ ID NO: 28 (*Reston* NP); and SEQ ID NO: 34(*Marburg* NP); a VP40 selected from the list consisting of SEQ ID NO: 2 (*Zaire* VP40); SEQ ID NO: 8 (*Sudan* VP40); SEQ ID NO: 14 (*Bundibugyo* VP40); SEQ ID 20 (*Taï Forest* VP40); SEQ ID NO: 26 (*Reston* VP40); SEQ ID NO: 32 (*Marburg* VP40); and/or a GP-mucin domain selected from the group consisting of SEQ ID NO: 6 (*Zaire* GP-mucin); SEQ ID NO: 12 (*Sudan* GP-mucin); SEQ ID NO: 18 (*Bundibugyo* GP-mucin); SEQ ID NO: 24 (*Taï Forest* GP-mucin); SEQ ID NO: 30 (*Reston* GP-mucin); and SEQ ID NO: 36 (*Marburg* GP-mucin).

As discussed herein, in certain embodiments the substrate may comprise a bead or particle (e.g., microparticle or nanoparticle). In other embodiments the substrate may comprise a substantially planar surface with a plurality of addressable locations that are each associated with a known amino acid sequence of a filovirus protein, and optionally one or more control locations (e.g., a microarray). As discussed further, in some embodiments, the one or more amino acid sequences of a filovirus protein is provided as a recombinant protein or a fragment thereof.

In certain embodiments, the detection agent can comprise any one or more controls such as, for example, a positive control, a negative control, an assay standard, an assay calibrator, a competition assay ligand, a labeled peptide or a solid-phase capture agent. Similarly in some embodiments the amino acid sequences (including any controls as well as the amino acid sequence(s) of a filovirus protein(s)) may comprise a synthetic peptide, a recombinant polypeptide, a substantially purified natural polypeptide, a peptide mimetic, an oligonucleotide aptamer, a polypeptide aptamer, any fragment thereof that can be bound by a filovirus-specific antibody and any combinations thereof. In certain embodiments the detection agent comprises an amino acid sequence of a filovirus protein that is recombinantly produced.

In certain embodiments the detection agent comprises a protein microchip or microarray comprising one or more amino acid sequences of a filovirus protein, or a fragment thereof, and a substrate to which the one or more amino acid sequences are attached. In these embodiments, the microarrays may be useful in a variety of applications including large-scale and/or high-throughput screening for a filovirus-specific antibody that bind to the microarray. In other embodiments, the microarray can be used to identify compound or agents that are capable of modulating the interactions between the filovirus-specific antibody and the amino acid sequence to which it binds.

Regardless of the particular format (e.g., microarray-based or particle-based), the detection agent may be prepared according to any of the techniques described herein or otherwise known in the art. For example, in embodiments relating to a protein microarray, the array can be prepared in a number of methods known in the art. For example, glass microscope slides are treated with an aldehyde-containing silane reagent. Small volumes of protein samples in a phosphate-buffered saline with 40% glycerol may be spotted onto the treated slides using a high-precision contact-printing robot. After incubation, the slides are immersed in a buffer containing for example, bovine serum albumin (BSA) to quench the unreacted aldehydes and to form a BSA layer that functions to prevent non-specific protein binding in subsequent applications of the array/microchip. Alternatively, proteins or protein complexes can be attached to a BSA-NHS slide by covalent linkages. BSA-NHS slides are fabricated by first attaching a molecular layer of BSA to the surface of glass slides and then activating the BSA with N,N'-disuccinimidyl carbonate. As a result, the amino groups of the lysine, aspartate, and glutamate residues on the BSA are activated and can form covalent urea or amide linkages with protein samples spotted on the slides. Alternatively, arrays may be prepared as discussed in the illustrative Examples below.

Methods

In further aspects, the disclosure relates to a number of methods. In an aspect the disclosure provides a method for detecting the presence of filovirus-specific antibody in biological sample obtained from a subject including: (a) incubating the biological sample with a detection agent comprising one or more amino acid sequences of a filovirus protein, or a fragment thereof, attached to a substrate under conditions that allow binding of the filovirus-specific antibody to the detection agent; and (b) detecting the filovirus-specific antibody bound to detection agent.

In another aspect, the disclosure provides a method for identifying a subject infected with a filovirus, comprising determining whether a filovirus-specific antibody is present in a sample obtained from the subject, wherein the determining includes: (a) incubating the biological sample with a detection agent comprising one or more amino acid sequences of a filovirus protein, or a fragment thereof, attached to a substrate under conditions that allow binding of the filovirus-specific antibody to the detection agent; and (b) detecting the filovirus-specific antibody bound to the detection agent, wherein the detection of the filovirus-specific antibody identifies that the subject is infected with a filovirus.

In yet another aspect, the disclosure provides a method for identifying whether a subject is infected with a filovirus, comprising: determining whether an antibody to the filovirus is present in a sample obtained from the subject, wherein the determining includes: (a) contacting the sample with at least one protein, or a fragment thereof, from the filovirus to which the antibody can specifically bind; and (b) detecting specific binding between the at least one protein or the fragment thereof and the antibody, wherein the detection of specific binding identifies that the subject is infected with a filovirus.

Similarly to the embodiments relating to the detection agent discussed herein, in some embodiments of the aspects relating to the above methods, the filovirus may be selected from the group consisting of *Marburg marburgvirus, Sudan* ebolavirus, Zaire ebolavirus, Reston ebolavirus, Bundibugyo ebolavirus, and Taï Forest ebolavirus.

In some embodiments the at least one protein or fragment thereof comprises nucleoprotein (NP), virion protein 40 (VP40), glycoprotein (GP), virion protein (VP35), virion protein (VP30), virion protein (VP24), RNA-dependent RNA polymerase (L), or any combination thereof, from any one or more filoviruses. Any amino acid sequence that provides for binding and recognition of a filovirus specific antibody may be used in connection with the method. In some embodiments, the amino acid sequence may exhibit little to no cross-reactivity to filovirus specific antibodies that are directed to a particular type of filovirus or a particular filovirus protein. In certain embodiments the one or more amino acid sequences of a filovirus protein comprises GP, or fragment thereof. The GP or fragment thereof may comprise a mucin-like domain fragment of GP (GP-mucin) or a GP ectodomain (GPΔTM). While the methods comprise at least one amino acid sequence of a filovirus protein, the methods may also comprise a plurality of such amino acid sequences from a single filovirus protein, and/or a plurality of filovirus proteins, and/or a plurality of filoviruses. As illustrated in the non-limiting Examples, the methods may include at least three, at least four, at least five or at least six different amino acid sequences from filovirus proteins, or fragments thereof from different filoviruses (e.g., NP, VP40, and GP-mucin, GP-ectodomain, etc. or fragments thereof).

In some embodiments, the methods can include amino acid sequences that are not identical to the protein sequence(s) from which the sequences are derived. Some minor changes in the primary amino acid sequence and/or post-translational modification and processing of the sequence may be included as long as the sequence change or modification does not interfere with the ability of the filovirus-specific antibody to bind the sequence. In some embodiments, the amino acid sequences have at least 90% sequence identity (e.g., 90%, 91%, 92%, 93%, 94%, 95%, 96%, 97%, 98%, or 99%) to the filovirus protein from which the sequence(s) are derived. In some embodiments, the amino acid sequences may comprise an NP sequence having at least 90% sequence identity to the sequence selected from the group consisting of SEQ ID NO:4 (Zaire NP); SEQ ID NO: 10 (Sudan NP); SEQ ID NO: 16 (Bundibugyo NP); SEQ ID NO: 22 (Taï Forest NP); SEQ ID NO: 28 (Reston NP); and SEQ ID NO: 34 (Marburg NP); a VP40 sequence having at least 90% sequence identity to the sequence selected from the group consisting of SEQ ID NO: 2 (Zaire VP40); SEQ ID NO: 8 (Sudan VP40); SEQ ID NO: 14 (Bundibugyo VP40); SEQ ID NO: 20 (Taï Forest VP40); SEQ ID NO: 26 (Reston VP40); and SEQ ID NO: 32 (Marburg VP40); and/or a GP-mucin domain having at least 90% sequence identity to the sequence selected from the group consisting SEQ ID NO: 6 (Zaire GP-mucin); SEQ ID NO: 12 (Sudan GP-mucin); SEQ ID NO: 18 (Bundibugyo GP-mucin); SEQ ID NO: 24 (Taï Forest GP-mucin); SEQ ID NO: 30 (Reston GP-mucin); and SEQ ID NO: 36 (Marburg GP-mucin). In further embodiments, the methods may comprise an NP sequence selected from the group consisting of SEQ ID NO: 4 (Zaire NP); SEQ ID NO: 10 (Sudan NP); SEQ ID NO: 16 (Bundibugyo NP); SEQ ID NO: 22 (Taï Forest NP); SEQ ID NO: 28 (Reston NP); and SEQ ID NO: 34(Marburg NP); a VP40 selected from the list consisting of SEQ ID NO: 2 (Zaire VP40); SEQ ID NO: 8 (Sudan VP40); SEQ ID NO: 14 (Bundibugyo VP40); SEQ ID 20 (Taï Forest VP40); SEQ ID NO: 26 (Reston VP40); SEQ ID NO: 32 (Marburg VP40); and/or a GP-mucin domain selected from the group consisting of SEQ ID NO: 6 (Zaire GP-mucin); SEQ ID NO: 12 (Sudan GP-mucin); SEQ ID NO: 18 (Bundibugyo GP-mucin); SEQ ID NO: 24 (Taï Forest GP-mucin); SEQ ID NO: 30 (Reston GP-mucin); and SEQ ID NO: 36 (Marburg GP-mucin). In certain embodiments of the methods, the methods comprise the detection agent as described herein.

In some embodiments, the methods include incubation of the sample with a detection agent at temperature and for a period of time. While the time and temperature of the incubation, or reaction, may vary it will suitably fall within a range that allows for the specific binding of a filovirus specific antibody to an amino acid that it can bind, or in some embodiments, bind specifically. A further embodiment provides for temperatures and times that are effective to facilitate binding of an antibody in the sample to a filovirus protein or a fragment thereof, while avoiding nonspecific interaction between the antibodies and a filovirus protein or a fragment thereof.

In embodiments of the above methods, the sample or biological sample may comprise any biologically-derived material that may contain antibodies, or in which antibodies are typically present. In some embodiments, the sample may be derived from a mammal having a functioning or compromised an immune system. In some embodiments, the biological samples may comprise tissue, cells, or a biological fluid, such as blood (including serum, or whole blood obtained from a finger prick), GCF, amniotic fluid, BALF, salvia, tears, urine, lymphatic fluid, sputum, or cerebrospinal fluid taken from a mammal. In other embodiments, the biological sample may comprise cell cultures, cell lysates, or cellular fluids. In particular embodiments, the sample may comprise blood or serum.

In one embodiment of the aspects relating to methods, the methods can be used to detect and determine the presence of a filovirus specific antibody in a sample. In further embodiments, a method may comprise determining the amount of a filovirus specific antibody or a complex between a filovirus specific antibody and one or more filovirus antigens, proteins, or fragments thereof. Thus, the amount may be measured by determining the amount of the antibodies and/or complexes in a sample. Detection may be performed by any method and technique routinely used in the art such as, for example, using an antibody which is detectably labeled, or which can be subsequently labeled. A variety of formats can be employed to determine whether a sample contains a filovirus specific antibody. Immunoassay methods useful in the method detection can include, but are not limited to, dot blotting, western blotting, protein chips, immunoprecipitation (IP), competitive and non-competitive protein binding assays, enzyme-linked immunosorbant assays (ELISA), and others commonly used and widely-described in scientific and patent literature, and many employed commercially. One of skill in the art can readily adapt known protein/antibody detection methods for use in determining whether samples contain a biomarker (e.g., a filovirus specific antibody) and the relative concentration in the sample. Further, the methods can include processing of the sample to isolate a target (e.g., a filovirus specific antibody or complex thereof) using known techniques including, for example, those described in Harlow & Lane, *Antibodies: A Laboratory Manual* (Cold Spring Harbor Laboratory Press, Cold Spring Harbor, N.Y., 1988).

Detection antibodies can be used in the methods and kits disclosed herein, including, for example, western blots or ELISA, to detect the formation of complexes formed between one or more filovirus-specific antibody and an amino acid sequence of a filovirus protein or fragment thereof. In such uses, it is possible to immobilize either the antibody or complexes on a solid support. Supports or carriers include any support capable of binding an antigen or an antibody, and are generally known in the art. Such supports may include, for example glass, polystyrene, polypropylene, polyethylene, dextran, nylon, amylases, natural and modified celluloses, polyacrylamides, ceramics, semiconductors, metal, and magnetite.

In one embodiment, the concentration of an antibody and/or one or more filovirus proteins or fragments thereof is determined in a biological sample obtained from a subject, including, for example, a human patient. For example, the antibody and/or the filovirus antigen can be isolated or purified from a sample obtained from cells, serum, tissue, or an organ of the subject, as discussed herein, and the amount thereof is determined. In some embodiments, the filovirus antibody and/or a complex comprising the filovirus antibody and an amino acid sequence of a filovirus protein or fragment thereof complex can be prepared from cells, tissue or organ samples by coimmunoprecipitation using an antibody immunoreactive with an interacting protein member, a bifunctional antibody that is immunoreactive with two or more interacting protein members of the protein complex, or an antibody selectively immunoreactive with the antibody and/or the complex. In some embodiments, bifunctional antibodies or antibodies immunoreactive with only free interacting filovirus antibodies are used, individual filovirus antibodies not complexed with other proteins may also be isolated along with the protein complex containing such individual antibodies. The complexes, filovirus specific antibodies and filovirus antigens may be separated from other proteins and biological materials/molecules in samples using methods known in the art, e.g., size-based separation methods such as gel filtration, or by removing the complex from the sample using another antibody having specific binding activity for the complex, filovirus antibody, and/or filovirus protein. Additionally, antibodies and proteins (and complexes between them) in a sample can be separated in a gel such as polyacrylamide gel and subsequently immuno-blotted using an antibody immunoreactive with the protein and/or complex.

Alternatively, the concentration can be determined in a sample without separation, isolation or purification. For this purpose, an antibody selectively immunoreactive with the filovirus-specific antibody, filovirus antigen, and/or complex may be used in an immunoassay. For example, immunocytochemical methods can be used. Other antibody-based techniques are suitable and are generally known in the art including, for example, enzyme-linked immunosorbent assay (ELISA), radioimmunoassay (RIA), immunoradiometric assays (IRMA), fluorescent immunoassays, protein A immunoassays, and immunoenzymatic assays (IEMA).

Methods of Manufacture

The disclosure also provides a method for making the detection agent as described herein comprising: expressing one or more recombinant polynucleotide sequences encoding an amino acid sequence of a filovirus protein, or a fragment thereof in an expression system; and fixing the encoded amino sequence of a filovirus protein, or a fragment thereof, on a surface of the substrate. The expression system includes a prokaryotic cell, a eukaryotic cell, or in vitro translation, or any combination thereof. The prokaryotic cell comprises *E. coli*. The eukaryotic cell is selected from the group consisting of yeast, an insect cell, and a mammalian cell.

In these embodiments, the methods further comprise the general techniques and reagents that are known in the art and which may find common use in preparing detection agents (e.g., protein microarrays, protein-based microparticles, and/or protein-based nanoparticles).

Kits

Another aspect relates to a kit including a detection agent as disclosed herein, at least one reagent that can detect a filovirus-specific antibody bound to the detection agent, and instructions for use of the kit. A kit may be used for conducting the diagnostic and screening methods described herein. Typically, the kit should contain, in a carrier or compartmentalized container, and additional reagents and buffers useful in any of the above-described embodiments of the diagnosis method. The carrier can be a container or support, in the form of, for example, bag, box, tube, rack, and is optionally compartmentalized. The carrier may define an enclosed confinement for safety purposes during shipment and storage. In one embodiment, the kit includes an antibody that is selectively immunoreactive with a complex comprising a filovirus-specific antibody and an amino acid sequence of a filovirus protein, or fragment thereof as described herein. In some embodiments the kit includes an antibody that is selectively immunoreactive with a filovirus-specific antibody (e.g., an anti-mammal antibody, such as an anti-human antibody) that can detect the presence of the filovirus-specific antibody bound to the detection agent. The antibodies may be labeled with a detectable marker such as radioactive isotopes, or enzymatic or fluorescence markers. Alternatively, additional secondary antibodies such as labeled anti-IgG and the like may be included for detection purposes. Optionally, the kit can include one or more of proteins sequences as a control or comparison purposes. Instructions for using the kit or reagents contained therein are also included in the kit.

The above aspects and embodiments are further illustrated in the non-limiting Examples that follow. While the Examples may refer to specific aspects of the disclosure, it will be appreciated that the information is merely provided for purposes of illustration and exemplification of the broader disclosure.

EXAMPLE 1

Cloning. Full-length genes for NP and VP40, and the GP mucin-like domain fragment (GP-mucin) for six filovirus species: *Reston* (REBOV), *Bundibugyo* (BEBOV), *Zaire* (ZEBOV), *Sudan* (SEBOV), and *Taï Forest ebolavirus* (TAFV); and *Marburg marburgvirus* (MARV) were cloned into pENTR™/TEV/D-TOPO® vector (Life Technologies, Grand Island, N.Y.) and sequence-verified. The nucleotide substitutions found in cloned sequence compared with the reference sequence from GenBank are summarized in Table 1. All entry vector clones were shuttled into destination *E. coli* expression vectors via LR reaction (LR Clonase® II, Life Technologies). Specifically, VP40 (*Zaire* VP40—SEQ ID NO: 1; *Sudan* VP40—SEQ ID NO: 7; *Bundibugyyo* VP40—SEQ ID NO: 13; *Taï Forest* VP40—SEQ ID NO: 19; *Reston* VP40—SEQ ID NO: 25; and *Marburg* VP 40—SEQ ID NO: 31) and GP-mucin (*Zaire* GP-mucin—SEQ ID NO: 5; *Sudan* GP-mucin—SEQ ID NO: 11; *Bundibugyo* GP-mucin—SEQ ID NO: 17; *Taï Forest* GP-mucin—SEQ ID NO: 23; *Reston* GP-mucin—SEQ ID NO: 29; and *Marburg* GP-mucin—SEQ ID NO: 35) ORFs were shuttled into pDESTHisMBP (Addgene plasmid 11085) containing an N-terminal HisMBP tag, while all NP (*Zaire* NP—SEQ ID NO: 3; *Sudan* NP—SEQ ID NO: 9; *Bundi-* bugyo NP—SEQ ID NO: 15; Taï Forest NP—SEQ ID NO: 21; Reston NP—SEQ ID NO: 27; and Marburg NP—SEQ ID NO: 33) ORFs were shuttled into pDEST17 (Life Technologies) containing an N-terminal His tag.

TABLE 1

Summary of cloned filovirus sequences compared to GenBank reference sequences

| Species[1] | Gene | Amino Acid Residues | GenBank Sequence | Nucleotide Substitutions[3] |
|---|---|---|---|---|
| Bundibugyo ebolavirus | VP40 | 1-326 | FJ217161.1 | None |
|  | NP | 1-739 | FJ217161.1 | C1735T (silent) |
|  | GP-mucin | 313-465 | FJ217161.1 | C6973T (silent), A7363G (silent) |
| Tai Forest ebolavirus | VP40 | 1-326 | FJ217162.1 | None |
|  | NP | 1-739 | FJ217162.1 | None |
|  | GP-mucin | 313-465 | FJ217162.1 | None |
| Reston ebolavirus (Pennsylvania) | VP40 | 1-331 | AF522874.1 | G4490A (silent), A5466G (Asn to Asp) |
|  | NP | 1-739 | AF522874.1 | T2188C (silent) |
|  | GP-mucin | 314-466 | AY769362. | G7093A (silent) |
| Sudan ebolavirus (Boniface) | VP40 | 1-326 | FJ968794.1 | T4465C (silent) |
|  | NP | 1-738 | AF173836.1 | C2581T (silent) |
|  | GP-mucin | 313-465 | FJ968794.1 | A7112G (silent) |
| Zaire ebolavirus (Mayinga) | VP40 | 1-326 | AF499101.1 | G4496A (silent), A4592G (silent), T5204C (silent) |
|  | NP | 1-739 | AF086833.2 | A491G (Ile to Val) |
|  | GP-mucin[2] | 313-465 | JQ352783.1 | None |
| Marburg marburgvirus (Musoke) | VP40 | 1-303 | DQ217792.1 | None |
|  | NP | 1-695 | DQ217792.1 | None |
|  | GP-mucin | 289-505 | DQ217792.1 | A6906T (silent) |

[1]Where available, strain names are in parentheses.
[2]Zaire ebolavirus GP-mucin sequence is from the Kikwit strain.
[3]The position of nucleotide substitutions are based on GenBank sequence as reference. Corresponding amino acid change is noted in parentheses. Otherwise, the mutation is noted as silent.

Protein expression and purification. Proteins VP40 (Zaire VP40—SEQ ID NO: 2; Sudan VP40: SEQ ID NO: 8; Bundibugyo VP40—SEQ ID NO: 14; Taï Forest VP40—SEQ ID NO: 20; Reston VP40—SEQ ID NO: 26; and Marburg VP40—SEQ ID NO: 32), NP (Zaire NP—SEQ ID NO: 4; Sudan NP—SEQ ID NO: 10; Bundibugyo NP—SEQ ID NO: 16; Taï Forest NP—SEQ ID NO: 22; Reston NP—SEQ ID NO: 28; and Marburg NP—SEQ ID NO: 34), GP-mucin (Zaire GP-mucin—SEQ ID NO: 6; Sudan GP-mucin—SEQ ID NO: 12; Bundibugyo GP-mucin—SEQ ID NO: 18; Taï Forest GP-mucin—SEQ ID NO: 24; Reston GP-mucin—SEQ ID NO: 30; and Marburg GP-mucin—SEQ ID NO: 36) were expressed in either BL21-AI™ cells (Life Technologies) or Rosetta™ 2(DE3) cells (EMD Millipore, Billerica, Mass.). Expression for pDESTHisMBP constructs was induced with 1 mM IPTG, while expression for pDEST17 18° C. was induced lysed using with 0.2% L-arabinose. Pelleted cells from overnight cultures grown at 18° C. were lysed using B-PER reagent (Thermo Scientific, Rockford, Ill.) supplemented with 2× Halt™ Protease and Phosphatase Inhibitors Cocktail, EDTA-free (Thermo Scientific); 0.2 mg/mL lysozyme; 50-100 U/mL DNaseI (Thermo Scientific); and 2 mM PMSF. Lysates were separated into supernatant and insoluble pellet fractions by centrifugation, and induced protein expression was confirmed through Western blotting or mass spectrometry and Coomassie staining. HisMBP-tagged VP40s and GP-mucins were soluble and present in the supernatant fraction. With the exception of ZEBOV NP (Zaire-NP) (SEQ ID NO: 4), all His-tagged NPs were insoluble and predominantly in the pellet fraction. Supernatant containing expressed VP40s were loaded onto HisTrap™ HP columns (GE Healthcare, Piscataway, N.J.) pre-equilibrated with 20 mM sodium phosphate, 0.5 M NaCl, 40 mM imidazole, pH 7.4. VP40 fractions were collected by applying an imidazole step elution. All GP-mucins except MARV GP-mucin (Marburg-GP-mucin) were purified using HisTrap™ HP columns. Binding and washing steps were conducted with 25 mM HEPES, 0.5 M NaCl, 25 mM imidazole, pH 8, and bound GP-mucins were eluted using an imidazole gradient. Marburg-GP-mucin was purified using MBPTrap™ HP column pre-equilibrated with 25 mM HEPES, 0.2 M NaCl, 1 mM EDTA, pH 7.4. Bound protein was eluted using 25 mM HEPES, 0.2 M NaCl, 1 mM EDTA, 10 mM maltose, pH 7.4. NPs were purified through on-column refolding on HisTrap™ HP columns. Briefly, NP pellets were re-solubilized in 25 mM HEPES, 0.2 M NaCl, 25 mM imidazole, 1 mM beta-mercaptoethanol, 6 M guanidine hydrochloride, pH 8. Proteins were bound to columns under denaturing conditions and refolded using a 6 to 0 M urea gradient over a 30 column volume range. Refolded proteins were eluted using an imidazole gradient. Although Zaire-NP was found in the supernatant, the protein did not appear to bind to the HisTrap™ column under the conditions used for VP40 purification. This may have been due to a hidden His tag, and thus, guanidine hydrochloride was added directly to Zaire-NP supernatant to a final concentration of 6 M in order to expose the His tag. Denatured Zaire-NP was processed in a similar manner as the other re-solubilized NPs. Purity and concentration of collected fractions were measured by Agilent Protein 230 kit (Agilent Technologies). All purified proteins were stored at −20° C. in their respective elution buffers with glycerol added to a final concentration of 25%.

Figure 4:
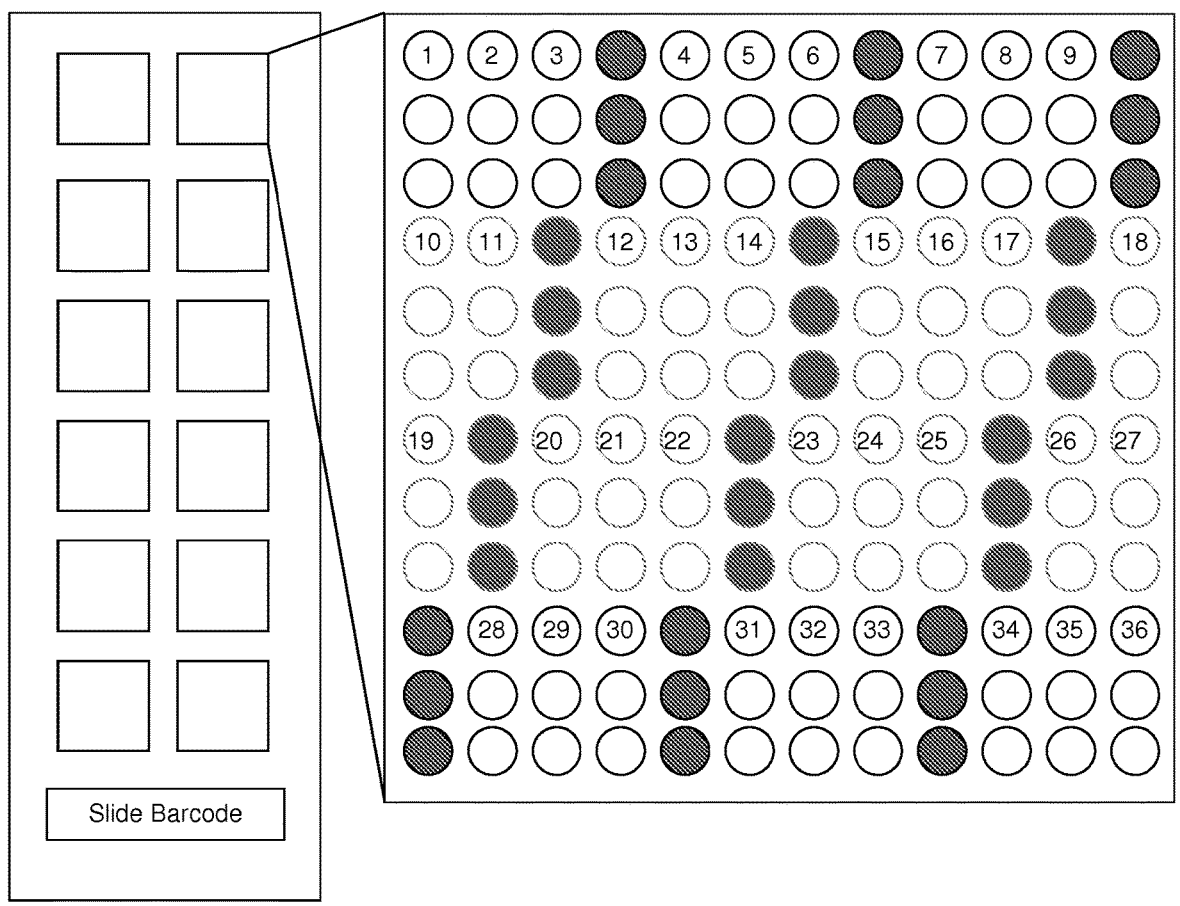
FIG. 4A-B. Microarray schematic and representative scanned fluorescent image of processed microarray. A) Slide schematic shows multiple 12×12 microarrays printed on a slide, along with an enlarged layout of an individual microarray. Table below provides the sample identity for each triplicate microarray spots. Red circles represent fluorescently-labeled streptavidin serving as reference markers for orientation purposes. *Bundibugyo* (B), *Taï Forest* (T), *Marburg* (M), *Reston* (R), *Sudan* (S), and *Zaire* (Z). B) Representative GenePix®-scanned image of microarray processed with naïve (left) and post-challenge sera (right) from the ZEBOV vaccine study.
Figure 4:
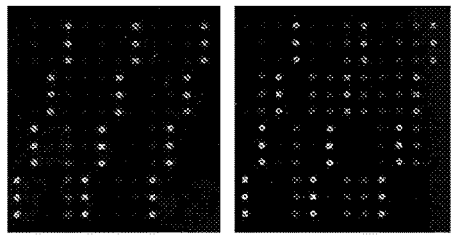
Figure 7:
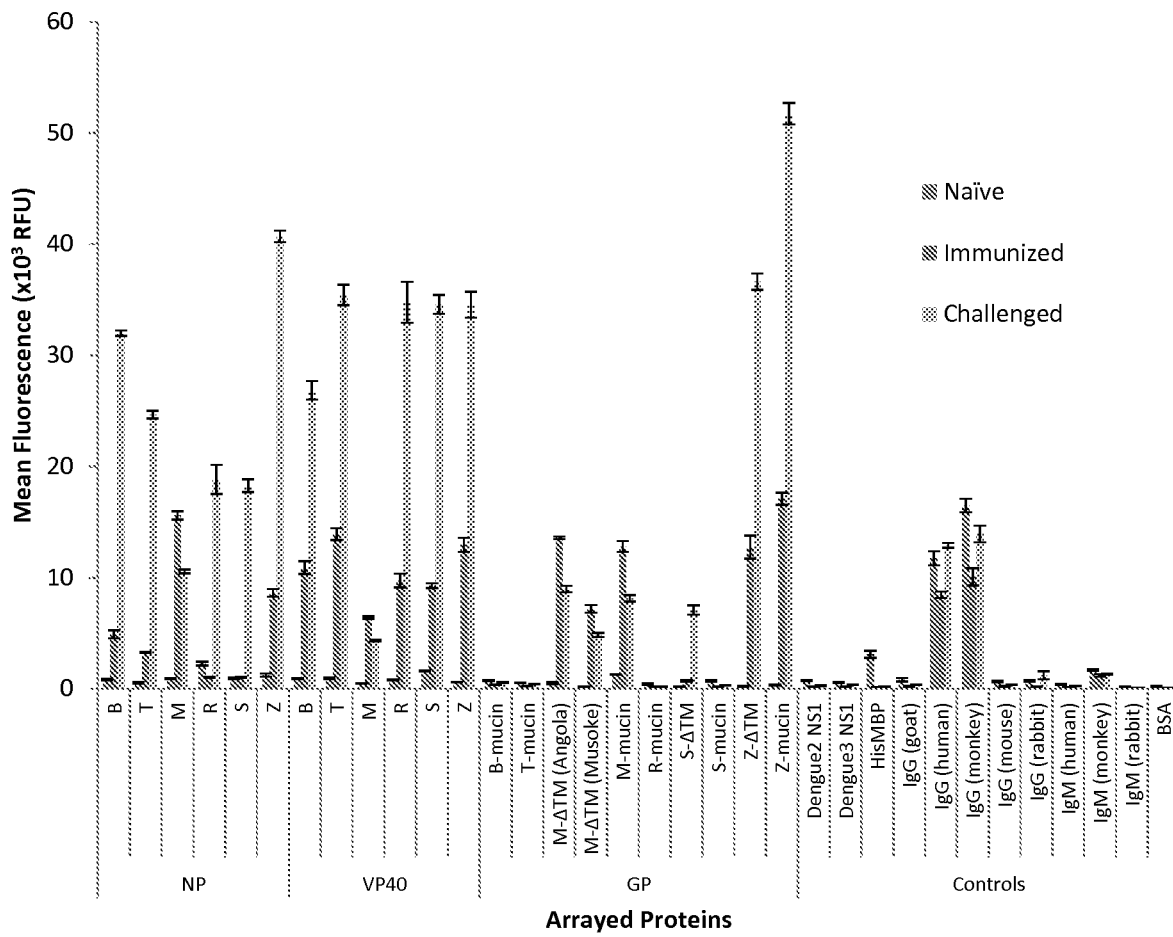
FIG. 7. IgM signals for sera collected from a single animal in the ZEBOV challenge groups. Bound antibodies were detected fluorescently on a microarray scanner. Background-corrected fluorescence intensities were averaged across technical replicates on the microarrays. *Bundibugyo* (B), *Taï Forest* (T), *Marburg* (M), *Reston* (R), *Sudan* (S), and *Zaire* (Z).

Microarray printing. The purified recombinant proteins were spotted (FIG. 4A-B) on nitrocellulose-coated FAST® slides (KeraFAST, Boston, Mass.), using a contactless inkjet microarray printer (ArrayJet, Edinburgh, Scotland). The microarray included a total of 34 proteins: i) E. coli-expressed filovirus antigens; ii) insect cell-expressed ZEBOV and SEBOV and Marburg virus Angola) GP ectodomain (ΔTM) (IBT Bioservices, Gaithersburg, Md.); iii) mammalian cell-expressed Marburg virus (Musoke) GP ΔTM (IBT Bioservices); iv) human, monkey, mouse, rabbit, and goat IgG (Rockland Immunochemicals, Gilbertsville, Pa.); v) human, monkey, and rabbit IgM (Rockland Immunochemicals; vi) HisMBP (ProteinOne, Rockville, Md.); vii)

dengue virus serotype 2 (dengue2) and 3 (dengue3) nonstructural protein 1 (NS1); and viii) BSA (Thermo Scientific). The purified dengue virus proteins were previously described (36). Briefly, the proteins were expressed with a HisMBP tag in *E. coli* and purified via immobilized metal affinity chromatography. Each protein was printed in triplicates. All purified proteins were diluted to 200 ng/uL in printing buffer (25 mM HEPES, 0.5 M NaCl, 25% glycerol, 1 mM DTT, pH 8). Alexa Fluor® 647-conjugated streptavidin (Life Technologies) was diluted 1:50 in printing buffer and included in the microarray as reference markers. Buffer served as empty placeholders on the microarray. Printed slides were desiccated overnight under vacuum and stored at −20° C.

Microarray processing. All microarray processing steps were performed under 21° C. conditions, and each antibody or serum sample was processed in duplicate microarrays. Printed microarrays were incubated for 1 hour in 1× Biacore Flexchip blocking buffer (GE Healthcare) with 2% normal goat serum (Vector Laboratories, Burlingame, Calif.) or 2% normal rabbit serum. Microarrays were washed three (3) times at five (5) minutes each with wash buffer (1× TBS, 0.2% Tween 20, 3% BSA) which was used in all subsequent wash steps. Microarrays were incubated with primary antibody diluted 1:1000 or serum sample diluted 1:150 in probe buffer (1× TBS, 0.1% Tween 20, 3% BSA). After 1 hour incubation in primary antibody or sera, microarrays were washed and incubated 1 hour with Alexa Fluor® 647-conjugated secondary antibodies diluted 1:2000 in probe buffer. Microarrays were washed, and then rinsed with water before analysis.

Vaccinations and infections. Rhesus macaque sera were obtained from two separate vaccine studies for ZEBOV and MARV. The vaccine trials were similar in design and procedure to a study previously described by Warfield et al. (37). Briefly, for the ZEBOV study, five animals were vaccinated with ZEBOV virus-like particles (VLP) and MARV VLP. The vaccinated animals were subsequently challenged with ZEBOV. Three sera were collected for each animal: naïve, post-immunization, and post-challenge. The-Marburg virus study was conducted in a similar manner, except that the animals were vaccinated with MARV VLP and challenged with MARV.

Antibodies. Rabbit polyclonal anti-ZEBOV NP (anti-*Zaire*-NP, 0301-012), mouse monoclonal anti-SEBOV GP (anti-*Sudan*-GP, 0202-029), mouse monoclonal anti-SEBOV VP40 (anti-*Sudan*-VP40, 0202-018), mouse monoclonal anti-ZEBOV GP (anti-*Zaire*-GP, 0201-020), rabbit polyclonal anti-ZEBOV VP40 (anti-*Zaire*-VP40, 0301-010), mouse monoclonal anti-*Marburg virus* (Musoke) GP (anti-*Marburg*-GP, 0203-023), and mouse monoclonal anti-*Marburg virus* (Musoke) VP40 (anti-*Marburg*-VP40, 0203-012) antibodies were purchased from IBT Bioservices. Alexa Fluor® 647-conjugated goat anti-mouse IgG (A21237) and goat anti-rabbit IgG (A21244) antibodies were purchased from Life Technologies. Alexa Fluor® 647-conjugated rabbit anti-monkey IgG (bs-00335R-A647) and rabbit anti-monkey IgM (bs-0336R-A647) antibodies were purchased from Bioss (Woburn, Mass.).

Data acquisition and analysis. Processed slides were scanned at 635 nm wavelength using GenePix® 4400A (Molecular Devices, Sunnyvale, Calif.). Acquired images were analyzed with GenePix Pro 7 software. Any defective or missing spots were removed from further analysis. Median fluorescence intensity for each microarray spot was corrected through local background subtraction on GenePix Pro 7. Subsequent analysis was done in Microsoft Excel and R. The resulting background-corrected fluorescence intensities were averaged across replicate spots and quantile-normalized for each serum group (naïve, immunized, and challenged). A paired t-test was conducted to compare each antigen-antibody signals for naïve versus immunized, naïve versus challenged, and immunized versus challenged sera.

RESULTS

Filovirus protein microarray. Taking into consideration the complexity of the viral proteome and previous data suggesting potential targets of host antibody responses (14-16, 38), we developed a microarray comprised of a minimal set of proteins representative of all *Marburg* and *Ebola virus* species. The VP40 and NP for *Reston, Bundibugyo, Zaire, Sudan*, and *Taï Forest ebolovirus* and *Marburg marburgvirus* MARV were expressed as full-length recombinant proteins in *E. coli*. Initially, we prepared GP ectodomains (ΔTM) constructs from all filovirus species for expression in *E. coli*. However, because the GP ΔTM proteins were not all stable in solution, the coding sequences were truncated and expressed as more stable, GP mucin-like domain fragments (Table 1), with HisMBP fusion tags (amino-termini). The final GP protein design was supported by data from previous reports suggesting that antibody responses to ZEBOV were directed at least in part against the GP mucin-like domain (39-42).

Figure 1B:
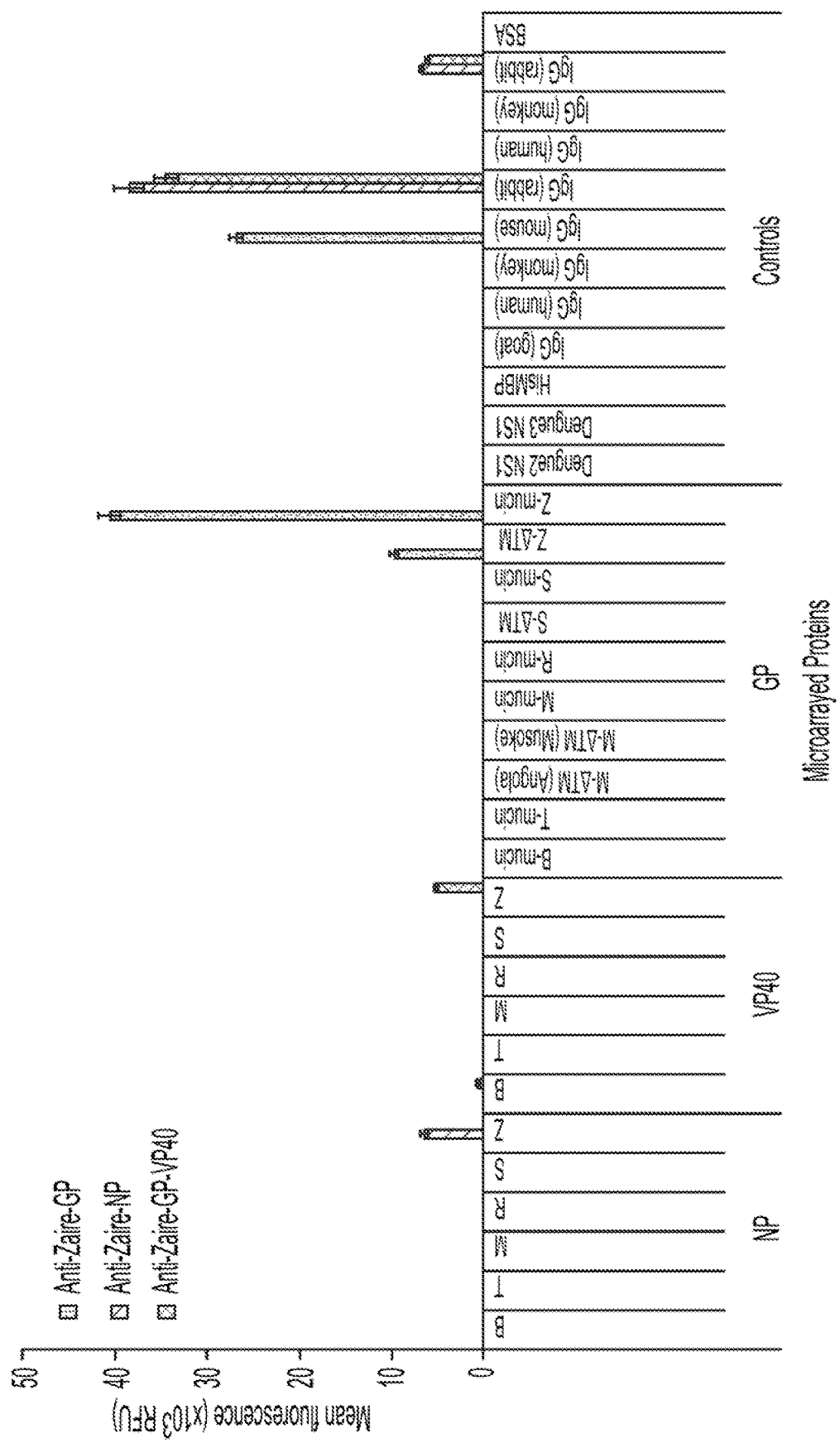
Figure 1C:
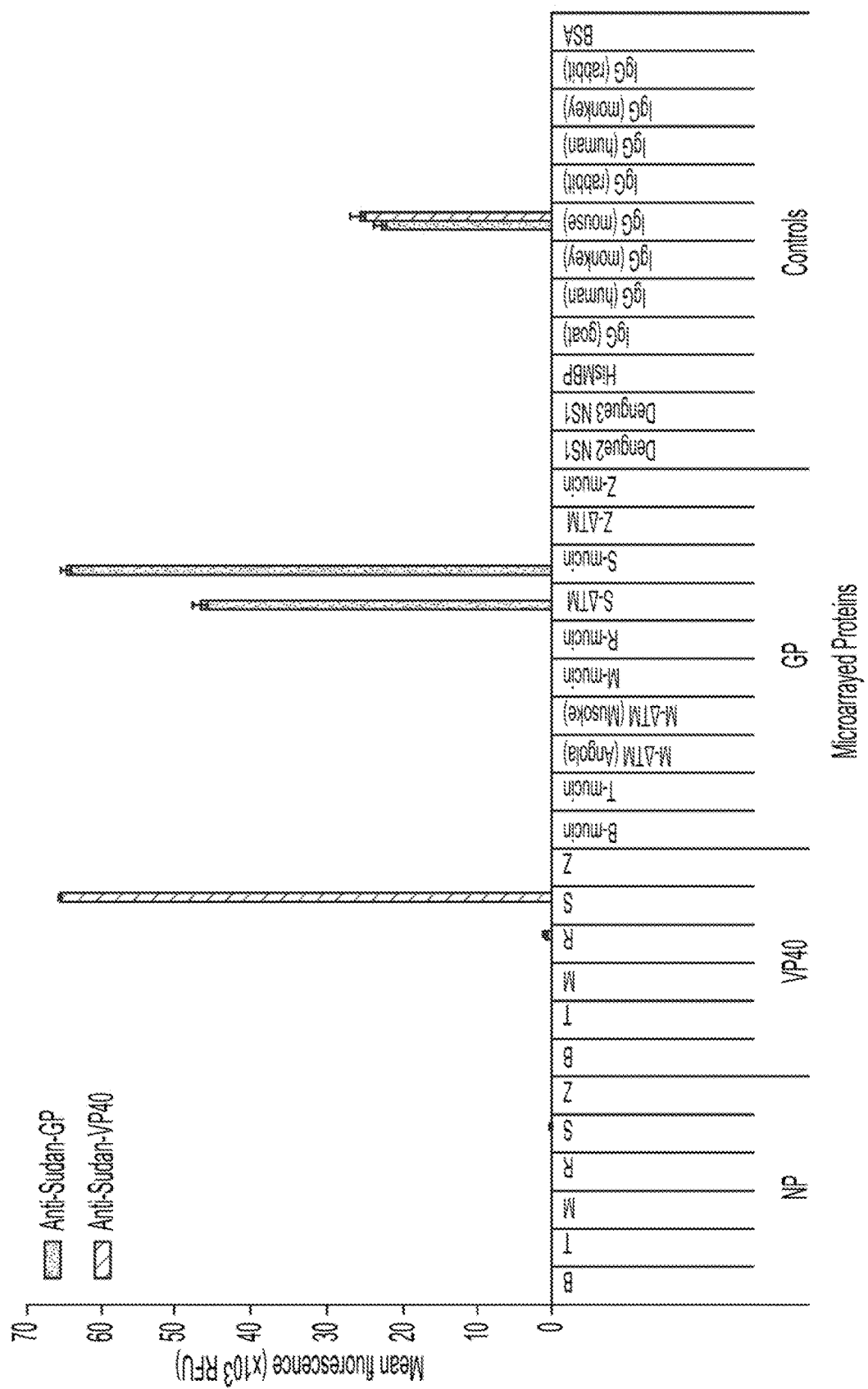

The recombinant filovirus antigens purified from *E. coli*, along with control proteins, were printed in 120-130 micron diameter spots in a 12×12 format (FIG. 4) on slides covered with a thin layer of nitrocellulose. Additionally, GP ΔTM produced in eukaryotic host cells were included in the microarray for comparison with the *E. coli*-produced GP-mucins. IgGs (monkey, human, rabbit goat, and mouse), IgMs (human, monkey, and rabbit), HisMBP, BSA, and dengue virus proteins served as controls. For quality control purposes and to validate our assay design, printed microarrays were probed with anti-His antibody as well as a panel of purified filovirus antibodies. Probing with anti-His antibody showed that all His-tagged proteins were successfully spotted and adsorbed onto the nitrocellulose-coated microarray slides (data not shown). Anti-*Marburg*-VP40, anti-*Marburg*-GP, anti-*Sudan*-VP40, anti-*Sudan*-GP, anti-*Zaire*-VP40, anti-*Zaire*-NP, and anti-*Zaire*-GP were bound by their target antigens with a high degree of specificity (FIG. 1A, B, C). Minor cross-reactivity between REBOV-VP40 and Sudan-VP40, and between BEBOV-VP40 and ZEBOV-VP40 were observed when microarrays were probed with anti-SEBOV-VP40 and anti-ZEBOV-VP40, respectively (FIG. 1B, C). Combined, data from these control antibodies indicate that the filovirus microarrays performed correctly under idealized test conditions.

Figure 5:
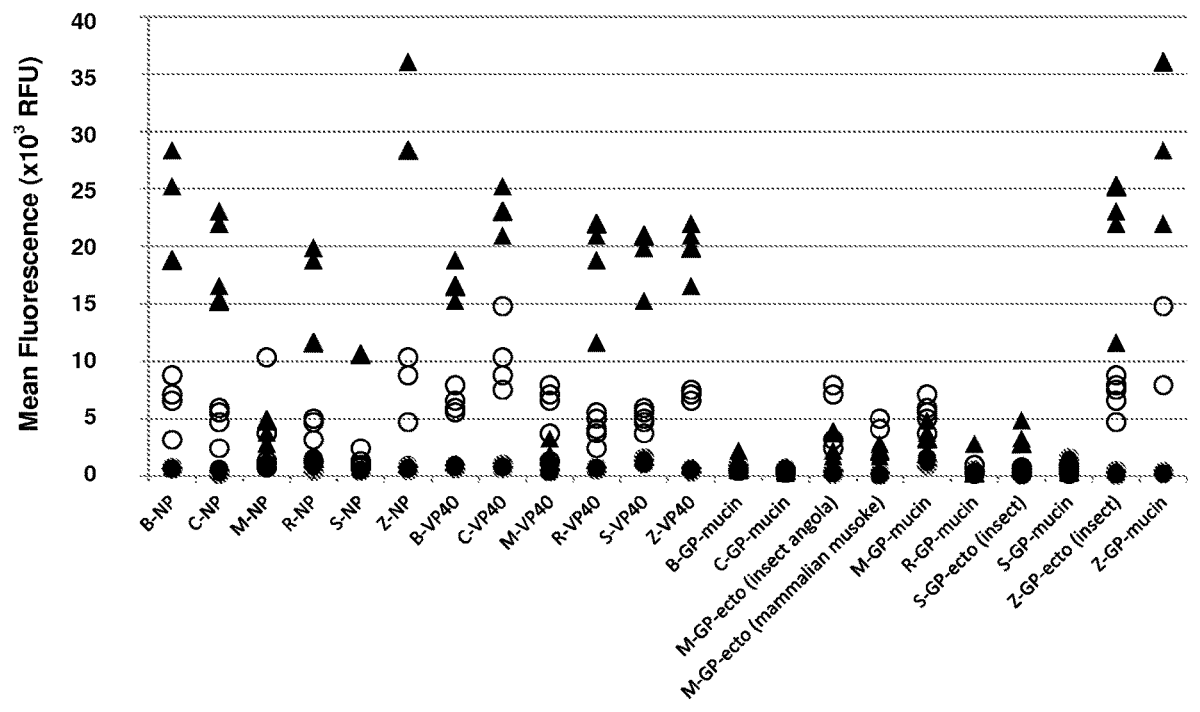
Figure 6:
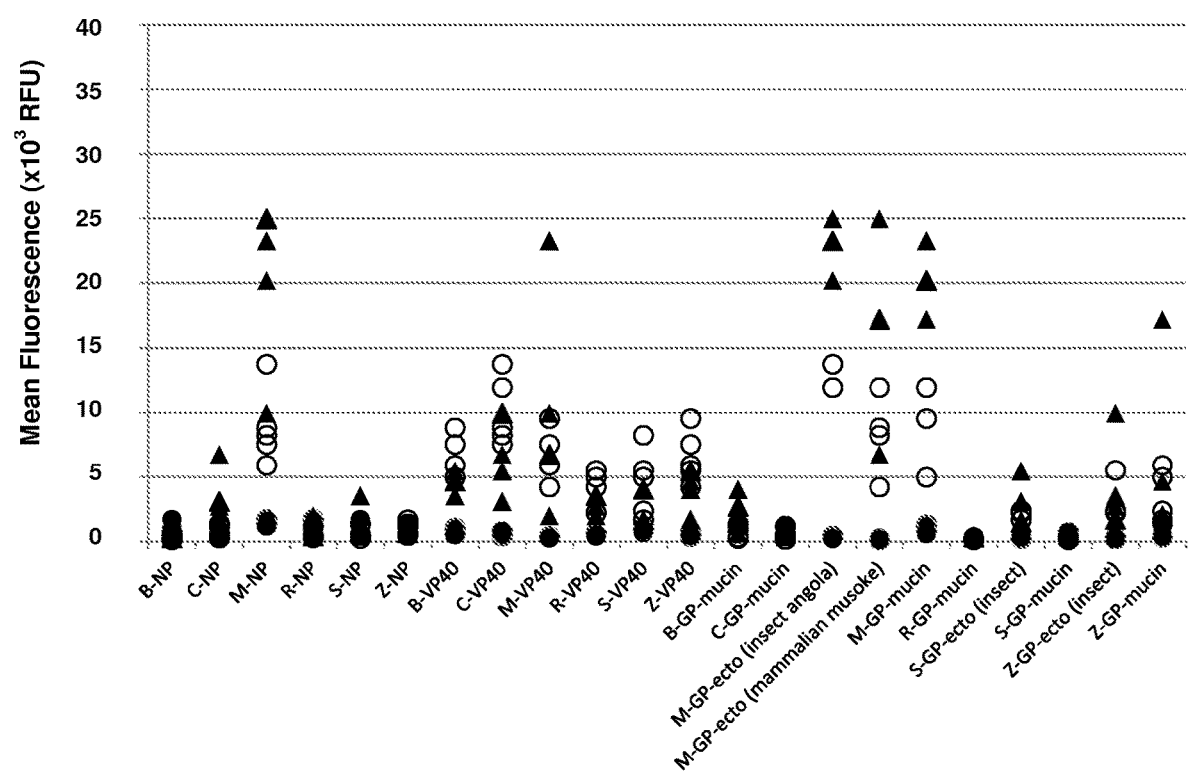

Analysis of sera from ZEBOV and MARV challenge studies. Sera from two separate animal studies were analyzed using our microarrays. In the ZEBOV study, rhesus macaques were vaccinated with a mixture of trivalent (GP, NP, and VP40) virus-like particles (VLP) for MARV and F and subsequently challenged with ZEBOV. In the *Marburg virus* study, rhesus macaques were vaccinated with trivalent (GP, NP, and VP40) VLP for MARV and subsequently challenged with MARV. All vaccinated animals in the *Zaire* and *Marburg* studies survived the viral challenge. After applying the serum samples to the filovirus microarray, bound IgG were detected using fluorescently-labeled secondary antibodies (FIGS. 5 and 6).

Figure 2A:
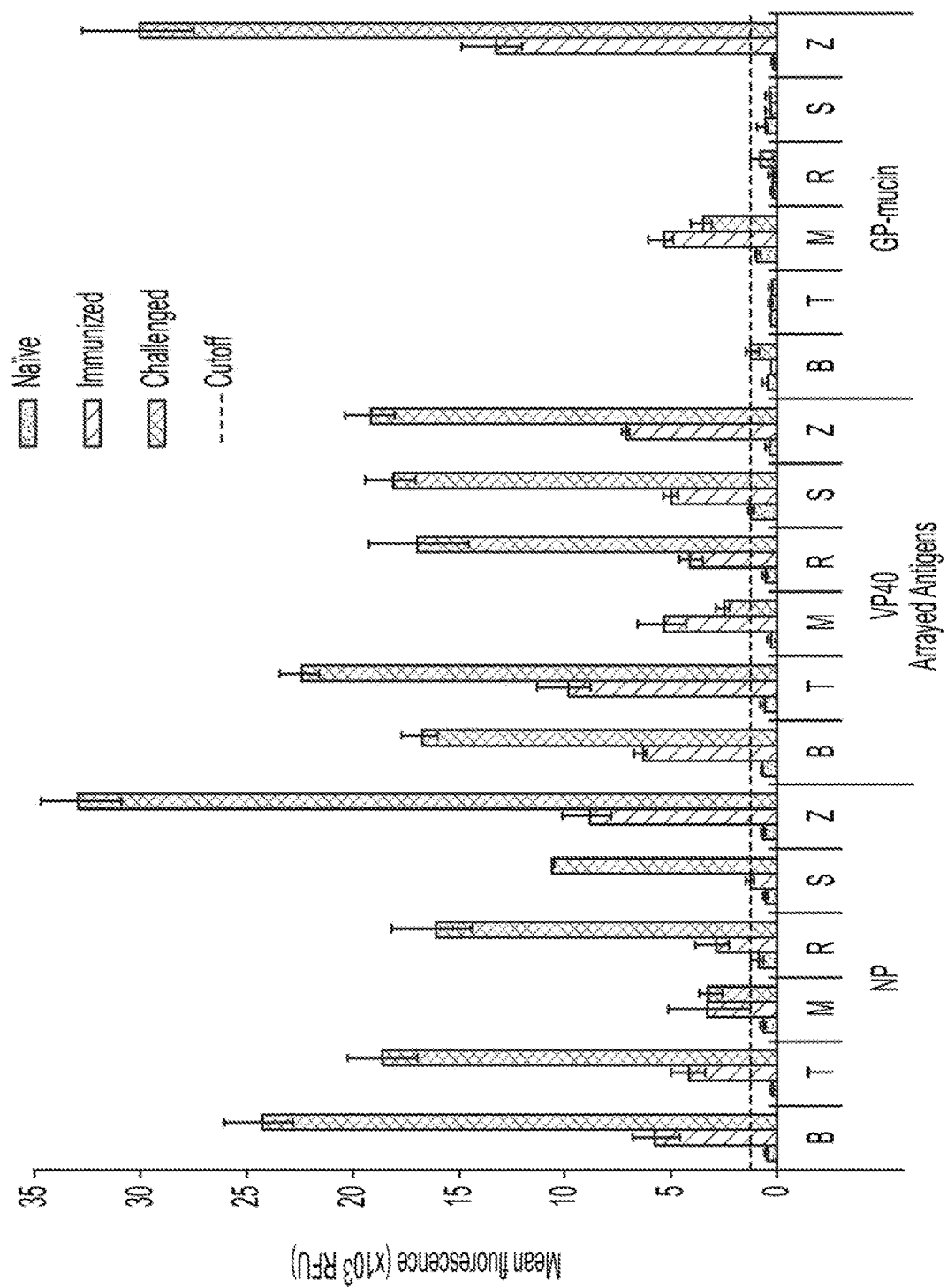
FIG. 2A-2C. IgG antibody response detected using filovirus microarray. Naïve, post-immunization (immunized), and post-viral challenge (challenged) sera from A) *Zaire ebolavirus* and B) *Marburg virus* animal studies were applied to assembled microarrays. Bound IgG antibodies were detected fluorescently on a microarray scanner. Following data pre-processing, normalized fluorescence signals were averaged across the five animals in each study. Bars represent normalized mean fluorescence (RFU)±SEM. The cutoff line represents two standard deviations above the mean antibody signal observed in naïve sera. For each antigen-antibody response, paired t-test was done for naïve versus immunized and naïve versus challenged sera. Unless indicated with an '*', all immunized and challenged samples above the cutoff line were found to have significant antibody increases (p<0.05) in comparison with the naïve samples. *Bundibugyo* (B), *Taï Forest* (T), *Marburg* (M), *Reston* (R), *Sudan* (S), and *Zaire* (Z). C) Side-by-side comparison of GP-specific IgG signals in challenged sera from *Zaire ebolavirus* and *Marburg marburgvirus* studies.
Figure 2B:
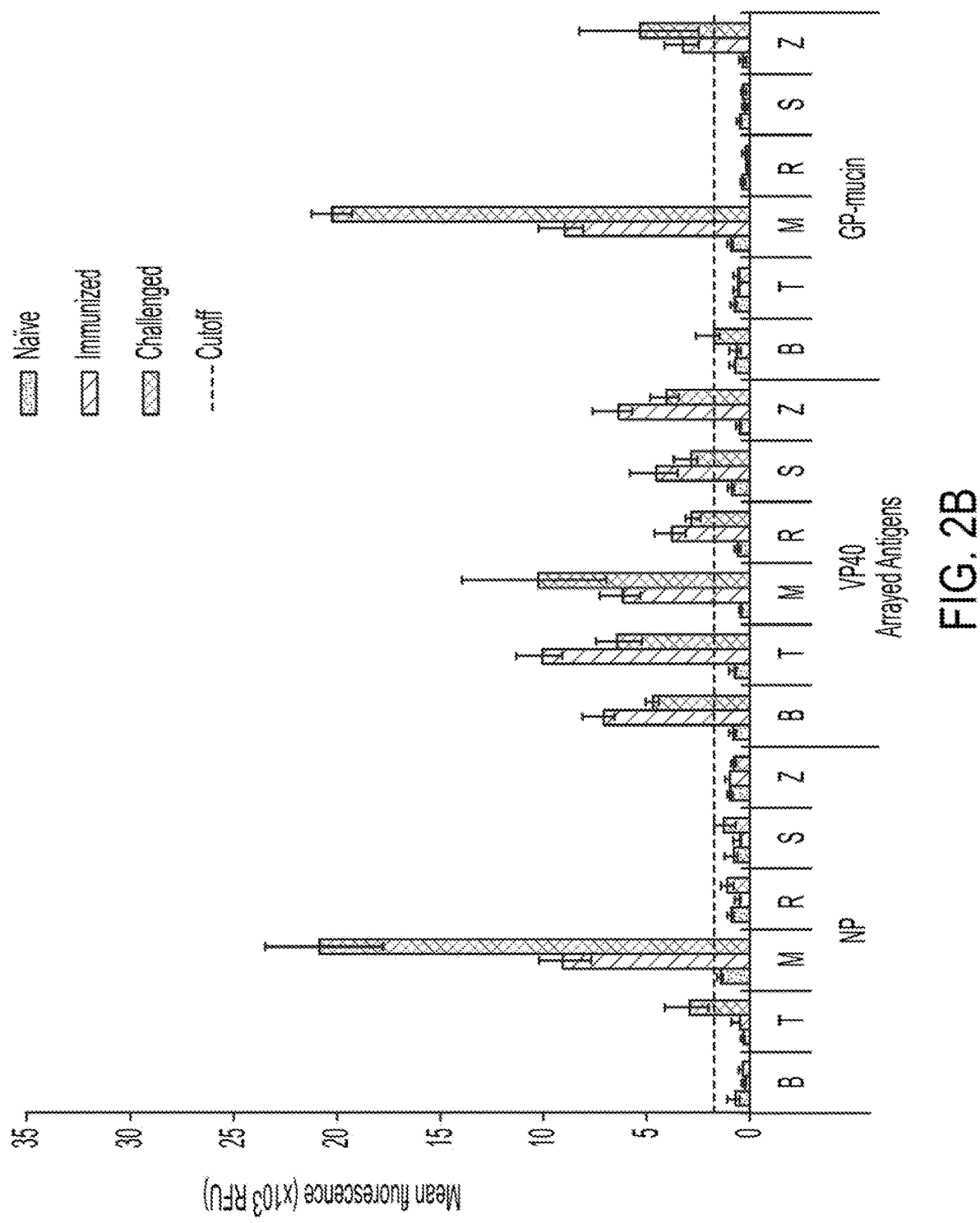
Figure 2C:
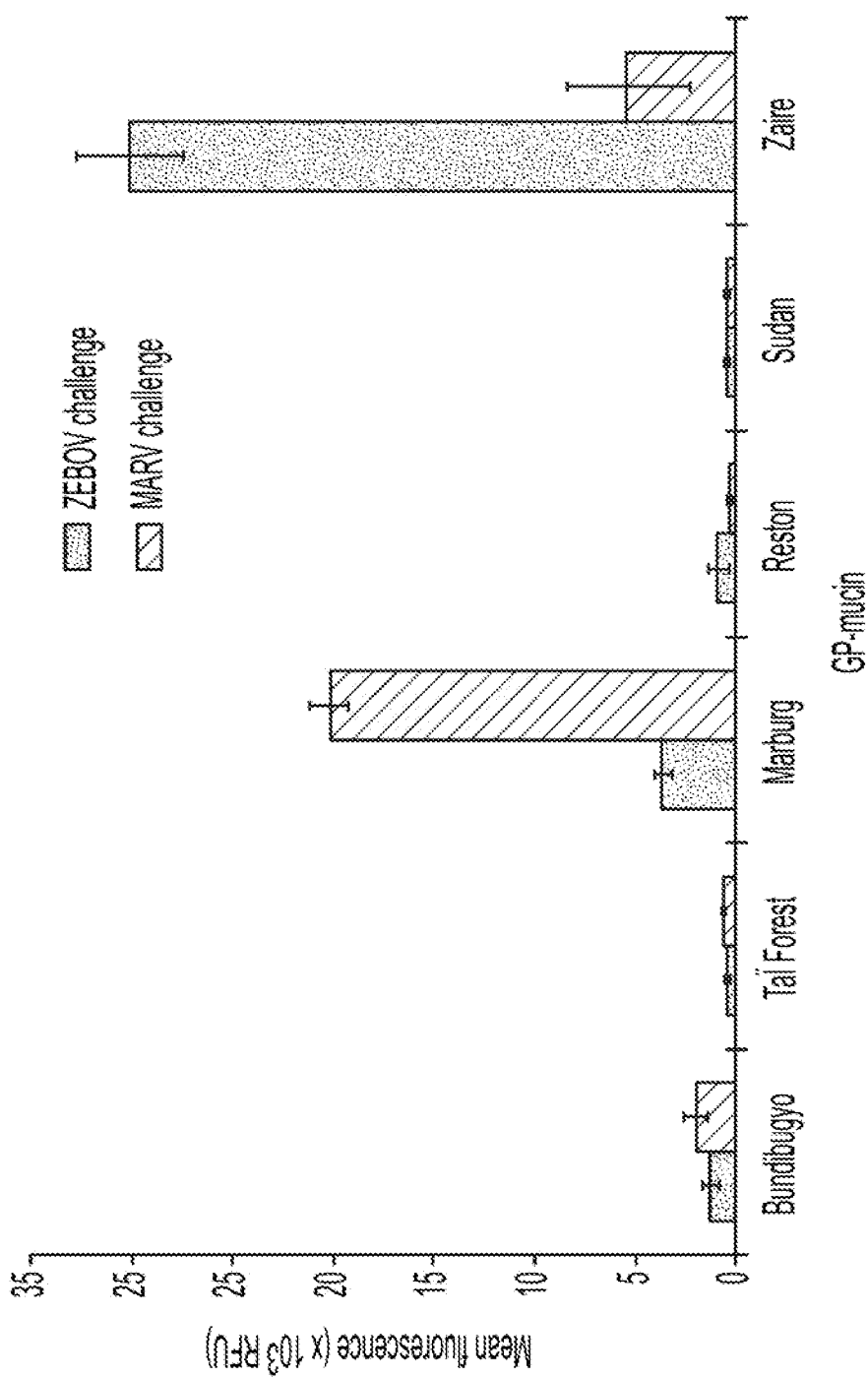

For the ZEBOV study, comparison between sera from naïve and immunized animals showed significant increases (p<0.05) in IgG against all vaccine antigens except for MARV NP (*Marburg*-NP) (FIG. 2A). Cross-reactive IgG against BEBOV, TAFV, REBOV, and SEBOV VP40, and BEBOV and TAFV NP were induced through vaccination (FIG. 2A). After animals were challenged, IgG signals against all *Ebola virus* NPs and VP40s and ZEBOV GP-mucin had significant increases (p<0.005) in challenged sera compared to immunized sera (FIG. 2A). For the *Marburg virus* study, the microarrays detected significant increases (p<0.05) in IgG against *Marburg*-NP, -GP-mucin, and -VP40 in immunized sera compared to naïve sera (FIG. 2B). Cross-reactive IgG against all *Ebola virus* VP40s were detected in the immunized sera (FIG. 2B). We observed a cross-reactive signal against *Zaire*-GP-mucin which was statistically significant (p<0.05) comparing naïve and immunized sera but not between naïve and challenged sera (FIG. 2B). Comparison between naïve and challenged sera showed significant increases (p<0.05) in IgG responses for *Marburg*-NP and -GP-mucin (FIG. 2B). However, the increase in IgG against *Marburg*-VP40 was not statistically significant (FIG. 2B). The results from analysis of rhesus sera suggested that the microarray enabled detection of anti-GP antibodies in a species-specific manner. Further, the anti-GP antibodies were detected with minimal cross-reactivity towards other species for the case of sera from the ZEBOV and MARV infections (FIG. 2C). We also examined IgM responses with sera from both animal studies, and representative data are provided in Supplementary FIG. 4. Overall, minor IgM signals were detected against ZEBOV and MARV antigens using these convalescent sera. The preliminary results indicate that the filovirus microarray may be used for IgM detection. Analysis of sera collected from time points closer to vaccination and viral challenge will confirm the utility of measuring IgM responses by protein microarray.

Figure 3A:
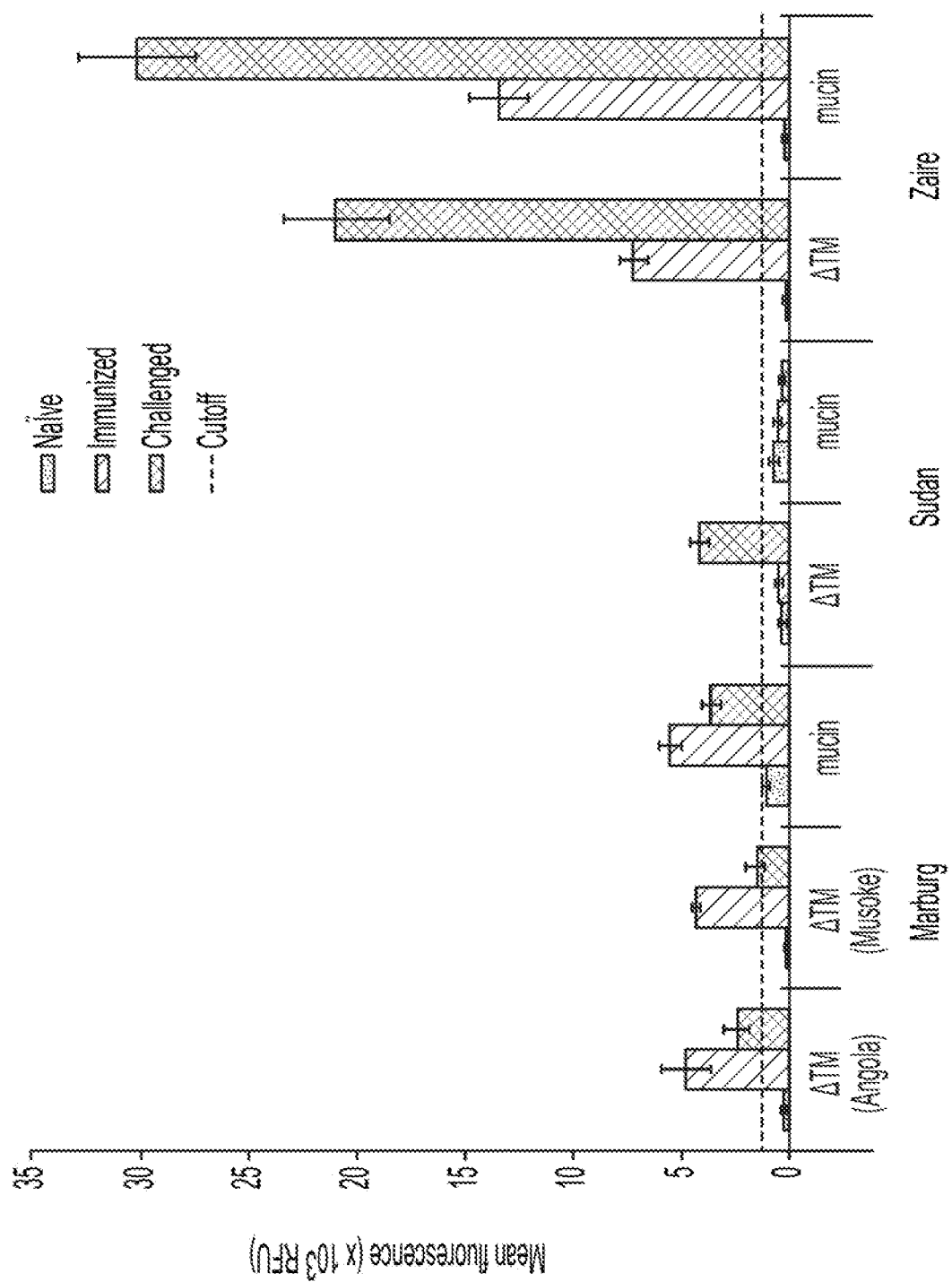
FIG. 3A-B. Comparison of antibody signals between *E. coli*- and eukaryotic cell-expressed GP. Data was acquired and analyzed in a similar manner as in FIG. 2. Bars represent normalized mean fluorescence (RFU)±SEM. All GP-mucins were expressed in *E. coli*. All GP ΔTM were expressed in insect cells except for *Marburg* GP ΔTM (Musoke) which was expressed in mammalian cells. A) *Zaire ebolavirus* study. B) *Marburg marburgvirus* study.
Figure 3B:
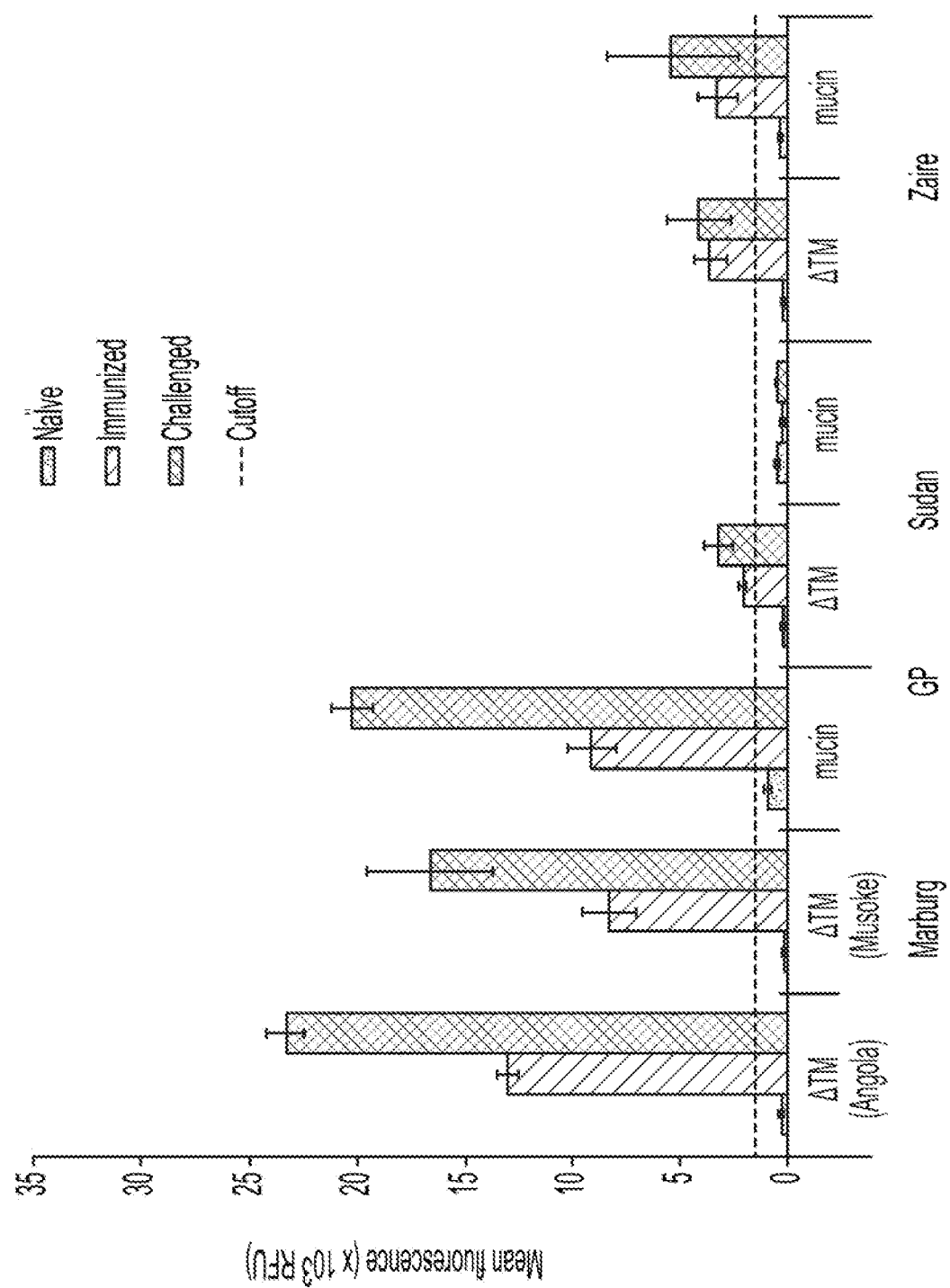

Comparison between *E. coli* and eukaryotic cell-expressed GP. Both the GP-mucins produced in *E. coli* and GP ΔTMs produced in eukaryotic cells (insect or mammalian) were included in the printed microarray. Examining sera from the ZEBOV (FIG. 3A) and MARV (FIG. 3B) studies, we confirmed that the mucin domain was sufficient for capturing IgG responses to filoviruses. We observed slightly higher IgG signals from the *Zaire* GP-mucin compared to *Zaire*-GP ΔTM with sera from ZEBOV challenged animals (FIG. 3A, B), whereas antibody recognition of the *Marburg* GP-mucin was comparable to the GP ΔTM *Marburg* (both Angola and Musoke) for sera obtained from animals challenged with MARV. Based on these microarray results, we concluded that the *E. coli*-produced GP-mucin resulted in similar species-specificity as the eukaryotic cell-expressed GP ΔTMs.

DISCUSSION

As the above example and data show, the compositions and methods disclosed herein, as demonstrated through one protein microarray embodiment provide for a platform that can identify and examine the antibody responses of mammals (e.g., rhesus macaques) to infection and vaccination (e.g., various species of *Ebola* and *Marburg viruses*). The illustrative florescence-based readout for the microarray shows that the assay and methods are highly sensitive, and only requires a minimal volume (1-2 microliters) of sample in order to provide a complete evaluation. While any number of amino acid sequences from one or more filovirus proteins may be used in connection with the detection agent and methods, the NP and GP antigens were very sensitive and could distinguish sera from ZEBOV in comparison to *Marburg virus* infection. The results from the *Marburg virus* study sera (*Marburg*-VP40) showed that some amino acid sequences can be associated with an amount of cross-reactivity to the VP40 antibody response against all *Ebola viruses*. Similarly, the results shown herein also were able to identify a general antibody cross-reactivity among *Ebola virus* NP and VP40 proteins, which is similar to results from previously reported ELISA studies (43-45). The data also identified that under these assay conditions, GP exhibited the highest level of antibody specificity. Further, and supporting the relevance of the GP-mucin domain as a serological marker of infection, *E. coli*-expressed GP-mucins for *Zaire* and *Marburg filoviruses* displayed similar species-specific antibody recognition as the multi-domain GPs (ΔTM) that were produced from eukaryotic cells, based on assay results from the ZEBOV and MARV studies. The microarray assay detected increases in IgG responses to specific filovirus antigens resulting from vaccination or viral challenge, and the relative levels of other antibody isotypes (IgM) could also be measured. We further noted that active infection stimulated a significant boost in immune responses primed by vaccination, as specific IgG levels in VLP-vaccinated macaques increased in response to aerosol challenges from either ZEBOV or MARV. The significant increase in ZEBOV and MARV-specific IgG following viral challenge, as measured by the protein microarray, shows that VLP vaccinations did not induce sterilizing immunity in the animals.

The results corroborate previously reported studies concerning antibody recognition of filovirus antigens. Antibody responses against NP and GP are detected in human patients by ELISA (14-16) and Western blots (46). Other reports have observed antibodies that recognize GP, NP, and VP40 in sera from a SEBOV (Gulu) outbreak in 2000-2001(38). However, these previous ELISA studies examined only select antigens from a single filovirus species or a single antigen from multiple filoviruses, whereas the microarray format supports a highly multiplex analysis of sera. By providing these Examples which demonstrate that more than one species of filovirus (e.g., two species of virus) can be examined and identified using the techniques and compositions disclosed herein, the disclosure provides for detection agents and methods (e.g., protein microarray) useful for multiplexed study of serological responses to most filovirus strains. The disclosure expands the capabilities of any previously described methods and compositions and facilitates diagnosis and serological surveillance of infections caused by multiple species of the highly infectious filoviruses. Further, providing for detection agents and methods that can be adapted into a low-cost, point-of-care assay greatly extends the utility of the technology, (e.g., relative to the prior methods and techniques requiring full laboratory facilities).

Management and patient care for typical filoviral infections provide significant challenges given the usually resource-poor settings of outbreaks and the procedures that are required to prevent spread of infections (47). Allaranga and coworkers proposed that an active epidemiological surveillance system, including surveillance of zoonotic infections, is vital for early detection and effective response to filoviral hemorrhagic fever epidemics in Africa (48). A recent report of hospital-based surveillance in Ghana identifies the importance of distinguishing infections caused by hepatitis viruses that produce symptoms that mimic viral hemorrhagic fevers from the infrequent infections caused by filoviruses (49). Further, the prevailing hypothesis concerning outbreaks of filoviral hemorrhagic fevers is that indigenous human populations occasionally make contact with animal reservoirs of *Ebola* and *Marburg viruses*, resulting in rapid spread of disease (Mbonye et al, 2013). Wildlife are often more severely affected than humans, as demonstrated by a 89% drop in chimpanzees and 50% decrease in gorilla populations as a result of one recorded *Ebola virus* outbreak (50). Thus, the disclosure provides compositions and assay methods that can be incorporated as a vital tool for such epidemiological studies and for eventual diagnosis of infections, including supporting serological surveillance of infections occurring within domestic or wildlife animal populations.

EXAMPLE 2

This example illustrates the specificity of antibody responses with sera collected from survivors of three separate Ugandan outbreaks that were caused by *Marburg marburgvirus* (MARV) in Kabale, *Bundibugyo ebolavirus*, (BDBV) in *Bundibugyo*, and *Sudan ebolavirus* (SUDV) in the Gulu district. Control samples collected from the same geographical regions as the disease outbreaks were also included in the study. To measure antibody responses, we assembled a protein microarray that displayed nucleoprotein (NP), varion protein 40 (VP40), and glycoprotein (GP) antigens from isolates representing the six species of filoviruses. Analysis of the microarray data by hierarchical clustering revealed clear positive signals from all infection samples, which were readily distinguishable from negative controls. The amino acid sequences of GP are most diverse among species, whereas NP sequences are highly conserved. Consistent with protein similarities, NP was most cross-reactive and exhibited the highest level of antibody responses, while antibody responses to GP were the most specific. Persistent antibody levels to GP, NP and VP40 were observed for Gulu SUDV survivors 14 years after infection. Significant antibody responses to autologous antigens were observed for all three outbreak cohorts. The MARV survivors presented the lowest level of antibody cross-reactivity with proteins from heterologous filoviruses, while the SUDV survivors exhibited the highest cross-reactivity with other filoviral proteins. Our results suggest that survival from infection caused by one species of filovirus may impart at least partial immunity to other outbreaks.

Methods:

*Ebola* and *Marburg* Survivor Sera

Our study included a total of 59 serum samples from patients who survived infections caused by SUDV-Gulu, BDBV-*Bundibugyo* and MARV-Kabale outbreaks along with controls from subjects living in the same location who were not infected with the virus. The survivors received uniform treatment after admission to a hospital. Institutional approvals for the study were obtained from the Uganda Virus Research Institute in Entebbe, Uganda, Ugandan National Council for Science and Technology and United States Army Medical Research Institute of Infectious Diseases (USAMRIID). A signed consent form and a personal health questionnaire were obtained from each subject. A serum sample from a human subject who was vaccinated with a recombinant adenovirus serotype 5 (rAd5) expressing EBOV and SUDV GP was also included in the study (Ledgerwood, Costner et al. 2010).

Sequence and Phyologeny Analysis

Three multiple sequence alignments (MSAs) were generated for the amino acid sequences of NP and GP mucin-like domains of *Ebolavirus* and *Marburgvirus* strains, using CLUSTAL W2 (Larkin, Blackshields et al. 2007). Each MSA had a different gap opening penalty (5, 10, and 25), with Blosum62 as the protein weight matrix and all other options left as default. T-Coffee Combine (Notredame, Higgins et al. 2000, Di Tommaso, Moretti et al. 2011) was then used to generate a single alignment that had the best agreement of all three MSAs for each protein. The combined alignments of full-length NP and GP mucin-like domain sequences were used to calculate Shannon entropy per column of the aligned sequences as a measure of amino acid variability and to generate percent identity matrices in BioEdit Sequence Alignment Editor v7.1.3.0 (Hall 1999). To eliminate poorly aligned positions and divergent regions in the combined alignments, each alignment was filtered using Gblocks (Castresana 2000, Talavera and Castresana 2007) with strict settings (no gap positions within the final blocks, strict flanking positions, and no small final blocks). Gblocks identified a 406 residue conserved region at the N-terminus of NP, which was used for phylogenic reconstruction (BDBV, TAFV, RESTV, SUDV, EBOV-residues 20-425; MARV-residues 2-407). Due to a high degree of heterogeneity among individual residues, conserved regions within GP mucin-like domain sequences could not be identified. For this reason, an ungapped, highly variable region of 33 residues at the N-terminal portion of the GP moiety was selected for use in phylogenic reconstruction (BDBV, TAFV, RESTV-residues 2-34; EBOV and MARV-residues 1-33). Phylogenic trees were generated using the maximum likelihood method implemented in the PhyML program (v3.0 aLRT) (Guindon, Dufayard et al. 2010). The Blosum62 substitution model was selected and 4 gamma-distributed rate categories to account for rate heterogeneity across sites. The gamma shape parameter was estimated directly from the data ($\alpha_{NP}$=0.654, $\alpha_{GPmucin}$=15.371). Tree topology and branch length were optimized for the starting tree with subtree pruning and regrafting (SPR) selected for tree improvement. Reliability for internal branches was assessed using a bootstrap method with 1000 replicates. Comparison of phylogenetic trees was completed using Compare2Trees software available online (Nye, Lio et al. 2006).

Microarray Proteins

Recombinant proteins from filoviruses were cloned, and the GP-mucin, NP and VP40 were expressed in *E. coli*, while the GPΔTM proteins were produced in insect or mammalian expression systems as previously described (Kamata, Natesan et al. 2014). The GPΔTM for BDBV, SUDV (Boniface), *Zaire Ebola virus* (EBOV-Mayinga), *Reston Ebola virus* (RESTV-*Reston*), and MARV (Angola) were produced in insect cells; while BDBV, RESTV (Pennsylvania), *Tai Forest Ebola virus* (TAFV), SUDV (Boniface), EBOV (Mayinga), and MARV (Musoke) GPΔTM were expressed in mammalian cells. The *Ebola* GP-mucins were purified using HisTrap HP columns and MARV GP-mucin was purified using MBPTrap HP column. The NPs were purified by on-column refolding on HisTrap HP columns as described previously (Kamata, Natesan et al. 2014). The purity and concentrations of the proteins were determined by microfluidic assays (Agilent Technologies, Santa Clara, Calif.). The dengue virus proteins were previously described (Fernandez, Cisney et al. 2011).

Multiplexed Protein Microarray

The recombinant proteins were spotted (140 μm diameter) in a 10×36 microarray on FAST® slides (Kerafast, Boston, Mass.) by using a Marathon inkjet microarrayer (ArrayJet, Edinburgh, Scotland, UK). The array included a total of 41 proteins: i) *E. coli*-expressed filoviral antigens; ii) Sf9-expressed GPΔTM from MARV, EBOV, SUDV, BDBV and RESTV (IBT Bioservices); iii) mammalian cell-expressed GPΔTM from from all six species of Filoviridae iv) human, monkey, mouse, rabbit, and goat IgG (Rockland Immunochemicals, Gilbertsville, Pa.); v) HisMBP (ProteinOne, Rockville, Md.); iv) human, monkey, and rabbit IgM (Rockland Immunochemicals) and vi) dengue virus serotype 2, 3 nonstructural protein 1 (NS1); and vi) BSA (Thermo Fisher Scientific, Grand Island, N.Y.). The expression and purification of the dengue virus proteins was previously described (Fernandez, Cisney et al. 2011). Each protein in the microarray was printed in quadruplicate. All purified proteins were diluted to 200 ng/μL and prepared in a final concentration of 50% glycerol in printing buffer consisting of 25 mM HEPES, 0.5 M NaCl, and 1 mM dithiothreitol (DTT). Alexa647®-conjugated streptavidin (Life Technologies) was diluted 1:50 in 1× PBS with 50% glycerol and included in fixed positions within the array as a spatial reference marker. The recombinant proteins were physically characterized to confirm correct molecular weight and purity (70-95%; data not shown). Quality control of printed microarrays was confirmed with specific antibodies against poly-His tags, *Marburg* VP40, *Marburg* GP, *Sudan* VP40, *Sudan* GP, anti-*Zaire* VP40, *Zaire* NP and *Zaire* GP, as described previously (Kamata and Natesan, 2014). The printed and dried microarrays were stored under vacuum (−20° C.).

Analysis of Antibody Interactions

A Tecan HS Pro400 (Tecan US, Morrisville, N.C.) hybridization station was used for most of the microarray processing steps, and all manipulations were performed at 22° C. The printed microarray slides were incubated for 1 hour in blocking buffer (1× Biacore Flexchip, GE Healthcare) with 2% normal goat serum (Vector Laboratories). The microarray slides were washed (3 times; 5 minute each) with a buffer (1× TBS, 0.2% Tween 20, 3% BSA) that was used in all subsequent wash steps. Human sera diluted 1:150 in probe buffer (1× TBS) were incubated (1 hour) on the microarray surface. The slides were washed and incubated for 1 hour with Alexa®647-conjugated secondary antibodies diluted 1:2000 in probe buffer. The slides were rinsed with water and dried before acquiring data.

Data Acquisition and Analysis

Processed slides were scanned at 635 nm wavelength using a GenePix® 4400A (Molecular Devices, Sunnyvale, Calif.), with PMT gain set to 400 and laser power set to 10%. Acquired images were analyzed using GenPix Pro 7 software (Molecular Devices). Background median fluorescence intensity was subtracted from median fluorescence intensity of each spot, and the resulting background-corrected fluorescence intensity was averaged across the quadruplicates. The calculated mean fluorescence was used for further analysis. The data were quantile normalized using the preprocess core package of R. Background correction, standard Z-score normalization to compare each signal to that of all signals, and M—statistics were with performed with ProtoArray Prospector software (Life Technologies), as described previously (Keasey, Schmid et al. 2009). Group comparisons between control and survivors were performed with thresholds of normalized signals of at least 500 relative florescence units (RFUs), and a minimal signal difference of 200 RFU between two groups. Heat maps of normalized and log 2-transformed values were created using GENE-E (Broad Institute, Cambridge, Mass.). Hierarchical clustering by average linkage Euclidean distance was used to examine overall patterns of antibody interactions.

Results

Amino Acid Sequence Diversity of Filovirus Proteins

Figure 8:
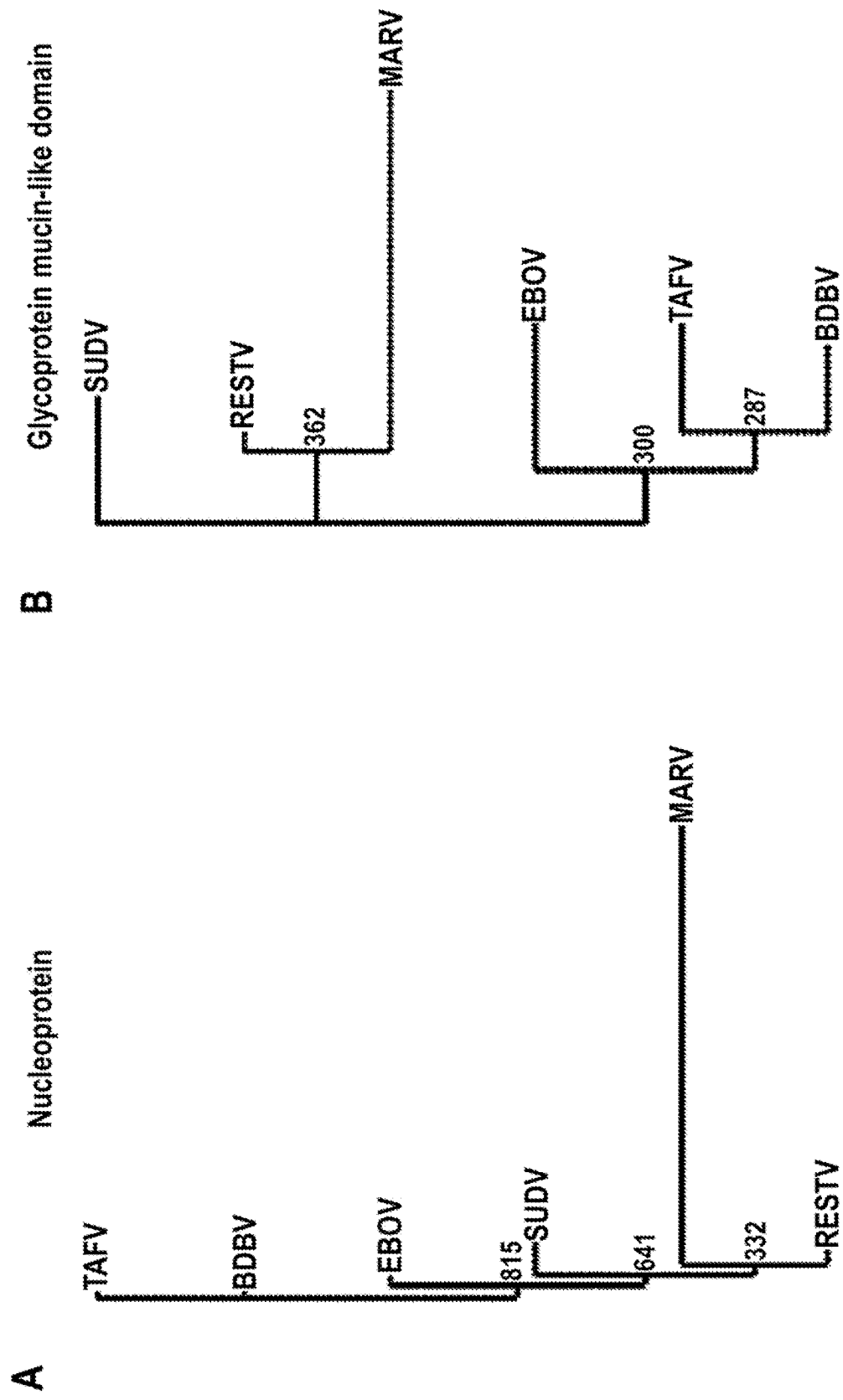
FIG. 8A-C. Phylogenic relationships between filovirus strains based on amino acid sequences of NP and GP mucin-like domain. Separate dendrograms representative of sequence similarity between filovirus strains were derived based on amino acid sequences of A) a conserved region of 406 residues of NP (BDBV, TAFV, RESTV, SUDV, EBOV-residues 20-425; MARV-residues 2-407), and B) the highly unconserved mucin-like domain of GP, consisting of 33 residues at the N-terminus of the domain region (BDBV, TAFV, RESTV-residues 2-34; EBOV and MARV-residues 1-33). Maximum likelihood tress are shown with bootstrap values (out of 1000 replicates) shown at internal nodes. C) Sequence identity matrix comparison of filovirus NP and GP mucin-like domain amino acid sequences. Full length sequences of NP and the GP mucin-like domain were used to generate percent identity matrices. NP (light grey, upper triangle) is highly conserved among *ebolavirus* strains and more divergent from MARV, while the GP mucin-like domain is highly variable and exhibits minimal sequence identify among all filovirus strains examined.

To examine human antibody responses to filovirus infections we first considered the selection of protein probes to include in our analysis. We performed a phylogenic analysis of filoviral proteins (FIG. 8) to identify highly conserved probes as well as proteins that may provide an antibody response signature that was unique to each species of virus. As demonstrated in FIG. 8, NP is highly conserved among *ebolaviruses* (>60% sequence identity), while NP from MARV shares only 30% sequence identity with *ebolavirus* species (FIG. 8*c*). Approximately 400 amino acids of the N-terminal portion of NP that showed a higher degree of similarity among *ebolavirus* strains and MARV (Keasey, unpublished data; (Sanchez, Kiley et al. 1992), was selected for phylogenic inference (FIG. 8*a*). The small shape parameter value ($\alpha_{NP}$=0.654) of the gamma distribution used for construction of the dendrogram based on NP sequences indicated that there was a relatively large amount of rate variation, with many sites evolving very slowly and select sites evolving at a high rate (Lio and Goldman 1998). Thirty percent of NP residues (216 residues out of 739 total) were completely conserved among the six strains examined, with an average variability/residue=0.638 (data not shown), based on Shannon entropy calculations per residue of the NP MSA. In contrast, the mucin-like domain of GP exhibited minimal sequence identity among all filovirus strains examined (sequence identity=5-26%, 8). Phylogenic inference was based on only a 33 residue region at the N-terminus of the domain (FIG. 8*b*), due to the fact that this was the only ungapped portion of the multiple sequence alignment. The shape parameter of the gamma distribution ($\alpha_{GPmucin}$=15.371) for GP-mucin sequences was much larger than that of NP sequences, indicating that most sights have roughly similar rates of substitution (Lio and Goldman 1998). No residues within the mucin-like domain were completely conserved, and the average variability per residue was 50% greater than that of NP sequences (H/res=1.07). Further, the MARV GP mucin-like domain sequence is 225 residues in length versus 153 residues for *ebolavirus* strains.

We measured topological features among filovirus strains based on amino acid sequences of NP and GP-mucin (Compare2Trees software tool), (Nye, Lio et al. 2006). Comparison of phylogenic trees (FIG. 8 a, b) reveals a similar topology for NP and GP-mucin, despite extensive sequence diversity among individual proteins. The overall similarity between the two trees was found to be 77.8%, with BDBV, TAFV, EBOV edges being 100% conserved between trees, and SUDV, RESTV, and MARV edges exhibiting 66.7% similarity. The long branch length of MARV separated this lineage of filoviruses from all *ebolavirus* species.

Human Antibody Reponses to Filoviral Proteins

The study involved a total of 37 survivors from the 2000 SUDV-Gulu outbreak, 20 samples from 2007 BDBV-*Bundibugyo* outbreak, and 2 samples from MARV-Kabale outbreak (Table 2). The sera samples were collected from a year after outbreak for MARV-Kabale, seven years later for BDBV-*Bundibugyo*, and twelve to fourteen years after for SUDV-Gulu. Sera collected from non-infected individuals living in the same geographical region of each outbreak, normal healthy volunteers from the United States, and serum from a subject vaccinated with a replication defective rAd5 vaccine expressing GP antigens in a 1:1 ratio from EBOV of *Zaire* strain and SUDV of Gulu strain (Ledgerwood, Costner et al. 2010) were included as controls. To examine antibody interactions, dilutions of each serum were incubated on the surface of the protein microarray, which included eleven GPΔTM proteins produced by eukaryotic cell expression, eighteen proteins (GP-mucin, NP and VP40 from six species) expressed in *E. coli* (Table 3).

TABLE 2

Summary of sample used in the study

| Location | Species | Year of Outbreak | Year of Collection | No. of Samples | No. of Controls |
|---|---|---|---|---|---|
| Gulu (Uganda) | SUDV | 2000 | 2012/2014 | 37 | 4 |
| Bundibugyo (Uganda) | BDBV | 2007 | 2014 | 20 | 3 |
| Kabale (Uganda) | MARV | 2012 | 2013 | 2 | — |
| USE-NIAID rAd5 vector vaccine | EBOV SUDV (GP) | — | — | 1 | 5 |

Figure 9:
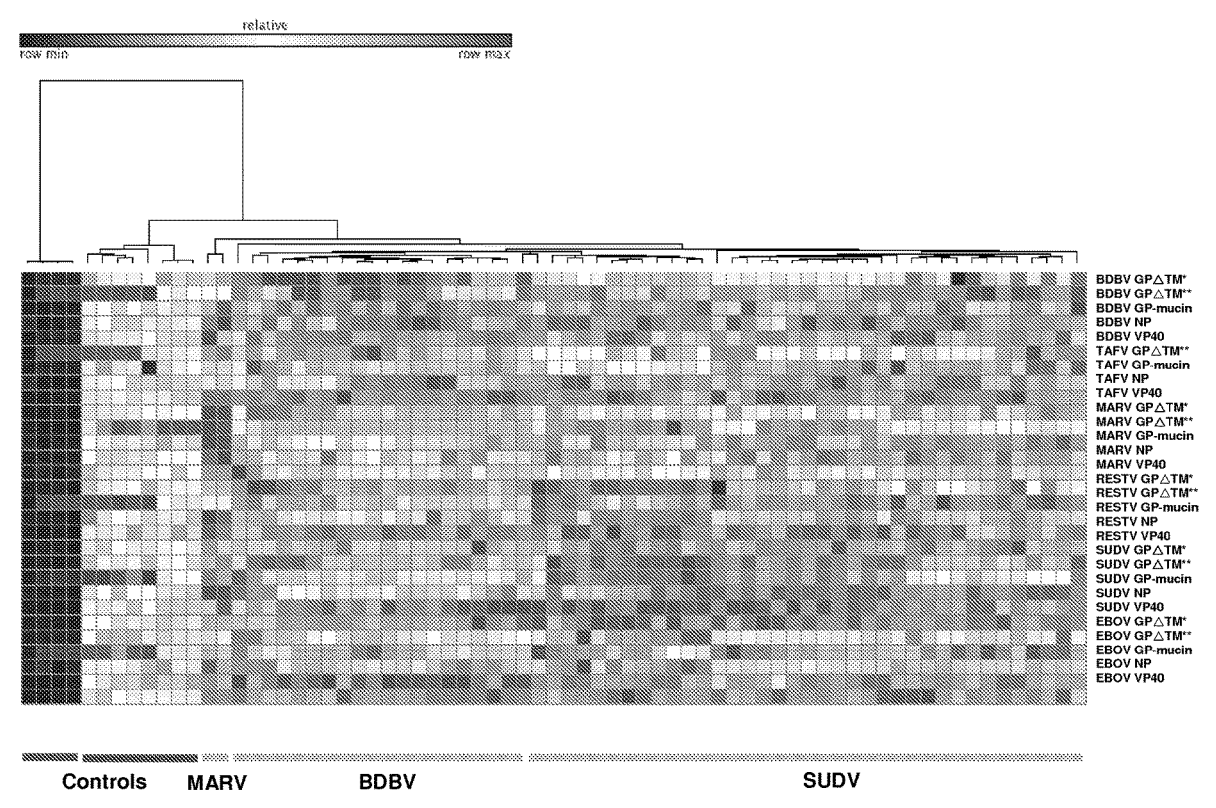
Figure 10:
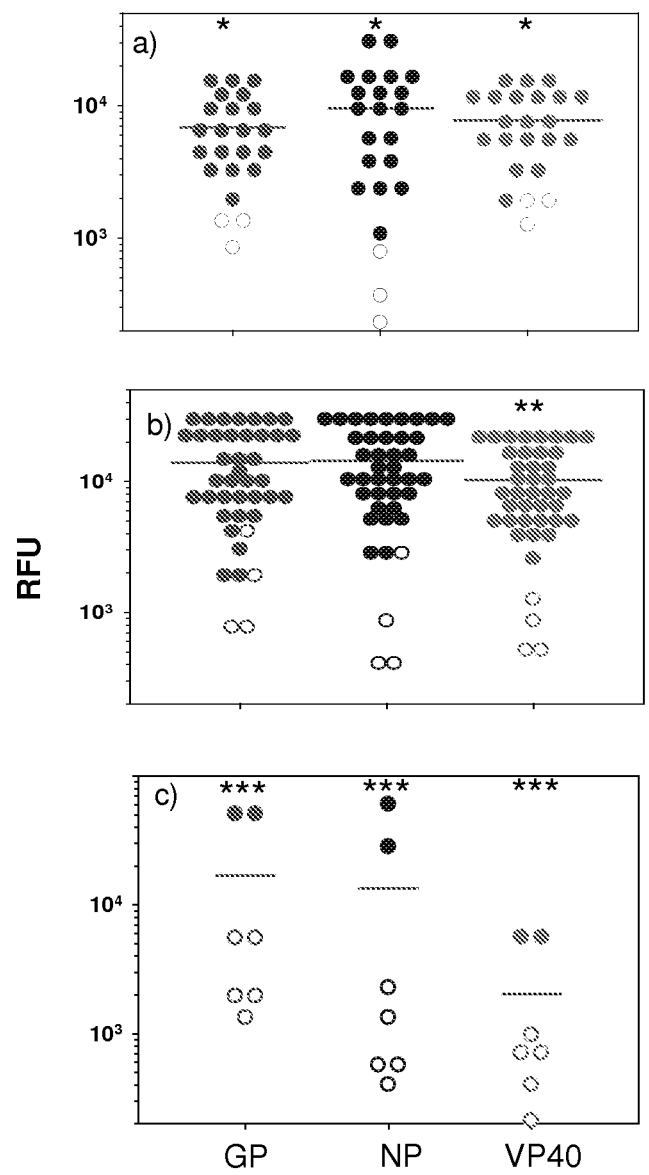
FIG. 10. *Ebola* and *Marburg* survivors convalescent IgG responses to autologous GP-mucin, NP and VP40 recombinant proteins. Panel a shows reactivity to BDBV, panel b to SUDV-Gulu and panel c to MARV antigens by survivors. The filled circles denote survivors and open circles controls. Each circle corresponds to individual sera sample and the red line represents geometric mean of all samples in each group. Statistical analysis was performed using Prospector software for comparing survivor Vs. controls. Significant differences between the two groups in terms of p values are shown as *p,0.05, p,0.01, *p,0.001

A heat map showing the analysis of all serological immune responses to the filovirus proteome is illustrated in FIG. 9. Hierarchical clustering (unsupervised) of the data by Euclidean distance indicated that the human sera was organized into two major clusters corresponding to infected and uninfected (negative) control groups (FIG. 9). Within the negative control group, the non-African, BDBV negative controls, and SUDV negative samples clustered separately (FIG. 9). The non-African control sera exhibited no antibody interactions with the filoviral proteins, while sera collected in Uganda showed some but not significant binding to filoviral proteins. The MARV, BDBV and SUDV convalescent samples clustered as distinct groups within the infected sample group (FIG. 9), indicating that the IgG signals from our microarrays can be used to distinguish between MARV, BDBV and SUDV-infected sera. The convalescent samples from all MARV, BDBV, and SUDV showed strong reactivity towards autologous antigens (FIG. 10). The MARV group showed significant increases against autologous GP-mucin ($p<0.001$), GPΔTM (insect, $p<0.001$), NP ($p<0.001$) and VP40 ($p<0.001$) when compared to negative controls. Significant reactivity was seen for BDBV sera samples against BDBV antigens GP-Mucin ($p<0.05$), GPΔTM (insect, $p<0.05$), NP ($p>0.05$) and VP40 ($p<0.05$). Similarly, the SUDV sera samples showed significant increases in antibody binding to SUDV GPΔTM (insect, $p<0.05$) and NP ($p<0.005$). However, the increase against SUDV VP40 was not statistically significant (Table 2). For the case of the rAd5-vaccinated individual, a robust antibody response was observed against EBOV GPΔTM (mammalian) but not against SUDV GP (Supplementary Figure). The recombinant rAd5 vaccine expressed EBOV and SUDV GP proteins, and most vaccinees produced antibodies against both proteins, as detected by ELISA (Ledgerwood, Costner et al. 2010).

Figure 11:
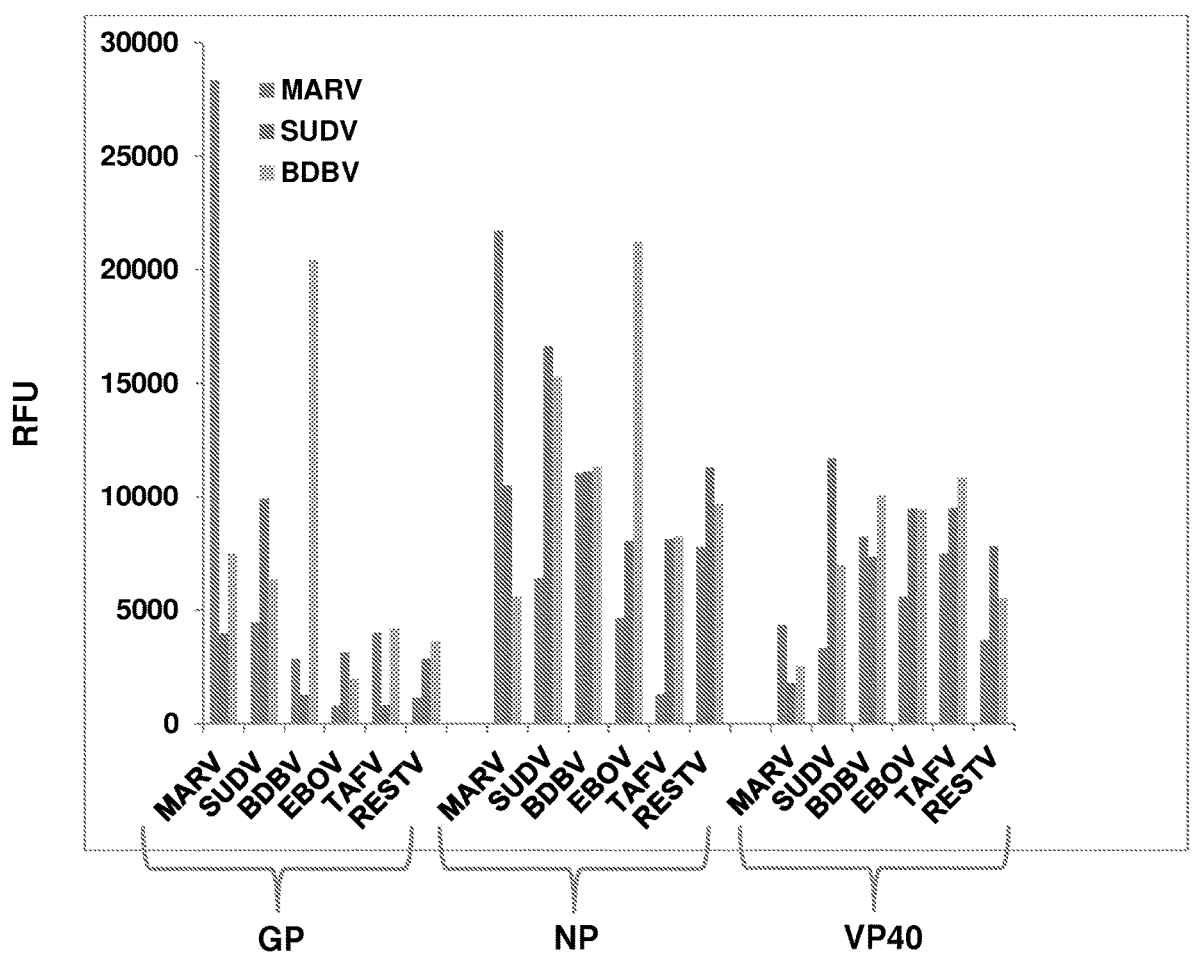
FIG. 11. Survivor sera antibody cross-reactivity to filoviral heterologous compared to autologous antigens. Each bar represents the mean antibody binding of all samples in a survivor group (MARV, SUDV or BDBV) expressed as relative fluorescence units (RFU).

We examined the cross-reactivity of the Ebola and Marburg convalescent sera against heterologous antigens (FIG. 11). Comparing all survivor sera, antibodies from the MARV infection cases were the least cross reactive with ebolavirus GPΔTM antigens, while only the BDBV-GP mucin interacted significantly ($p<0.005$) with MARV convalescent serum antibodies. The MARV sera did cross-react with other heterologous antigens, but to a much lower extent than BDBV and SUDV survivors. The SUDV sera exhibited significant levels of antibodies against RESTV GPΔTM (insect, $p<0.05$), RESTV NP ($p<0.05$), and TAFV NP ($p<0.05$). The BDBV presented the highest cross reactivity among filovirus antigens. Significant antibody binding was observed with EBOV NP ($p<0.05$), EBOV VP40 ($p<0.05$), SUDV NP ($p<0.05$), TAFV VP40 ($p<0.05$), RESTV GPΔTM (insect, $p<0.05$), and RESTV NP ($p<0.05$). Among the three antigens, the NP showed the highest levels of antibody cross-reactivity, followed by VP40, and GP proteins.

TABLE 3

Summary of recombinant proteins used in the microarray

| Species | Proteins |
|---|---|
| MARV | GP-mucin, GPΔTM (insect), GPΔTM (mammalian), NP, VP40 |
| EBOV | GP-mucin, GPΔTM (insect), GPΔTM (mammalian), NP, VP40 |
| BDBV | GP-mucin, GPΔTM (insect), GPΔTM (mammalian), NP, VP40 |
| SUDV | GP-mucin, GPΔTM (insect), GPΔTM (mammalian), NP, VP40 |
| TAFV | GP-mucin, GPΔTM (mammalian), NP, VP40 |
| RESTV | GP-mucin, GPΔTM (insect), GPΔTM (mammalian), NP, VP40 |

Discussion

The data demonstrates that the compositions and methods provided herein can identify antibody responses by human survivors of Ebola and Marburg infection. Previous studies have reported that most antibody production in hosts was directed mainly towards GP, NP and VP40 proteins (Johnson, Wambui et al. 1986, Leroy, Baize et al. 2000, Lee, Fusco et al. 2008). Hence, for this example, these three proteins were used in a microarray application. The VP40 and NP were expressed as full length recombinant proteins. The GP proteins were produced in three different formats, namely GP-mucin, insect cell expressed GPΔTM, and mammalian cell expressed GPΔTM. The GP protein is extensively glycosylated (Lee, Fusco et al. 2008). We included both multi-domain GPΔTM, expressed as glycosylated proteins in insect or mammalian cell cultures, and single domain GP-mucins that were produced as non-glycosylated proteins in E. coli. The results presented here show that the mucin-like domain contributes substantially to human antibody, as polyclonal antibody recognition of the isolated GP mucin-like domain was comparable to the GPΔTM recombinant protein (see also, Kamata, Natesan et al. 2014).

Antibody responses to Ebola infections have been studied using ELISA (Nakayama, Yokoyama et al. 2010) (Prehaud, Hellebrand et al. 1998) (Saijo, Niikura et al. 2001) and Western blots (Leroy, Baize et al. 2000). Nakayama et aL has used recombinant GP from Ebola in ELISA to detect IgG and IgM from infected individuals. Neutralizing humoral responses to Ebola proteins by human survivors of SUDV (Gulu) infection by ELISA were also reported (Sobarzo, Perelman et al. 2012) (Sobarzo, Groseth et al. 2013), and viral cell cultures were used as antigens in an ELISA to study IgM and IgG responses (Macneil, Reed et al. 2011). Antibody cross-reactivity among Ebola and Marburg viruses is not well-characterized at the protein level. The sera samples were obtained from survivors of three different outbreaks that occurred in Uganda (Gulu-2000, Bundibugyo-2007 and Kabale-2012). The time of sera collection varied from one year (MARV), seven years (BDBV), and fourteen years (SUDV) after the outbreak of the disease. Two types of controls were used in this study. One group comprised of sera from healthy controls collected from the same area (Uganda) and the second group of sera collected from a completely different geographical region (USA). The background antibody levels in endemic areas were slightly elevated compared to sera obtained from non-endemic areas, emphasizing the need to include appropriate controls for correct interpretation of data.

Figure 13:
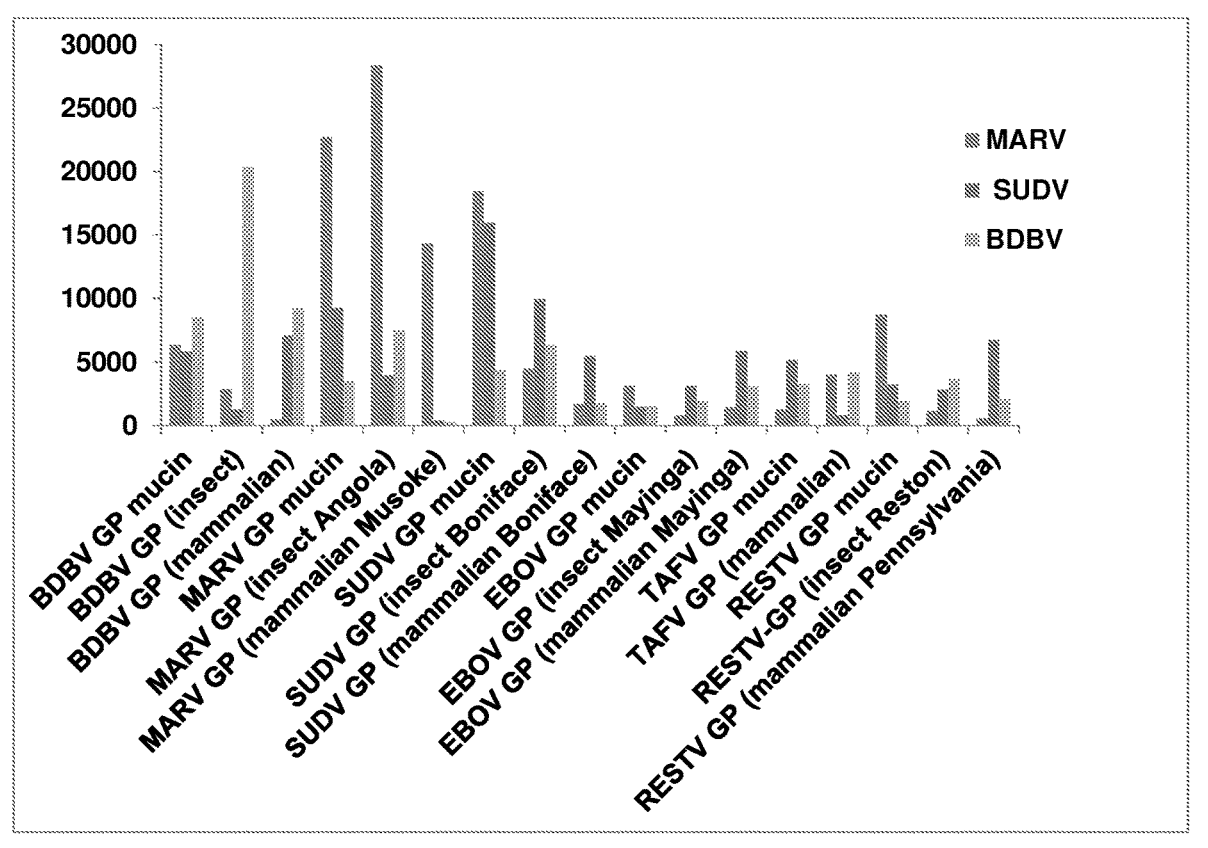

The convalescent sera exhibited high levels of antibody binding for all antigens from the same species of filovirus that caused the infection (FIG. 9). Among the three antigens we tested, antibody levels were highest for NP, followed by GP and VP40. The NP protein is essential for replication of viral genome and formation of the nucleocapsid. Each virion contains about 3200 NP molecules (Bharat, Noda et al. 2012). The C-terminus region of the NP protein is highly antigenic and many epitopes have been identified in this region (Saijo, Niikura et al. 2001) (Changula, Yoshida et al. 2013). Hence, it is not surprising that NP elicits strong antibody responses in infected subjects, and our results confirm this observation and corroborate other reports (Sobarzo, Perelman et al. 2012). GP is the primary surface protein of the virion and several experimental vaccines and antibody-based therapeutics target GP. For the three different forms of recombinant GP (GP-mucin, GPΔTM-insect, GPΔTM-mammalian) used in our microarray, the level of antibody binding was similar (FIG. 13 or data not shown) for all six species except for insect cell produced BDBV GPΔTM, which showed higher binding than GP-mucin and GPΔTM-mammalian. Although the VP40 protein is the most abundant protein within the mature virus, our results show that the antibody response to VP40 in humans is lower than that obtained with NP and GP proteins. It is striking that 14 years after infection many individuals within the SUDV survivor group retain antibodies against filoviral proteins. Persistence of antifilovirus antibodies in long-term survivors of infection was previously reported (Wauquier, Becquart et al. 2009, Sobarzo, Ochayon et al. 2013).

Figure 12:
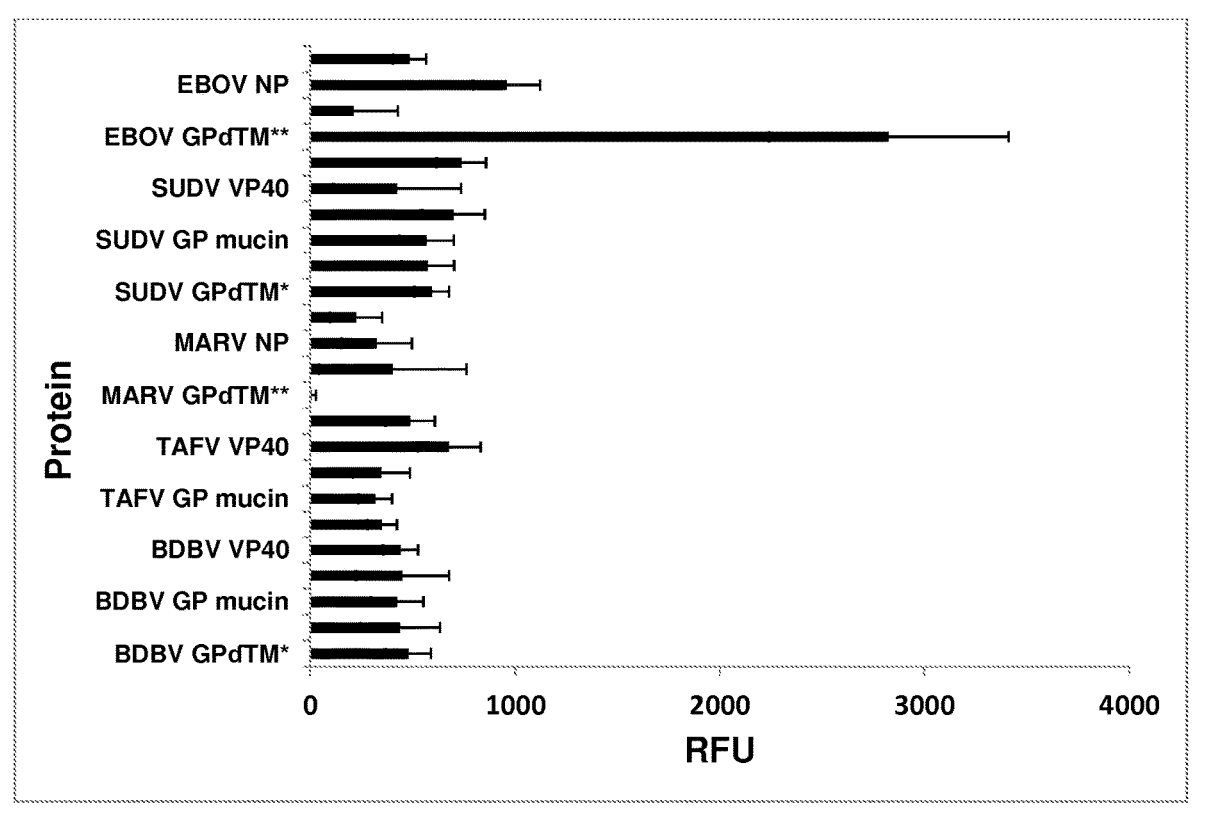

Our study did not include human survivors from EBOV infection from the current West African outbreak due to the unavailability of samples. We did include in our study a serum sample from a human subject vaccinated with chimpanzee rAd5 Ebola vaccine developed by the National Institutes of Health (Ledgerwood, Costner et al. 2010). The vaccine was bivalent, expressing both EBOV and SUDV GP proteins. We found robust antibody response against EBOV GPΔTM (mammalian) but not against SUDV GP protein (FIG. 12). The absence and diminished response against GP proteins may be due to the presence of pre-existing neutralizing antibodies against the Ad5 vector. The capacity of pre-existing vector-specific humoral responses to interfere with efficacy of vaccines is well documented (Pine, Kublin et al. 2011, Ledgerwood, DeZure et al. 2014). In our previous study (Kamata, Natesan et al. 2014) of rhesus macques that were vaccinated with EBOV VLP and challenged with live EBOV, antibodies to GP presented the highest level of specificity in contrast to the human survivor serum antibodies, which showed appreciable amounts of cross-reactivity to heterologous GP proteins. Combined, these results suggest that for the GP antibody response, lower primate and humans may differ depending on how each were exposed to filoviruses. Nakayama et al. reported similar findings by comparing antibody responses to Ebola by mice and humans (Nakayama, Yokoyama et al. 2010).

Cross-reactivity towards heterologous antigens can be observed for all three groups of survivors (BDBV, SUDV and MARV). This is expected since there is considerable amount of protein sequence homology found between the five Ebola species (FIG. 8). The MARV species show the least homology to other members of Ebola. Our phylogenic analysis showed (FIG. 8) that NP is highly conserved among the filoviral species, hence may have common epitopes that are present in all filovirus species. More than 30% of NP residues are conserved among all six species (FIG. 8). The conserved region of NP forms a condensed helix and may contain a structure that plays a role in virus replication (Bharat, Noda et al. 2012). A previous study (Changula, Yoshida et al. 2013) has identified epitopes in this region that cross react to all or several members of Filoviridae. However, the highly variable C terminal region of NP contains the highest number of antigenic regions. This example confirms that among the three antigens tested the NP showed the most cross-reactivity, in agreement with previous reports (Sobarzo, Groseth et al. 2013, Sobarzo, Ochayon et al. 2013, McElroy, Akondy et al. 2015).

This example provides the first report describing a multiplexed assay method and a multiplex protein microarray that was used to identify and analyze antibody specificity and cross-reactivity from human survivors of Ebola and Marburg. While the data suggests a considerable amount of variability in human antibody responses, it identifies GP as desirable targets for neutralizing antibodies (as GP are responsible for virus entry into cells). Nevertheless, the immune responses observed for VP40 and NP can also serve as suitable diagnostic indicators and biomarkers of infection. The disclosure thus provides for detection agents and methods that can effectively identify filoviral-specific antibodies in a sample, and further allows for the application of additional proteins or lysates from filovirus and other new viruses that may present outbreak concerns and issues of public health. Further, the methods and compositions disclosed herein can distinguish Ebola infections from diseases that mimic symptoms similar to that of filoviral infections, and can be used as a tool for seroepidemiological screening as well as for the diagnosis of filoviral infections in mammals.

REFERENCES

1. Feldmann H, Klenk H D. 1996. *Marburg* and *Ebola viruses*. Advances in Virus Research 47:1-52.
2. Leroy E M, Gonzalez J P, Baize S. 2011. *Ebola* and *Marburg* haemorrhagic fever viruses: major scientific advances, but a relatively minor public health threat for Africa. Clinical Microbiology and Infection 17:964-976.
3. Hartman A L, Towner J S, Nichol S T. 2010. *Ebola* and *Marburg* hemorrhagic fever. Clinics in laboratory medicine 30:161-177.
4. Borio L, Inglesby T, Peters C, Schmaljohn A L, Hughes J M, Jahrling P B, Ksiazek T, Johnson K M, Meyerhoff A, O'Toole T. 2002. Hemorrhagic fever viruses as biological weapons. JAMA: the journal of the American Medical Association 287:2391-2405.
5. Feldmann H, Geisbert T W. 2011. *Ebola* haemorrhagic fever. Lancet 377:849-862.
6. Deng I, Duku O, Gillo A. 1978. *Ebola* haemorrhagic fever in *Sudan,* 1976. Report of a WHO/International Study Team. Bulletin of the World Health Organization 56:247-270.
7. Baize S, Leroy E M, Georges-Courbot M-C, Capron M, Lansoud-Soukate J, Debré P, Fisher-Hoch S P, McCormick J B, Georges A J. 1999. Defective humoral responses and extensive intravascular apoptosis are associated with fatal outcome in *Ebola virus*-infected patients. Nature Medicine 5:423-426.
8. Wauquier N, Becquart P, Padilla C, Baize S, Leroy E M. 2010. Human fatal *zaire ebola virus* infection is associated with an aberrant innate immunity and with massive lymphocyte apoptosis. PLoS Negl Trop Dis 4.
9. Villinger F, Rollin P E, Brar S S, Chikkala N F, Winter J, Sundstrom J B, Zaki S R, Swanepoel R, Ansari A A, Peters C J. 1999. Markedly Elevated Levels of Interferon (IFN)-γ, IFN-α, Interleukin (IL)-2, IL-10, and Tumor Necrosis Factor-α Associated with Fatal *Ebola Virus* Infection. Journal of Infectious Diseases 179:S188-5191.

10. Gupta M, Mahanty S, Ahmed R, Rollin P E. 2001. Monocyte-derived human macrophages and peripheral blood mononuclear cells infected with ebola virus secrete MIP-1alpha and TNF-alpha and inhibit poly-IC-induced IFN-alpha in vitro. Virology 284:20-25.

11. MacNeil A, Reed Z, Rollin P E. 2011. Serologic Cross-Reactivity of Human IgM and IgG Antibodies to Five Species of Ebola Virus. PLoS Negl Trop Dis 5:e1175.

12. Ksiazek T G, Rollin P E, Williams A J, Bressler D S, Martin M L, Swanepoel R, Burt F J, Leman P A, Khan A S, Rowe A K, Mukunu R, Sanchez A, Peters C J. 1999. Clinical Virology of Ebola Hemorrhagic Fever (EHF): Virus, Virus Antigen, and IgG and IgM Antibody Findings among EHF Patients in Kikwit, Democratic Republic of the Congo, 1995. Journal of Infectious Diseases 179: S177-S187.

13. Ksiazek T G, West C P, Rollin P E, Jahrling P B, Peters C J. 1999. ELISA for the Detection of Antibodies to Ebola Viruses. Journal of Infectious Diseases 179:S192-S198.

14. Prehaud C, Hellebrand E, Coudrier D, Volchkov V E, Volchkova V A, Feldmann H, Le Guenno B, Bouloy M. 1998. Recombinant Ebola virus nucleoprotein and glycoprotein (Gabon 94 strain) provide new tools for the detection of human infections. Journal of General Virology 79:2565-2572.

15. Nakayama E, Yokoyama A, Miyamoto H, Igarashi M, Kishida N, Matsuno K, Marzi A, Feldmann H, Ito K, Saijo M, Takada A. 2010. Enzyme-linked immunosorbent assay for detection of filovirus species-specific antibodies. Clin Vaccine Immunol 17:1723-1728.

16. Saijo M, Niikura M, Morikawa S, Ksiazek T G, Meyer R F, Peters C J, Kurane I. 2001. Enzyme-linked immunosorbent assays for detection of antibodies to Ebola and Marburg viruses using recombinant nucleoproteins. J Clin Microbiol 39:1-7.

17. Ikegami T, Saijo M, Niikura M, Miranda M E, Calaor A B, Hernandez M, Manalo D L, Kurane I, Yoshikawa Y, Morikawa S. 2003. Immunoglobulin G enzyme-linked immunosorbent assay using truncated nucleoproteins of Reston Ebola virus. Epidemiology and infection 130:533-539.

18. Groen J, van den Hoogen B G, Burghoorn-Maas C P, Fooks A R, Burton J, Clegg C J S C, Zeller H, Osterhaus A D M E. 2003. Serological reactivity of baculovirus-expressed Ebola virus VP35 and nucleoproteins. Microbes and Infection 5:379-385.

19. Sanchez A, Kiley M P, Holloway B P, Auperin D D. 1993. Sequence analysis of the Ebola virus genome: organization, genetic elements, and comparison with the genome of Marburg virus. Virus research 29:215-240.

20. Feldmann H, Mühlberger E, Randolf A, Will C, Kiley M P, Sanchez A, Klenk H-D. 1992. Marburg virus, a filovirus: messenger RNAs, gene order, and regulatory elements of the replication cycle. Virus research 24:1-19.

21. Becker S, Rinne C, Hofsäss U, Klenk H-D, Mühlberger E. 1998. Interactions of Marburg virus nucleocapsid proteins. Virology 249:406-417.

22. Elliott L H, Kiley M P, McCormick J B. 1985. Descriptive analysis of Ebola virus proteins. Virology 147:169-176.

23. Muhlberger E, Lotfering B, Klenk H D, Becker S. 1998. Three of the four nucleocapsid proteins of Marburg virus, NP, VP35, and L, are sufficient to mediate replication and transcription of Marburg virus-specific monocistronic minigenomes. Journal of virology 72:8756.

24. Muhlberger E, Weik M, Volchkov V E, Klenk H D, Becker S. 1999. Comparison of the transcription and replication strategies of Marburg virus and Ebola virus by using artificial replication systems. Journal of virology 73:2333.

25. Weik M, Modrof J, Klenk H D, Becker S, Muhlberger E. 2002. Ebola Virus VP30-Mediated Transcription Is Regulated by RNA Secondary Structure Formation. Journal of virology 76:8532-8539.

26. Harty R N, Brown M E, Wang G, Huibregtse J, Hayes F P. 2000. A PPxY motif within the VP40 protein of Ebola virus interacts physically and functionally with a ubiquitin ligase: implications for filovirus budding. Proceedings of the National Academy of Sciences of the United States of America 97:13871-13876.

27. Jasenosky L D, Neumann G, Lukashevich I, Kawaoka Y. 2001. Ebola virus VP40-induced particle formation and association with the lipid bilayer. J Virol 75:5205-5214.

28. Reid S P, Leung L W, Hartman A L, Martinez O, Shaw M L, Carbonnelle C, Volchkov V E, Nichol S T, Basler C F. 2006. Ebola virus VP24 binds karyopherin alpha1 and blocks STAT1 nuclear accumulation. J Virol 80:5156-5167.

29. Huang Y, Xu L, Sun Y, Nabel G J. 2002. The Assembly of Ebola Virus Nucleocapsid Requires Virion-Associated Proteins 35 and 24 and Posttranslational Modification of Nucleoprotein. Molecular Cell 10:307-316.

30. Hoenen T, Groseth A, Kolesnikova L, Theriault S, Ebihara H, Hartlieb B, Bamberg S, Feldmann H, Ströher U, Becker S. 2006. Infection of Naïve Target Cells with Virus-Like Particles: Implications for the Function of Ebola Virus VP24. Journal of virology 80:7260-7264.

31. Sanchez A, Trappier S G, Mahy B W, Peters C J, Nichol S T. 1996. The virion glycoproteins of Ebola viruses are encoded in two reading frames and are expressed through transcriptional editing. Proceedings of the National Academy of Sciences 93:3602.

32. Volchkov V E, Becker S, Volchkova V A, Ternovoj V A, Kotov A N, Netesov S V, Klenk H D. 1995. GP mRNA of Ebola Virus Is Edited by the Ebola Virus Polymerase and by T7 and Vaccinia Virus Polymerases1. Virology 214:421-430.

33. Sanchez A, Yang Z Y, Xu L, Nabel G J, Crews T, Peters C J. 1998. Biochemical analysis of the secreted and virion glycoproteins of Ebola virus. Journal of virology 72:6442.

34. Feldmann H, Will C, Schikore M, Slenczka W, Klenk H D. 1991. Glycosylation and oligomerization of the spike protein of Marburg virus. Virology 182:353-356.

35. Yonezawa A, Cavrois M, Greene W C. 2005. Studies of ebola virus glycoprotein-mediated entry and fusion by using pseudotyped human immunodeficiency virus type 1 virions: involvement of cytoskeletal proteins and enhancement by tumor necrosis factor alpha. J Virol 79:918-926.

36. Fernandez S, Cisney E D, Tikhonov A P, Schweitzer B, Putnak R J, Simmons M, Ulrich R G. 2011. Antibody recognition of the dengue virus proteome and implications for development of vaccines. Clin Vaccine Immunol 18:523-532.

37. Warfield K L, Swenson D L, Olinger G G, Kalina W V, Aman M J, Bavari S. 2007. Ebola virus-like particle-based vaccine protects nonhuman primates against lethal Ebola virus challenge. Journal of Infectious Diseases 196:S430.

38. Sobarzo A, Perelman E, Groseth A, Dolnik O, Becker S, Lutwama J J, Dye J M, Yavelsky V, Lobel L, Marks R S. 2012. Profiling the native specific human humoral immune response to Sudan Ebola virus strain Gulu by chemiluminescence enzyme-linked immunosorbent assay. Clin Vaccine Immunol 19:1844-1852.
39. Dowling W, Thompson E, Badger C, Mellquist J L, Garrison A R, Smith J M, Paragas J, Hogan R J, Schmaljohn C. 2007. Influences of glycosylation on antigenicity, immunogenicity, and protective efficacy of ebola virus GP DNA vaccines. J Virol 81:1821-1837.
40. Wilson J A, Hevey M, Bakken R, Guest S, Bray M, Schmaljohn A L, Hart M K. 2000. Epitopes involved in antibody-mediated protection from Ebola virus. Science 287:1664.
41. Shahhosseini S, Das D, Qiu X, Feldmann H, Jones S M, Suresh M R. 2007. Production and characterization of monoclonal antibodies against different epitopes of Ebola virus antigens. Journal of virological methods 143:29-37.
42. Martinez O, Tantral L, Mulherkar N, Chandran K, Basler C F. 2011. Impact of Ebola mucin-like domain on anti-glycoprotein antibody responses induced by Ebola virus-like particles. J Infect Dis 204 Suppl 3:S825-832.
43. Changula K, Yoshida R, Noyori O, Marzi A, Miyamoto H, Ishijima M, Yokoyama A, Kajihara M, Feldmann H, Mweene A S, Takada A. 2013. Mapping of conserved and species-specific antibody epitopes on the Ebola virus nucleoprotein. Virus Res 176:83-90.
44. Lucht A, Grunow R, Möller P, Feldmann H, Becker S. 2003. Development, characterization and use of monoclonal VP40-antibodies for the detection of Ebola virus. Journal of virological methods 111:21-28.
45. Niikura M, Ikegami T, Saijo M, Kurata T, Kurane I, Morikawa S. 2003. Analysis of Linear B-Cell Epitopes of the Nucleoprotein of Ebola Virus That Distinguish Ebola Virus Subtypes. Clinical and Vaccine Immunology 10:83-87.
46. Leroy E M, Baize S, Volchkov V E, Fisher-Hoch S P, Georges-Courbot M C, Lansoud-Soukate J, Capron M, Debré P, McCormick J B, Georges A J. 2000. Human asymptomatic Ebola infection and strong inflammatory response. The Lancet 355:2210-2215.
47. Roddy P, Howard N, Van Kerkhove M D, Lutwama J, Wamala J, Yoti Z, Colebunders R, Palma P P, Sterk E, Jeffs B, Van Herp M, Borchert M. 2012. Clinical manifestations and case management of Ebol haemorrhagic fever caused by a newly identified virus strain, Bundibugyo, Uganda, 2007-2008. PloS one 7:e52986.
48. Allaranga Y, Kone M L, Formenty P, Libama F, Boumandouki P, Woodfill C J, Sow I, Duale S, Alemu W, Yada A. 2010. Lessons learned during active epidemiological surveillance of Ebola and Marburg viral hemorrhagic fever epidemics in Africa. East African journal of public health 7:30-36.
49. Bonney J H K, Osei-Kwasi M, Adiku T K, Barnor J S, Amesiya R, Kubio C, Ahadzie L, Ölschläger S, Lelke M, Becker-Ziaja B, Pahlmann M, Günther S. 2013. Hospital-Based Surveillance for Viral Hemorrhagic Fevers and Hepatitides in Ghana. PLoS Negl Trop Dis 7:e2435.
50. Leroy E M, Rouquet P, Formenty P, Souquiere S, Kilbourne A, Froment J M, Bermejo M, Smit S, Karesh W, Swanepoel R, Zaki S R, Rollin P E. 2004. Multiple Ebola virus transmission events and rapid decline of central African wildlife. Science 303:387-390.
51. Bharat T A, et al. 2012. Structural dissection of Ebola virus and its assembly determinants using cryo-electron tomography. Proc Natl Acad Sci USA 109(11): 4275-4280.
52. Castresana J. 2000. Selection of conserved blocks from multiple alignments for their use in phylogenetic analysis. Mol Biol Evol 17(4): 540-552.
53. Di Tommaso P, et al. 2011. T-Coffee: a web server for the multiple sequence alignment of protein and RNA sequences using structural information and homology extension. Nucleic Acids Res 39(Web Server issue): W13-17.
54. Guindon S, et al. 2010. New algorithms and methods to estimate maximum-likelihood phylogenies: assessing the performance of PhyML 3.0. Syst Biol 59(3): 307-321.
55. Hall T A. 1999. A user-friendly biological sequence alignment editor and analysis program for Windows 95/98/NT. Acids Symp Ser 41: 95-98.
56. Johnson B K, et al. 1986. Seasonal variation in antibodies against Ebola virus in Kenyan fever patients. Lancet 1(8490): 1160.
57. Kamata T, et al. 2014. Determination of specific antibody responses to the six species of ebola and marburg viruses by multiplexed protein microarrays. Clin Vaccine Immunol 21(12): 1605-1612.
58. Keasey S L, et al. 2009. Extensive antibody cross-reactivity among infectious gram-negative bacteria revealed by proteome microarray analysis. Mol Cell Proteomics 8(5): 924-935.
59. Larkin M A, et al. 2007. Clustal W and Clustal X version 2.0. Bioinformatics 23(21): 2947-2948.
60. Ledgerwood J E, et al. 2010. A replication defective recombinant Ad5 vaccine expressing Ebola virus GP is safe and immunogenic in healthy adults. Vaccine 29(2): 304-313.
61. Ledgerwood J E, et al. 2014. Chimpanzee Adenovirus Vector Ebola Vaccine -Preliminary Report. N Engl J Med.
62. Lee J E, et al. 2008. Structure of the Ebola virus glycoprotein bound to an antibody from a human survivor. Nature 454(7201): 177-182.
63. Lio P and Goldman N 1998. Models of molecular evolution and phylogeny. Genome Res 8(12): 1233-1244.
64. McElroy A K, et al. 2015. Human Ebola virus infection results in substantial immune activation. Proc Natl Acad Sci USA.
65. Notredame C, et al. (2000). T-Coffee: A novel method for fast and accurate multiple sequence alignment. J Mol Biol 302(1): 205-217.
66. Nye T M, et al. 2006. A novel algorithm and web-based tool for comparing two alternative phylogenetic trees. Bioinformatics 22(1): 117-119.
67. Pine S O, et al. 2011. Pre-existing adenovirus immunity modifies a complex mixed Th1 and Th2 cytokine response to an Ad5/HIV-1 vaccine candidate in humans. PLoS One 6(4): e18526.
68. Sanchez A, et al. 1992. Sequence analysis of the Marburg virus nucleoprotein gene: comparison to Ebola virus and other non-segmented negative-strand RNA viruses. J Gen Virol 73 (Pt 2): 347-357.
69. Sobarzo A, et al. 2013. Profile and persistence of the virus-specific neutralizing humoral immune response in human survivors of Sudan ebolavirus (Gulu). J Infect Dis 208(2): 299-309.
70. Sobarzo A., et al. 2013. Persistent immune responses after Ebola virus infection. N Engl J Med 369(5): 492-493.
71. Talavera G and Castresana J. 2007. Improvement of phylogenies after removing divergent and ambiguously aligned blocks from protein sequence alignments. Syst Biol 56(4): 564-577.
72. Wauquier N., et al. 2009. Immunoglobulin G in Ebola outbreak survivors, Gabon. Emerg Infect Dis 15(7): 1136-1137.

The invention claimed is:

1. A detection agent comprising a substrate, one or more glycoproteins (GPs), one or more nucleoproteins (NP), and one or more virion protein 40 (VP40);
   the one or more GPs, the one or more NPs, and the one or more VP40s being attached to the substrate, immunoreactive as attached to the substrate, and from *Marburg marburgvirus, Sudan ebolavirus, Zaire ebolavirus, Reston ebolavirus, Bundibugyo ebolavirus*, or *Taï Forest ebolavirus*;
   at least one GP, at least one NP, and at least one VP40 being from different filoviruses;
   the one or more NPs comprising SEQ ID NO:4, SEQ ID NO:10, SEQ ID NO:16, SEQ ID NO:22, SEQ ID NO:28, or SEQ ID NO:34;
   the one or more VP40s comprising SEQ ID NO:2, SEQ ID NO:8, SEQ ID NO:14, SEQ ID NO:20, SEQ ID NO:26, or SEQ ID NO:32; and
   the one or more GPs comprising a GP-mucin domain or a GP ectodomain (GPΔTM) and the one or more GPs further comprising SEQ ID NO:6, SEQ ID NO:12, SEQ ID NO:18, SEQ ID NO:24, SEQ ID NO:30, or SEQ ID NO:36.

2. The detection agent of claim 1 being selected from the group consisting of a microarray, microparticles, and nanoparticles.

3. The detection agent of claim 1 being a microarray.

4. A method for detecting the presence of a filovirus-specific antibody in a biological sample obtained from a subject comprising:

(a) incubating the biological sample with the detection agent of claim 1 under conditions that allow binding of the filovirus-specific antibody to the detection agent; and (b) detecting the filovirus-specific antibody bound to detection agent.

5. The method of claim 4, the detection agent comprising the fragment of the GP-mucin.

6. The method of claim 4, the detection agent comprising the GPΔTM or fragment thereof.

7. A method for detecting filovirus antibodies in a subject, comprising:

a) incubating a sample obtained from the subject with the detection agent of claim 1 under conditions that facilitate antigen-antibody binding; and b) detecting the bound antibody in a).

8. The method of claim 7, the detection agent comprising the fragment of the GP-mucin.

9. The method of claim 7, the detection agent comprising the GPΔTM or fragment thereof.

10. A kit comprising:
the detection agent of claim 1;
at least one reagent that can detect a filovirus-specific antibody bound to the detection agent of claim 1; and
instructions for use of the kit.

11. The detection agent of claim 1 comprising the fragment of the GP-mucin.

12. The detection agent of claim 1 comprising the GPΔTM or fragment thereof.

13. The detection agent of claim 1, comprising a non-glycosylated GP-mucin.

14. The method of claim 4, the detection agent comprising a non-glycosylated GP-mucin.

15. The method of claim 7, the detection agent comprising a non-glycosylated GP-mucin.

16. The kit of claim 10, the detection agent comprising a non-glycosylated GP-mucin.

17. A detection agent comprising a substrate, a first nucleoprotein (NP) comprising SEQ ID NO:4, a second NP comprising SEQ ID NO:10, a third NP comprising SEQ ID NO:16, a fourth NP comprising SEQ ID NO:22, a fifth NP comprising SEQ ID NO: 28, a sixth NP comprising SEQ ID NO:34, a first virion protein 40 (VP40) comprising SEQ ID NO:2, a second VP40 comprising SEQ ID NO:8, a third VP40 comprising SEQ ID NO:14, a fourth VP40 comprising SEQ ID NO:20, a fifth VP40 comprising SEQ ID NO:26, a sixth VP40 comprising SEQ ID NO:32, a first glycoprotein (GP) comprising SEQ ID NO:6, a second GP comprising SEQ ID NO:12, a third GP comprising SEQ ID NO:18, a fourth GP comprising SEQ ID NO:24, a fifth GP comprising SEQ ID NO:30, and a sixth GP comprising SEQ ID NO:36; the first through sixth NPs, the first through sixth VP40s, the first through sixth GPs being attached to the substrate and immunoreactive as attached to the substrate; the first through sixth GPs comprising a GP-mucin domain or a GP ectodomain (GPΔTM).

18. A method for detecting the presence of a filovirus-specific antibody in biological sample obtained from a subject comprising:

(a) incubating the biological sample with the detection agent of claim 17 under conditions that allow binding of the filovirus-specific antibody to the detection agent; and (b) detecting the filovirus-specific antibody bound to detection agent.

19. A method for detecting filovirus antibodies in a subject, comprising:

a) incubating a sample obtained from the subject with the detection agent of claim 17 under conditions that facilitate antigen-antibody binding; and c) detecting the bound antibody in b).

* * * * *

SEQUENCE LISTING

<160> NUMBER OF SEQ ID NOS: 36

<210> SEQ ID NO 1
<211> LENGTH: 981
<212> TYPE: DNA
<213> ORGANISM: Ebola virus

<400> SEQUENCE: 1

| | | | | | |
|---|---|---|---|---|---|
| atgaggcggg | ttatattacc | tactgctcct | cctgaatata | tggaggccat | ataccctgtc | 60 |
| aggtcaaatt | caacaattgc | tagaggtggc | aacagcaata | caggcttcct | gacgccggag | 120 |
| tcagtcaatg | gggacactcc | atcgaatcca | ctcaggccaa | ttgccgatga | caccatcgac | 180 |
| catgccagcc | acacaccagg | cagtgtgtca | tcagcattca | tccttgaagc | tatggtgaat | 240 |
| gtcatatcgg | gccccaaagt | gctaatgaag | caaattccaa | tttggcttcc | tctaggtgtc | 300 |
| gctgatcaaa | agacctacag | ctttgactca | actacggccg | ccatcatgct | tgcttcatac | 360 |
| actatcaccc | atttcggcaa | ggcaaccaat | ccacttgtca | gagtcaatcg | gctgggtcct | 420 |
| ggaatcccgg | atcatcccct | caggctcctg | cgaattggaa | accaggcttt | cctccaggag | 480 |
| ttcgttcttc | cgccagtcca | actacccag | tatttcacct | tgatttgac | agcactcaaa | 540 |
| ctgatcaccc | aaccactgcc | tgctgcaaca | tggaccgatg | acactccaac | aggatcaaat | 600 |
| ggagcgttgc | gtccaggaat | tcatttcat | ccaaaacttc | gccccattct | tttacccaac | 660 |
| aaaagtggga | agaaggggaa | cagtgccgat | ctaacatctc | cggagaaaat | ccaagcaata | 720 |
| atgacctcac | tccaggactt | caagatcgtt | ccaattgatc | caaccaaaaa | tatcatggga | 780 |
| atcgaagtgc | cagaaactct | ggtccacaag | ctgaccggta | agaaggtgac | ttctaaaaat | 840 |
| ggacaaccaa | tcatccctgt | tcttttgcca | aagtacattg | gtttggaccc | ggtggctcca | 900 |
| ggagacctca | ccatggtaat | cacacaggat | tgtgacacgt | gtcattctcc | tgcaagtctt | 960 |
| ccagctgtga | ttgagaagta | a | | | | 981 |

<210> SEQ ID NO 2
<211> LENGTH: 326
<212> TYPE: PRT
<213> ORGANISM: Ebola virus

<400> SEQUENCE: 2

Met Arg Arg Val Ile Leu Pro Thr Ala Pro Pro Glu Tyr Met Glu Ala
1               5                   10                  15

Ile Tyr Pro Val Arg Ser Asn Ser Thr Ile Ala Arg Gly Gly Asn Ser
            20                  25                  30

Asn Thr Gly Phe Leu Thr Pro Glu Ser Val Asn Gly Asp Thr Pro Ser
        35                  40                  45

Asn Pro Leu Arg Pro Ile Ala Asp Asp Thr Ile Asp His Ala Ser His
    50                  55                  60

Thr Pro Gly Ser Val Ser Ser Ala Phe Ile Leu Glu Ala Met Val Asn
65                  70                  75                  80

Val Ile Ser Gly Pro Lys Val Leu Met Lys Gln Ile Pro Ile Trp Leu
                85                  90                  95

Pro Leu Gly Val Ala Asp Gln Lys Thr Tyr Ser Phe Asp Ser Thr Thr
            100                 105                 110

Ala Ala Ile Met Leu Ala Ser Tyr Thr Ile Thr His Phe Gly Lys Ala
        115                 120                 125

Thr Asn Pro Leu Val Arg Val Asn Arg Leu Gly Pro Gly Ile Pro Asp
    130                 135                 140

His Pro Leu Arg Leu Leu Arg Ile Gly Asn Gln Ala Phe Leu Gln Glu
145                 150                 155                 160

Phe Val Leu Pro Val Gln Leu Pro Gln Tyr Phe Thr Phe Asp Leu
            165                 170                 175

Thr Ala Leu Lys Leu Ile Thr Gln Pro Leu Pro Ala Ala Thr Trp Thr
                180                 185                 190

Asp Asp Thr Pro Thr Gly Ser Asn Gly Ala Leu Arg Pro Gly Ile Ser
            195                 200                 205

Phe His Pro Lys Leu Arg Pro Ile Leu Leu Pro Asn Lys Ser Gly Lys
    210                 215                 220

Lys Gly Asn Ser Ala Asp Leu Thr Ser Pro Glu Lys Ile Gln Ala Ile
225                 230                 235                 240

Met Thr Ser Leu Gln Asp Phe Lys Ile Val Pro Ile Asp Pro Thr Lys
                245                 250                 255

Asn Ile Met Gly Ile Glu Val Pro Glu Thr Leu Val His Lys Leu Thr
            260                 265                 270

Gly Lys Lys Val Thr Ser Lys Asn Gly Gln Pro Ile Ile Pro Val Leu
    275                 280                 285

Leu Pro Lys Tyr Ile Gly Leu Asp Pro Val Ala Pro Gly Asp Leu Thr
290                 295                 300

Met Val Ile Thr Gln Asp Cys Asp Thr Cys His Ser Pro Ala Ser Leu
305                 310                 315                 320

Pro Ala Val Ile Glu Lys
            325

<210> SEQ ID NO 3
<211> LENGTH: 2220
<212> TYPE: DNA
<213> ORGANISM: Ebola virus

<400> SEQUENCE: 3
atggattctc gtcctcagaa agtctggatg gcgccgagtc tcactgaatc tgacatggat      60
taccacaaga tcttgacagc aggtctgtcc gttcaacagg ggattgttcg gcaaagagtc     120
atcccagtgt atcaagtaaa caatcttgaa gaaatttgcc aacttatcat acaggccttt     180
gaagcaggtg ttgattttca agagagtgcg acagtttcc ttctcatgct tgtcttcat      240 catgcgtacc agggagatta caaactttc ttggaaagtg gcgcagtcaa gtatttggaa      300
gggcacgggt ccgttttga agtcaagaag cgtgatggag tgaagcgcct tgaggaattg      360
ctgccagcag tatctagtgg aaaaacatt aagagaacac ttgctgccat gccggaagag      420
gagacaactg aagctaatgc cggtcagttt ctctcctttg caagtctatt ccttccgaaa      480
ttggtagtag agaaaaaggc ttgccttgag aaggttcaaa ggcaaattca gtacatgca      540 gagcaaggac tgatacaata tccaacagct tggcaatcag taggacacat gatggtgatt      600
ttccgtttga tgcgaacaaa ttttctgatc aaatttctcc taatacacca agggatgcac      660
atggttgccg ggcatgatgc caacgatgct gtgatttcaa attcagtggc tcaagctcgt      720
ttttcaggct tattgattgt caaaacagta cttgatcata tcctacaaaa gacagaacga      780
ggagttcgtc tccatcctct tgcaaggacc gccaaggtaa aaaatgaggt gaactccttt      840
aaggctgcac tcagctccct ggccaagcat ggagagtatg ctcctttcgc ccgactttg       900 aacctttctg gagtaaataa tcttgagcat ggtctttcc ctcaactatc ggcaattgca      960
ctcggagtcg ccacagcaca cgggagtacc ctcgcaggag taaatgttgg agaacagtat    1020
caacaactca gagaggctgc cactgaggct gagaagcaac tccaacaata tgcagagtct    1080

```
cgcgaacttg accatcttgg acttgatgat caggaaaaga aaattcttat gaacttccat    1140
cagaaaaaga acgaaatcag cttccagcaa acaaacgcta tggtaactct aagaaaagag    1200
cgcctggcca agctgacaga agctatcact gctgcgtcac tgcccaaaac aagtggacat    1260
tacgatgatg atgacgacat tccctttcca ggacccatca atgatgacga caatcctggc    1320
catcaagatg atgatccgac tgactcacag gatacgacca ttcccgatgt ggtggttgat    1380
cccgatgatg aagctacggc gaataccag agttactcgg aaaacggcat gaatgcacca    1440
gatgacttgg tcctattcga tctagacgag gacgacgagg acactaagcc agtgcctaat    1500
agatcgacca agggtggaca acagaagaac agtcaaaagg ccagcatat agagggcaga    1560
cagacacaat ccaggccaat tcaaaatgtc ccaggccctc acagaacaat ccaccacgcc    1620
agtgcgccac tcacggacaa tgacagaaga aatgaaccct ccggctcaac agccctcgc    1680
atgctgacac aattaacga gaggcagac ccactggacg atgccgacga cgagacgtct    1740
agccttccgc ccttggagtc agatgatgaa gagcaggaca gggacggaac ttccaaccgc    1800
acacccactg tcgccccacc ggctcccgta tacagagatc actctgaaaa gaagaactc    1860
ccgcaagacg agcaacaaga tcaggaccac actcaagagg ccaggaacca ggacagtgac    1920
aacacccagt cagaacactc ttttgaggag atgtatcgcc acattctaag atcacagggg    1980
ccatttgatg ctgttttgta ttatcatatg atgaaggatg agcctgtagt tttcagtacc    2040
agtgatggca aagagtacac gtatccagac tcccttgaag aggaatatcc accatggctc    2100
actgaaaaag aggctatgaa tgaagagaat agatttgtta cattggatgg tcaacaattt    2160
tattggccgg tgatgaatca caagaataaa ttcatggcaa tcctgcaaca tcatcagtga    2220
```

<210> SEQ ID NO 4
<211> LENGTH: 739
<212> TYPE: PRT
<213> ORGANISM: Ebola virus

<400> SEQUENCE: 4

Met Asp Ser Arg Pro Gln Lys Val Trp Met Ala Pro Ser Leu Thr Glu
1               5                   10                  15

Ser Asp Met Asp Tyr His Lys Ile Leu Thr Ala Gly Leu Ser Val Gln
            20                  25                  30

Gln Gly Ile Val Arg Gln Arg Val Ile Pro Val Tyr Gln Val Asn Asn
        35                  40                  45

Leu Glu Glu Ile Cys Gln Leu Ile Ile Gln Ala Phe Glu Ala Gly Val
    50                  55                  60

Asp Phe Gln Glu Ser Ala Asp Ser Phe Leu Leu Met Leu Cys Leu His
65                  70                  75                  80

His Ala Tyr Gln Gly Asp Tyr Lys Leu Phe Leu Glu Ser Gly Ala Val
                85                  90                  95

Lys Tyr Leu Glu Gly His Gly Phe Arg Phe Glu Val Lys Lys Arg Asp
            100                 105                 110

Gly Val Lys Arg Leu Glu Glu Leu Leu Pro Ala Val Ser Ser Gly Lys
        115                 120                 125

Asn Ile Lys Arg Thr Leu Ala Ala Met Pro Glu Glu Thr Thr Glu
    130                 135                 140

Ala Asn Ala Gly Gln Phe Leu Ser Phe Ala Ser Leu Phe Leu Pro Lys
145                 150                 155                 160

Leu Val Val Gly Glu Lys Ala Cys Leu Glu Lys Val Gln Arg Gln Ile
                165                 170                 175

```
Gln Val His Ala Glu Gln Gly Leu Ile Gln Tyr Pro Thr Ala Trp Gln
            180                 185                 190

Ser Val Gly His Met Met Val Ile Phe Arg Leu Met Arg Thr Asn Phe
        195                 200                 205

Leu Ile Lys Phe Leu Leu Ile His Gln Gly Met His Met Val Ala Gly
    210                 215                 220

His Asp Ala Asn Asp Ala Val Ile Ser Asn Ser Val Ala Gln Ala Arg
225                 230                 235                 240

Phe Ser Gly Leu Leu Ile Val Lys Thr Val Leu Asp His Ile Leu Gln
                245                 250                 255

Lys Thr Glu Arg Gly Val Arg Leu His Pro Leu Ala Arg Thr Ala Lys
                260                 265                 270

Val Lys Asn Glu Val Asn Ser Phe Lys Ala Ala Leu Ser Ser Leu Ala
            275                 280                 285

Lys His Gly Glu Tyr Ala Pro Phe Ala Arg Leu Leu Asn Leu Ser Gly
        290                 295                 300

Val Asn Asn Leu Glu His Gly Leu Phe Pro Gln Leu Ser Ala Ile Ala
305                 310                 315                 320

Leu Gly Val Ala Thr Ala His Gly Ser Thr Leu Ala Gly Val Asn Val
                325                 330                 335

Gly Glu Gln Tyr Gln Gln Leu Arg Glu Ala Ala Thr Glu Ala Glu Lys
                340                 345                 350

Gln Leu Gln Gln Tyr Ala Glu Ser Arg Glu Leu Asp His Leu Gly Leu
            355                 360                 365

Asp Asp Gln Glu Lys Lys Ile Leu Met Asn Phe His Gln Lys Lys Asn
        370                 375                 380

Glu Ile Ser Phe Gln Gln Thr Asn Ala Met Val Thr Leu Arg Lys Glu
385                 390                 395                 400

Arg Leu Ala Lys Leu Thr Glu Ala Ile Thr Ala Ala Ser Leu Pro Lys
                405                 410                 415

Thr Ser Gly His Tyr Asp Asp Asp Asp Ile Pro Phe Pro Gly Pro
                420                 425                 430

Ile Asn Asp Asp Asp Asn Pro Gly His Gln Asp Asp Pro Thr Asp
        435                 440                 445

Ser Gln Asp Thr Thr Ile Pro Asp Val Val Val Asp Pro Asp Asp Gly
450                 455                 460

Ser Tyr Gly Glu Tyr Gln Ser Tyr Ser Glu Asn Gly Met Asn Ala Pro
465                 470                 475                 480

Asp Asp Leu Val Leu Phe Asp Leu Asp Asp Glu Asp Thr Lys
                485                 490                 495

Pro Val Pro Asn Arg Ser Thr Lys Gly Gly Gln Gln Lys Asn Ser Gln
            500                 505                 510

Lys Gly Gln His Ile Glu Gly Arg Gln Thr Gln Ser Arg Pro Ile Gln
            515                 520                 525

Asn Val Pro Gly Pro His Arg Thr Ile His His Ala Ser Ala Pro Leu
            530                 535                 540

Thr Asp Asn Asp Arg Arg Asn Glu Pro Ser Gly Ser Thr Ser Pro Arg
545                 550                 555                 560

Met Leu Thr Pro Ile Asn Glu Glu Ala Asp Pro Leu Asp Asp Ala Asp
                565                 570                 575

Asp Glu Thr Ser Ser Leu Pro Pro Leu Glu Ser Asp Asp Glu Glu Gln
                580                 585                 590
```

```
Asp Arg Asp Gly Thr Ser Asn Arg Thr Pro Thr Val Ala Pro Pro Ala
            595                 600                 605

Pro Val Tyr Arg Asp His Ser Glu Lys Lys Glu Leu Pro Gln Asp Glu
    610                 615                 620

Gln Gln Asp Gln Asp His Thr Gln Glu Ala Arg Asn Gln Asp Ser Asp
625                 630                 635                 640

Asn Thr Gln Ser Glu His Ser Phe Glu Glu Met Tyr Arg His Ile Leu
            645                 650                 655

Arg Ser Gln Gly Pro Phe Asp Ala Val Leu Tyr Tyr His Met Met Lys
                660                 665                 670

Asp Glu Pro Val Val Phe Ser Thr Ser Asp Gly Lys Glu Tyr Thr Tyr
            675                 680                 685

Pro Asp Ser Leu Glu Glu Glu Tyr Pro Pro Trp Leu Thr Glu Lys Glu
            690                 695                 700

Ala Met Asn Glu Glu Asn Arg Phe Val Thr Leu Asp Gly Gln Gln Phe
705                 710                 715                 720

Tyr Trp Pro Val Met Asn His Lys Asn Lys Phe Met Ala Ile Leu Gln
                725                 730                 735

His His Gln

<210> SEQ ID NO 5
<211> LENGTH: 465
<212> TYPE: DNA
<213> ORGANISM: Ebola virus

<400> SEQUENCE: 5
aacagagcca aaaacatcag tggtcagagt ccggcgcgaa cttcttccga cccagggacc      60
aacacaacaa ctgaagacca caaaatcatg gcttcagaaa attcctctgc aatggttcaa     120
gtgcacagtc aaggaaggga agctgcagtg tcgcatctga acccttgc acaatctcc        180 acgagtcctc aacccccac aaccaaacca ggtccggaca cagcaccca aatacaccc        240 gtgtataaac ttgacatctc tgaggcaact caagttgaac aacatcaccg agaacagac      300 aacgacagca cagcctccga cactcccccc gccacgaccg cagccggacc cctaaaagca     360
gagaacacca acacgagcaa gggtaccgac ctcctggacc ccgccaccac aacaagtccc     420
caaaaccaca gcgagaccgc tggcaacaac aacactcatt agtag                     465

<210> SEQ ID NO 6
<211> LENGTH: 153
<212> TYPE: PRT
<213> ORGANISM: Ebola virus

<400> SEQUENCE: 6

Asn Arg Ala Lys Asn Ile Ser Gly Gln Ser Pro Ala Arg Thr Ser Ser
1               5                  10                  15

Asp Pro Gly Thr Asn Thr Thr Thr Glu Asp His Lys Ile Met Ala Ser
            20                  25                  30

Glu Asn Ser Ser Ala Met Val Gln Val His Ser Gln Gly Arg Glu Ala
        35                  40                  45

Ala Val Ser His Leu Thr Thr Leu Ala Thr Ile Ser Thr Ser Pro Gln
    50                  55                  60

Pro Pro Thr Thr Lys Pro Gly Pro Asp Asn Ser Thr His Asn Thr Pro
65                  70                  75                  80

Val Tyr Lys Leu Asp Ile Ser Glu Ala Thr Gln Val Glu Gln His His
                85                  90                  95
```

Arg Arg Thr Asp Asn Asp Ser Thr Ala Ser Asp Thr Pro Pro Ala Thr
            100                 105                 110

Thr Ala Ala Gly Pro Leu Lys Ala Glu Asn Thr Asn Thr Ser Lys Gly
        115                 120                 125

Thr Asp Leu Leu Asp Pro Ala Thr Thr Thr Ser Pro Gln Asn His Ser
    130                 135                 140

Glu Thr Ala Gly Asn Asn Asn Thr His
145                 150

<210> SEQ ID NO 7
<211> LENGTH: 981
<212> TYPE: DNA
<213> ORGANISM: Ebola virus

<400> SEQUENCE: 7

```
atgagaaggg tcactgtgcc gactgcacca cctgcatatg ctgacattgg ctatcctatg    60
agcatgcttc caatcaagtc aagcagggct gtaagtggaa ttcaacagaa acaagaggtc   120
cttcctggaa tggatacacc atcgaactct atgagacctg ttgctgatga taacattgat   180
cacacaagtc ataccccaaa cggagtggcc tcagcattca tcttggaggc aactgtcaat   240
gtgatctcgg ggcccaaagt cctcatgaaa caaatcccta tttggttgcc actcggaatt   300
gctgaccaaa aaacatacag ctttgactca acaacagcag caattatgct cgcatcctac   360
acgatcactc attttggaaa ggccaacaac cccctcgtca gagtgaatcg acttggtcaa   420
ggaataccgg atcaccccact cagattgctc aggatgggga accaggcttt ccttcaagag   480
tttgtgctac caccagttca actgccgcaa tatttcactt ttgatctgac tgcactcaaa   540
ttagtgacac agcctctccc tgctgcaaca tggacagatg agactccgag caacctttca   600
ggagcactcc gtccagggct ctcatttcac ccgaaactga cccgttct acttccaggc   660
aagacgggaa agaaagggca tgtttctgat ctgaccgccc agacaaaat ccagacaatt   720
gtgaacctga tgcaagattt caagattgtg ccaatcgacc cagccaagag catcattggg   780
atcgaggttc cagaattgct ggtccacaag ctcaccggga agaaaatgag tcagaagaac   840
ggacagccta taattcctgt cttactccca aaatacattg gctagatcc aatctcgccc   900
ggagacctaa ctatggtcat aacaccagat tatgatgatt gtcattcacc cgccagttgc   960
tcttatctca gtgaaaagtg a                                             981
```

<210> SEQ ID NO 8
<211> LENGTH: 326
<212> TYPE: PRT
<213> ORGANISM: Ebola virus

<400> SEQUENCE: 8

Met Arg Arg Val Thr Val Pro Thr Ala Pro Pro Ala Tyr Ala Asp Ile
1               5                  10                  15

Gly Tyr Pro Met Ser Met Leu Pro Ile Lys Ser Ser Arg Ala Val Ser
            20                  25                  30

Gly Ile Gln Gln Lys Gln Glu Val Leu Pro Gly Met Asp Thr Pro Ser
        35                  40                  45

Asn Ser Met Arg Pro Val Ala Asp Asp Asn Ile Asp His Thr Ser His
    50                  55                  60

Thr Pro Asn Gly Val Ala Ser Ala Phe Ile Leu Glu Ala Thr Val Asn
65                  70                  75                  80

Val Ile Ser Gly Pro Lys Val Leu Met Lys Gln Ile Pro Ile Trp Leu
            85                  90                  95

```
Pro Leu Gly Ile Ala Asp Gln Lys Thr Tyr Ser Phe Asp Ser Thr Thr
            100                 105                 110

Ala Ala Ile Met Leu Ala Ser Tyr Thr Ile Thr His Phe Gly Lys Ala
        115                 120                 125

Asn Asn Pro Leu Val Arg Val Asn Arg Leu Gly Gln Gly Ile Pro Asp
    130                 135                 140

His Pro Leu Arg Leu Leu Arg Met Gly Asn Gln Ala Phe Leu Gln Glu
145                 150                 155                 160

Phe Val Leu Pro Pro Val Gln Leu Pro Gln Tyr Phe Thr Phe Asp Leu
                165                 170                 175

Thr Ala Leu Lys Leu Val Thr Gln Pro Leu Pro Ala Ala Thr Trp Thr
            180                 185                 190

Asp Glu Thr Pro Ser Asn Leu Ser Gly Ala Leu Arg Pro Gly Leu Ser
        195                 200                 205

Phe His Pro Lys Leu Arg Pro Val Leu Leu Pro Gly Lys Thr Gly Lys
    210                 215                 220

Lys Gly His Val Ser Asp Leu Thr Ala Pro Asp Lys Ile Gln Thr Ile
225                 230                 235                 240

Val Asn Leu Met Gln Asp Phe Lys Ile Val Pro Ile Asp Pro Ala Lys
                245                 250                 255

Ser Ile Ile Gly Ile Glu Val Pro Glu Leu Leu Val His Lys Leu Thr
            260                 265                 270

Gly Lys Lys Met Ser Gln Lys Asn Gly Gln Pro Ile Ile Pro Val Leu
        275                 280                 285

Leu Pro Lys Tyr Ile Gly Leu Asp Pro Ile Ser Pro Gly Asp Leu Thr
    290                 295                 300

Met Val Ile Thr Pro Asp Tyr Asp Asp Cys His Ser Pro Ala Ser Cys
305                 310                 315                 320

Ser Tyr Leu Ser Glu Lys
                325

<210> SEQ ID NO 9
<211> LENGTH: 2217
<212> TYPE: DNA
<213> ORGANISM: Ebola virus

<400> SEQUENCE: 9
atggataaac gggtgagagg ttcatgggcc ctgggaggac aatctgaggt tgatcttgac    60
taccacaaga tattaacagc cgggctttca gtccaacagg ggattgtgcg acagagagtc   120
atcccggtat atgtcgtgaa tgatcttgag ggtatttgtc aacatatcat tcaggctttt   180
gaagcaggtg tagatttcca ggataatgct gatagcttcc ttttactttt atgtttacat   240
catgcctacc aaggagatca taggctcttc ctcaaaagtg atgcagttca atatttagag   300
ggccatggct tcaggtttga ggtccgagaa aaggagaatg tgcaccgtct ggatgaattg   360
ttgcccaatg ttaccggtgg aaaaaatctc aggagaacat ggctgctat gcccgaagag   420 gagacaacgg aagctaatgc tggtcagttt ctatcctttg ccagtttgtt tctacccaaa   480
cttgtcgttg gggagaaagc gtgcctggaa aagtacaaa gcaaattca ggtccatgca   540 gaacaagggc tcattcaata tccaacttcc tggcaatcag ttggacacat gatggtgatc   600
ttccgtttga tgaggacaaa cttttaatc aagtttctac taatacatca agggatgcac   660
atggttgcag gtcatgatgc gaatgacaca gtaatatcta attctgttgc ccaggcaagg   720
ttctctggtc ttctgattgt aaagactgtt ctggatcaca tcctacaaaa aacagatctc   780
```

```
ggagtacgac ttcatccact ggccaggaca gcaaaagtga agaatgaggt cagttcattc    840
aaggcggctc ttggttcact tgccaagcat ggagaatatg ctccgtttgc acgtctcctt    900
aatctttctg gagtcaacaa cttggaacat gggctttatc cacaactttc agccatcgct    960
ttgggtgttg caactgccca cgggagtacg cttgctggtg tgaatgtagg ggagcaatat   1020
cagcaactgc gtgaggctgc tactgaggct gaaaagcaac tccaacaata tgctgaaaca   1080
cgtgagttgg ataaccttgg gcttgatgaa caggagaaga gattctcat  gagcttccac   1140
cagaagaaga atgagatcag cttccagcag actaatgcaa tggtaacctt aaggaaagaa   1200
cggctggcta aattgaccga agccatcacg actgcatcga agatcaaggt tggagaccgt   1260
tatcctgatg acaatgatat tccatttccc gggccgatct atgatgacac tcaccccaat   1320
ccctctgatg acaatcctga tgattcacgt gatacaacta ttccaggtgg tgttgttgac   1380
ccgtatgatg atgagagtaa taattatcct gactacgagg attcggctga aggcaccaca   1440
ggagatcttg atctcttcaa tttggacgac gacgatgatg acagccgacc aggaccacca   1500
gacagggggc agaacaagga gagggcggcc cggacatatg cctccaaga  tccgaccttg   1560
gacggagcga aaaggtgcc  ggagttgacc ccaggttccc atcaaccagg caacctccac   1620
atcaccaagt cgggttcaaa caccaaccaa ccacaaggca atatgtcatc tactctccat   1680
agtatgaccc ctatacagga gaatcgag   cccgatgatc aaaaagataa tgatgacgag   1740
agtctcacat cccttgactc tgaaggtgac gaagatggtg agagcatctc tgaggagaac   1800
accccaactg tagctccacc agcaccagtc tacaaagaca ctggagtaga cactaatcag   1860
cagaatggac caagcagtac tgtagatagt caaggttctg aaagtgaagc tctcccaatc   1920
aactctaaaa agagttccgc actagaagaa acatattatc atctcctaaa aacacagggt   1980
ccatttgagg caatcaatta ttatcaccta atgagtgatg aacccattgc ttttagcact   2040
gaaagtggca aggaatatat cttcccagac tcccttgaag aagcctaccc gccgtggttg   2100
agtgagaagg aggccttaga gaaggaaaat cgttatctgg tcattgatgg ccagcaattc   2160
ctctggccgg taatgagcct acgggacaag ttccttgctg ttcttcaaca tgactga      2217
```

<210> SEQ ID NO 10
<211> LENGTH: 738
<212> TYPE: PRT
<213> ORGANISM: Ebola virus

<400> SEQUENCE: 10

```
Met Asp Lys Arg Val Arg Gly Ser Trp Ala Leu Gly Gly Gln Ser Glu
1               5                   10                  15

Val Asp Leu Asp Tyr His Lys Ile Leu Thr Ala Gly Leu Ser Val Gln
            20                  25                  30

Gln Gly Ile Val Arg Gln Arg Val Ile Pro Val Tyr Val Val Asn Asp
        35                  40                  45

Leu Glu Gly Ile Cys Gln His Ile Ile Gln Ala Phe Glu Ala Gly Val
    50                  55                  60

Asp Phe Gln Asp Asn Ala Asp Ser Phe Leu Leu Leu Cys Leu His
65                  70                  75                  80

His Ala Tyr Gln Gly Asp His Arg Leu Phe Leu Lys Ser Asp Ala Val
                85                  90                  95

Gln Tyr Leu Glu Gly His Gly Phe Arg Phe Glu Val Arg Glu Lys Glu
            100                 105                 110

Asn Val His Arg Leu Asp Glu Leu Leu Pro Asn Val Thr Gly Gly Lys
```

-continued

```
                115                 120                 125
Asn Leu Arg Arg Thr Leu Ala Ala Met Pro Glu Glu Thr Thr Glu
130                 135                 140
Ala Asn Ala Gly Gln Phe Leu Ser Phe Ala Ser Leu Phe Leu Pro Lys
145                 150                 155                 160
Leu Val Val Gly Glu Lys Ala Cys Leu Glu Lys Val Gln Arg Gln Ile
                165                 170                 175
Gln Val His Ala Glu Gln Gly Leu Ile Gln Tyr Pro Thr Ser Trp Gln
                180                 185                 190
Ser Val Gly His Met Met Val Ile Phe Arg Leu Met Arg Thr Asn Phe
                195                 200                 205
Leu Ile Lys Phe Leu Leu Ile His Gln Gly Met His Met Val Ala Gly
210                 215                 220
His Asp Ala Asn Asp Thr Val Ile Ser Asn Ser Val Ala Gln Ala Arg
225                 230                 235                 240
Phe Ser Gly Leu Leu Ile Val Lys Thr Val Leu Asp His Ile Leu Gln
                245                 250                 255
Lys Thr Asp Leu Gly Val Arg Leu His Pro Leu Ala Arg Thr Ala Lys
                260                 265                 270
Val Lys Asn Glu Val Ser Ser Phe Lys Ala Ala Leu Gly Ser Leu Ala
275                 280                 285
Lys His Gly Glu Tyr Ala Pro Phe Ala Arg Leu Leu Asn Leu Ser Gly
                290                 295                 300
Val Asn Asn Leu Glu His Gly Leu Tyr Pro Gln Leu Ser Ala Ile Ala
305                 310                 315                 320
Leu Gly Val Ala Thr Ala His Gly Ser Thr Leu Ala Gly Val Asn Val
                325                 330                 335
Gly Glu Gln Tyr Gln Gln Leu Arg Glu Ala Ala Thr Glu Ala Glu Lys
                340                 345                 350
Gln Leu Gln Gln Tyr Ala Glu Thr Arg Glu Leu Asp Asn Leu Gly Leu
                355                 360                 365
Asp Glu Gln Glu Lys Lys Ile Leu Met Ser Phe His Gln Lys Lys Asn
370                 375                 380
Glu Ile Ser Phe Gln Gln Thr Asn Ala Met Val Thr Leu Arg Lys Glu
385                 390                 395                 400
Arg Leu Ala Lys Leu Thr Glu Ala Ile Thr Thr Ala Ser Lys Ile Lys
                405                 410                 415
Val Gly Asp Arg Tyr Pro Asp Asp Asn Asp Ile Pro Phe Pro Gly Pro
                420                 425                 430
Ile Tyr Asp Asp Thr His Pro Asn Pro Ser Asp Asp Asn Pro Asp Asp
                435                 440                 445
Ser Arg Asp Thr Thr Ile Pro Gly Gly Val Val Asp Pro Tyr Asp Asp
450                 455                 460
Glu Ser Asn Asn Tyr Pro Asp Tyr Glu Asp Ser Ala Glu Gly Thr Thr
465                 470                 475                 480
Gly Asp Leu Asp Leu Phe Asn Leu Asp Asp Asp Asp Asp Ser Arg
                485                 490                 495
Pro Gly Pro Pro Asp Arg Gly Gln Asn Lys Glu Arg Ala Ala Arg Thr
                500                 505                 510
Tyr Gly Leu Gln Asp Pro Thr Leu Asp Gly Ala Lys Lys Val Pro Glu
                515                 520                 525
Leu Thr Pro Gly Ser His Gln Pro Gly Asn Leu His Ile Thr Lys Ser
530                 535                 540
```

-continued

Gly Ser Asn Thr Asn Gln Pro Gln Gly Asn Met Ser Ser Thr Leu His
545                 550                 555                 560

Ser Met Thr Pro Ile Gln Glu Glu Ser Glu Pro Asp Asp Gln Lys Asp
            565                 570                 575

Asn Asp Asp Glu Ser Leu Thr Ser Leu Asp Ser Glu Gly Asp Glu Asp
        580                 585                 590

Gly Glu Ser Ile Ser Glu Glu Asn Thr Pro Thr Val Ala Pro Pro Ala
    595                 600                 605

Pro Val Tyr Lys Asp Thr Gly Val Asp Thr Asn Gln Gln Asn Gly Pro
610                 615                 620

Ser Ser Thr Val Asp Ser Gln Gly Ser Glu Ser Glu Ala Leu Pro Ile
625                 630                 635                 640

Asn Ser Lys Lys Ser Ser Ala Leu Glu Glu Thr Tyr Tyr His Leu Leu
            645                 650                 655

Lys Thr Gln Gly Pro Phe Glu Ala Ile Asn Tyr Tyr His Leu Met Ser
        660                 665                 670

Asp Glu Pro Ile Ala Phe Ser Thr Glu Ser Gly Lys Glu Tyr Ile Phe
    675                 680                 685

Pro Asp Ser Leu Glu Glu Ala Tyr Pro Pro Trp Leu Ser Glu Lys Glu
690                 695                 700

Ala Leu Glu Lys Glu Asn Arg Tyr Leu Val Ile Asp Gly Gln Gln Phe
705                 710                 715                 720

Leu Trp Pro Val Met Ser Leu Arg Asp Lys Phe Leu Ala Val Leu Gln
            725                 730                 735

His Asp

<210> SEQ ID NO 11
<211> LENGTH: 465
<212> TYPE: DNA
<213> ORGANISM: Ebola virus

<400> SEQUENCE: 11
ctcaacgaga cagaagacga tgatgcgaca tcgtcgagaa ctacaaaggg aagaatctcc      60
gaccgggcca ccaggaagta ttcggacctg gttccaaagg attcccctgg gatggtttca     120
ttgcacgtac cagaagggga aacaacattg ccgtctcaga attcgacaga aggtcgaaga     180
gtagatgtga atactcagga actatcacag agacaactgc aacaatcat aggcactaac      240 ggtaacaaca tgcagatctc caccatcggg acaggactga gctccagcca atcctgagt      300 tcctcaccga ccatggcacc aagccctgag actcagacct ccacaaccta cacaccaaaa     360
ctaccagtga tgaccaccga ggaatcaaca acaccaccga gaaactctcc tggctcaaca     420
acagaagcac ccactctcac cacccagag aatataacat agtag                      465

<210> SEQ ID NO 12
<211> LENGTH: 153
<212> TYPE: PRT
<213> ORGANISM: Ebola virus

<400> SEQUENCE: 12

Leu Asn Glu Thr Glu Asp Asp Asp Ala Thr Ser Ser Arg Thr Thr Lys
1               5                   10                  15

Gly Arg Ile Ser Asp Arg Ala Thr Arg Lys Tyr Ser Asp Leu Val Pro
            20                  25                  30

Lys Asp Ser Pro Gly Met Val Ser Leu His Val Pro Glu Gly Glu Thr
        35                  40                  45

```
Thr Leu Pro Ser Gln Asn Ser Thr Glu Gly Arg Arg Val Asp Val Asn
         50                  55                  60
Thr Gln Glu Thr Ile Thr Glu Thr Thr Ala Thr Ile Ile Gly Thr Asn
 65                  70                  75                  80
Gly Asn Asn Met Gln Ile Ser Thr Ile Gly Thr Gly Leu Ser Ser Ser
                 85                  90                  95
Gln Ile Leu Ser Ser Ser Pro Thr Met Ala Pro Ser Pro Glu Thr Gln
             100                 105                 110
Thr Ser Thr Thr Tyr Thr Pro Lys Leu Pro Val Met Thr Thr Glu Glu
         115                 120                 125
Ser Thr Thr Pro Pro Arg Asn Ser Pro Gly Ser Thr Thr Glu Ala Pro
     130                 135                 140
Thr Leu Thr Thr Pro Glu Asn Ile Thr
145                 150
```

```
<210> SEQ ID NO 13
<211> LENGTH: 981
<212> TYPE: DNA
<213> ORGANISM: Ebola virus

<400> SEQUENCE: 13
```

| | | |
|---|---|---:|
| atgaggaggg caattctacc tactgcaccg ccagaataca tagaggctgt ctacccaatg | | 60 |
| agaacggtta gtactagtat caacagtact gccagtggtc cgaactttcc agcaccggat | | 120 |
| gtaatgatga gtgatacacc ctccaactca ctccgaccaa ttgctgatga taacatcgat | | 180 |
| catccaagtc ataccaac cagtgtttca tcagcctta tactcgaggc aatggtgaat | | 240 |
| gtgatatcgg ggccgaaggt actaatgaag caaattccta tatggctccc cttgggtgtt | | 300 |
| gctgatcaaa aacatatag ttttgactca actacagctg caattatgct cgcatcgtac | | 360 |
| accatcactc actttggcaa aacctccaat ccgcttgtga gaatcaatcg acttggtcct | | 420 |
| gggatccccg atcacccgtt gcggcttcta agaataggaa atcaagcctt cttgcaagag | | 480 |
| tttgtgctgc ctccagttca attgccgcag tatttcactt ttgacctgac ggctctaaag | | 540 |
| ctgatcactc aacctctccc ggcagcaacc tggacggatg atactccgac cggtcctaca | | 600 |
| ggaatacttc gtcctggaat tccttttcat cccaaactga gacctatcct attgccaggg | | 660 |
| aagaccggga aaagaggatc cagctccgat cttacttctc ctgataaaat acaagcaata | | 720 |
| atgaactttc tccaagacct caaactcgtg ccgattgatc cagccaagaa cattatgggt | | 780 |
| attgaagtgc cggaactctt ggtccacaga ctaactggaa agaaaatcac aacaaaaaat | | 840 |
| ggtcaaccaa taattcctat tcttctacca agtatattg gcatggatcc catttctcag | | 900 |
| ggagacctca aatggtcat cactcaagac tgtgacactt gccattctcc tgctagtctt | | 960 |
| cctccagtca gcgagaaatg a | | 981 |

```
<210> SEQ ID NO 14
<211> LENGTH: 326
<212> TYPE: PRT
<213> ORGANISM: Ebola virus

<400> SEQUENCE: 14
```

```
Met Arg Arg Ala Ile Leu Pro Thr Ala Pro Pro Glu Tyr Ile Glu Ala
 1               5                  10                  15
Val Tyr Pro Met Arg Thr Val Ser Thr Ser Ile Asn Ser Thr Ala Ser
                 20                  25                  30
Gly Pro Asn Phe Pro Ala Pro Asp Val Met Met Ser Asp Thr Pro Ser
```

```
                35                  40                  45
Asn Ser Leu Arg Pro Ile Ala Asp Asp Asn Ile Asp His Pro Ser His
         50                  55                  60

Thr Pro Thr Ser Val Ser Ser Ala Phe Ile Leu Glu Ala Met Val Asn
 65                  70                  75                  80

Val Ile Ser Gly Pro Lys Val Leu Met Lys Gln Ile Pro Ile Trp Leu
                 85                  90                  95

Pro Leu Gly Val Ala Asp Gln Lys Thr Tyr Ser Phe Asp Ser Thr Thr
            100                 105                 110

Ala Ala Ile Met Leu Ala Ser Tyr Thr Ile Thr His Phe Gly Lys Thr
        115                 120                 125

Ser Asn Pro Leu Val Arg Ile Asn Arg Leu Gly Pro Gly Ile Pro Asp
    130                 135                 140

His Pro Leu Arg Leu Leu Arg Ile Gly Asn Gln Ala Phe Leu Gln Glu
145                 150                 155                 160

Phe Val Leu Pro Pro Val Gln Leu Pro Gln Tyr Phe Thr Phe Asp Leu
                165                 170                 175

Thr Ala Leu Lys Leu Ile Thr Gln Pro Leu Pro Ala Ala Thr Trp Thr
            180                 185                 190

Asp Asp Thr Pro Thr Gly Pro Thr Gly Ile Leu Arg Pro Gly Ile Ser
        195                 200                 205

Phe His Pro Lys Leu Arg Pro Ile Leu Leu Pro Gly Lys Thr Gly Lys
    210                 215                 220

Arg Gly Ser Ser Ser Asp Leu Thr Ser Pro Asp Lys Ile Gln Ala Ile
225                 230                 235                 240

Met Asn Phe Leu Gln Asp Leu Lys Leu Val Pro Ile Asp Pro Ala Lys
                245                 250                 255

Asn Ile Met Gly Ile Glu Val Pro Glu Leu Leu Val His Arg Leu Thr
            260                 265                 270

Gly Lys Lys Ile Thr Thr Lys Asn Gly Gln Pro Ile Ile Pro Ile Leu
        275                 280                 285

Leu Pro Lys Tyr Ile Gly Met Asp Pro Ile Ser Gln Gly Asp Leu Thr
    290                 295                 300

Met Val Ile Thr Gln Asp Cys Asp Thr Cys His Ser Pro Ala Ser Leu
305                 310                 315                 320

Pro Pro Val Ser Glu Lys
                325

<210> SEQ ID NO 15
<211> LENGTH: 2220
<212> TYPE: DNA
<213> ORGANISM: Ebola virus

<400> SEQUENCE: 15
atggatcctc gtccaatcag aacctggatg atgcataaca catctgaagt tgaagcagac        60
taccataaga ttctaactgc cggattgtcc gtccagcaag gcattgtgag acaaagaatc       120
attcctgttt accaaatctc aaacctggag gaagtatgtc aactcatcat acaggcattc       180
gaggctggcg tcgacttcca ggatagtgca gatagctttt tgttaatgct atgtctgcat       240
catgcctatc aaggggatta taaacaattt ttggaaagta atgcggtaaa ataccttgaa       300
ggtcatggat ccgttttga gatgaagaaa aggaaggtg tcaagcgcct ggaggaacta       360
ctccctgctg cctcgagtgg aaagaacatc aagagaacat ggctgcaat gcccgaggag       420 gaaacaacag aagcaaatgc tggacaattt ctttcatttg ctagtctgtt tctcccaaaa       480
```

```
ttggttgtcg gagaaaaggc ctgtctggag aaggttcaac gacaaatcca agtgcacgca    540
gaacaaggtc tgattcaata cccgacatct tggcaatcgg tgggacatat gatggtcatc    600
ttcagactaa tgcgaaccaa cttcctgatt aagttcctcc taatacatca aggaatgcat    660
atggttgcag gcatgatgc taatgatgcc gtcattgcca actctgtagc tcaagctcgt    720
ttctccggat tgttgatagt caaaacagtg cttgatcata tcctccaaaa aacagagcac    780
ggagttcgcc tgcatccctt ggcgcgaaca gccaaagtca aaatgaggt gagctctttt    840 aaggccgctt tagcctcact agcacaacat ggagaatatg cccgtttgc tcgtctgctg    900 aatctatctg gggttaataa tcttgagcat gggcttttcc ctcaactttc tgcaattgct    960
ttgggagtag caactgcaca tgggagcact ctggctggag tcaatgtagg agagcaatac   1020
caacaactgc gagaagcagc cactgaggcc gaaaagcagt tgcagaaata tgctgaatct   1080
cgtgaacttg atcacctagg tcttgatgat caggaaaaga aaatcctaaa agacttccat   1140
cagaaaaaga atgagatcag cttccagcag acgacagcca tggtcacact gcggaaagag   1200
agattggcca aattgaccga agctattact tccacctcta tcctcaaaac aggaaggcgg   1260
tatgatgatg acaatgatat acccttccca gggccaatca atgataacga aactctggt   1320 cagaacgatg acgatccaac agactcccag gataccacaa tcccggatgt aataatcgat   1380
ccaaacgatg gtgggtataa taattacagc gattatgcaa atgatgctgc aagtgctcct   1440
gatgacctag ttcttttga ccttgaggac gaggatgatg ctgataaccc ggctcaaaac   1500
acgccagaaa aaaatgatag accagcaaca acaaagctga aaatggaca ggaccaggat   1560 ggaaaccaag gcgaaactgc atccccacgg gtagccccca accaatacag agacaagcca   1620
atgccacaag tacaggacag atccgaaaat catgaccaaa cccttcaaac acagtccagg   1680
gttttgactc ctatcagcga ggaagcagac cccagcgacc acaacgatgg tgacaatgaa   1740
agcattcctc ccctggaatc agacgacgag ggtagcactg atactactgc agcagaaaca   1800
aagcctgcca ctgcacctcc cgctcccgtc taccgaagta tctccgtaga tgattctgtc   1860
ccctcagaga acattcccgc acagtccaat caaacgaaca tgaggacaa tgtcaggaac   1920 aatgctcagt cggagcaatc cattgcagaa atgtatcaac atatcttgaa acacaagga   1980 ccttttgatg ccatcctta ctaccatatg atgaaagaag agccatcat tttcagcact   2040 agtgatggga aggagtatac atatccgac tctcttgaag atgagtatcc accctggctc   2100
agcgagaagg aagccatgaa cgaagacaat agattcataa ccatggatgg tcagcagttt   2160
tactggcctg tgatgaatca tagaaataaa ttcatggcaa tcctccagca tcacaggtga   2220
```

<210> SEQ ID NO 16
<211> LENGTH: 739
<212> TYPE: PRT
<213> ORGANISM: Ebola virus

<400> SEQUENCE: 16

```
Met Asp Pro Arg Pro Ile Arg Thr Trp Met Met His Asn Thr Ser Glu
1               5                  10                  15

Val Glu Ala Asp Tyr His Lys Ile Leu Thr Ala Gly Leu Ser Val Gln
            20                  25                  30

Gln Gly Ile Val Arg Gln Arg Ile Ile Pro Val Tyr Gln Ile Ser Asn
        35                  40                  45

Leu Glu Glu Val Cys Gln Leu Ile Ile Gln Ala Phe Glu Ala Gly Val
    50                  55                  60
```

-continued

```
Asp Phe Gln Asp Ser Ala Asp Ser Phe Leu Met Leu Cys Leu His
 65                  70                  75                  80

His Ala Tyr Gln Gly Asp Tyr Lys Gln Phe Leu Glu Ser Asn Ala Val
                 85                  90                  95

Lys Tyr Leu Glu Gly His Gly Phe Arg Phe Glu Met Lys Lys Lys Glu
            100                 105                 110

Gly Val Lys Arg Leu Glu Glu Leu Leu Pro Ala Ala Ser Ser Gly Lys
        115                 120                 125

Asn Ile Lys Arg Thr Leu Ala Ala Met Pro Glu Glu Thr Thr Glu
130                 135                 140

Ala Asn Ala Gly Gln Phe Leu Ser Phe Ala Ser Leu Phe Leu Pro Lys
145                 150                 155                 160

Leu Val Val Gly Glu Lys Ala Cys Leu Glu Lys Val Gln Arg Gln Ile
                165                 170                 175

Gln Val His Ala Glu Gln Gly Leu Ile Gln Tyr Pro Thr Ser Trp Gln
            180                 185                 190

Ser Val Gly His Met Met Val Ile Phe Arg Leu Met Arg Thr Asn Phe
        195                 200                 205

Leu Ile Lys Phe Leu Leu Ile His Gln Gly Met His Met Val Ala Gly
210                 215                 220

His Asp Ala Asn Asp Ala Val Ile Ala Asn Ser Val Ala Gln Ala Arg
225                 230                 235                 240

Phe Ser Gly Leu Leu Ile Val Lys Thr Val Leu Asp His Ile Leu Gln
                245                 250                 255

Lys Thr Glu His Gly Val Arg Leu His Pro Leu Ala Arg Thr Ala Lys
            260                 265                 270

Val Lys Asn Glu Val Ser Ser Phe Lys Ala Ala Leu Ala Ser Leu Ala
        275                 280                 285

Gln His Gly Glu Tyr Ala Pro Phe Ala Arg Leu Leu Asn Leu Ser Gly
290                 295                 300

Val Asn Asn Leu Glu His Gly Leu Phe Pro Gln Leu Ser Ala Ile Ala
305                 310                 315                 320

Leu Gly Val Ala Thr Ala His Gly Ser Thr Leu Ala Gly Val Asn Val
                325                 330                 335

Gly Glu Gln Tyr Gln Gln Leu Arg Glu Ala Ala Thr Glu Ala Glu Lys
            340                 345                 350

Gln Leu Gln Lys Tyr Ala Glu Ser Arg Glu Leu Asp His Leu Gly Leu
        355                 360                 365

Asp Asp Gln Glu Lys Lys Ile Leu Lys Asp Phe His Gln Lys Asn
370                 375                 380

Glu Ile Ser Phe Gln Gln Thr Thr Ala Met Val Thr Leu Arg Lys Glu
385                 390                 395                 400

Arg Leu Ala Lys Leu Thr Glu Ala Ile Thr Ser Thr Ile Leu Lys
                405                 410                 415

Thr Gly Arg Arg Tyr Asp Asp Asp Asn Asp Ile Pro Phe Pro Gly Pro
            420                 425                 430

Ile Asn Asp Asn Glu Asn Ser Gly Gln Asn Asp Asp Pro Thr Asp
        435                 440                 445

Ser Gln Asp Thr Thr Ile Pro Asp Val Ile Asp Pro Asn Asp Gly
450                 455                 460

Gly Tyr Asn Asn Tyr Ser Asp Tyr Ala Asn Asp Ala Ala Ser Ala Pro
465                 470                 475                 480

Asp Asp Leu Val Leu Phe Asp Leu Glu Asp Glu Asp Ala Asp Asn
```

```
                485                 490                 495
Pro Ala Gln Asn Thr Pro Glu Lys Asn Asp Arg Pro Ala Thr Thr Lys
            500                 505                 510
Leu Arg Asn Gly Gln Asp Gln Asp Gly Asn Gln Gly Glu Thr Ala Ser
            515                 520                 525
Pro Arg Val Ala Pro Asn Gln Tyr Arg Asp Lys Pro Met Pro Gln Val
            530                 535                 540
Gln Asp Arg Ser Glu Asn His Asp Gln Thr Leu Gln Thr Gln Ser Arg
545                 550                 555                 560
Val Leu Thr Pro Ile Ser Glu Glu Ala Asp Pro Ser Asp His Asn Asp
                565                 570                 575
Gly Asp Asn Glu Ser Ile Pro Pro Leu Glu Ser Asp Asp Glu Gly Ser
            580                 585                 590
Thr Asp Thr Thr Ala Ala Glu Thr Lys Pro Ala Thr Ala Pro Pro Ala
            595                 600                 605
Pro Val Tyr Arg Ser Ile Ser Val Asp Asp Ser Val Pro Ser Glu Asn
            610                 615                 620
Ile Pro Ala Gln Ser Asn Gln Thr Asn Asn Glu Asp Asn Val Arg Asn
625                 630                 635                 640
Asn Ala Gln Ser Glu Gln Ser Ile Ala Glu Met Tyr Gln His Ile Leu
                645                 650                 655
Lys Thr Gln Gly Pro Phe Asp Ala Ile Leu Tyr Tyr His Met Met Lys
            660                 665                 670
Glu Glu Pro Ile Ile Phe Ser Thr Ser Asp Gly Lys Glu Tyr Thr Tyr
            675                 680                 685
Pro Asp Ser Leu Glu Asp Glu Tyr Pro Pro Trp Leu Ser Glu Lys Glu
            690                 695                 700
Ala Met Asn Glu Asp Asn Arg Phe Ile Thr Met Asp Gly Gln Gln Phe
705                 710                 715                 720
Tyr Trp Pro Val Met Asn His Arg Asn Lys Phe Met Ala Ile Leu Gln
                725                 730                 735
His His Arg

<210> SEQ ID NO 17
<211> LENGTH: 465
<212> TYPE: DNA
<213> ORGANISM: Ebola virus

<400> SEQUENCE: 17
agagcccagg atccaggtag caaccagaag acgaaggtca ctcccaccag cttcgccaac      60
aaccaaacct ccaagaacca cgaagacttg gttccagagg atcccgcttc agtggttcaa     120
gtgcgagacc tccagaggga aaacacagtg ccgaccccac cccagacac agtccccaca     180 actctgatcc ccgacacaat ggaggaacaa accaccagcc actacgaacc accaaacatt     240
tccagaaacc atcaagagag gaacaacacc gcacaccccg aaactctcgc caacaatccc     300
ccagacaaca caaccccgtc gacaccacct caagacggtg agcggacaag ttcccacaca     360
acaccctccc ccgcccagt cccaaccagc acaatccatc ccaccacgcg agagactcac     420
attcccacca caatgacaac aagccatgac accgacagct agtag                     465

<210> SEQ ID NO 18
<211> LENGTH: 153
<212> TYPE: PRT
<213> ORGANISM: Ebola virus
```

<400> SEQUENCE: 18

```
Arg Ala Gln Asp Pro Gly Ser Asn Gln Lys Thr Lys Val Thr Pro Thr
1               5                   10                  15

Ser Phe Ala Asn Asn Gln Thr Ser Lys Asn His Glu Asp Leu Val Pro
            20                  25                  30

Glu Asp Pro Ala Ser Val Val Gln Val Arg Asp Leu Gln Arg Glu Asn
        35                  40                  45

Thr Val Pro Thr Pro Pro Asp Thr Val Pro Thr Thr Leu Ile Pro
    50                  55                  60

Asp Thr Met Glu Glu Gln Thr Thr Ser His Tyr Glu Pro Pro Asn Ile
65              70                  75                  80

Ser Arg Asn His Gln Glu Arg Asn Asn Thr Ala His Pro Glu Thr Leu
            85                  90                  95

Ala Asn Asn Pro Pro Asp Asn Thr Thr Pro Ser Thr Pro Pro Gln Asp
            100                 105                 110

Gly Glu Arg Thr Ser Ser His Thr Thr Pro Ser Pro Arg Pro Val Pro
            115                 120                 125

Thr Ser Thr Ile His Pro Thr Thr Arg Glu Thr His Ile Pro Thr Thr
    130                 135                 140

Met Thr Thr Ser His Asp Thr Asp Ser
145                 150
```

<210> SEQ ID NO 19
<211> LENGTH: 981
<212> TYPE: DNA
<213> ORGANISM: Ebola virus

<400> SEQUENCE: 19

```
atgaggagaa tcatcctacc cacggcacca cctgaataca tggaggctgt ttacccaatg      60
agaacaatga attctggtgc agacaacact gccagtggcc ctaattacac aacaactggt     120
gtgatgacaa atgatactcc ctctaattca ctccgaccag ttgcagatga taatattgat     180
catccgagcc acacgcctaa cagtgttgcc tctgcattta tattggaagc tatggtgaat     240
gtaatatctg gcccgaaagt gctgatgaag caaatcccaa tctggcttcc tctgggtgtc     300
tctgaccaga gacatatag cttttgattca accactgctg ccattatgct agcatcatat     360
accatcactc attttggcaa aacctcaaat cccttgtga gaatcaaccg acttggtcct     420
ggcatacctg atcacccact acgactccta agaataggaa atcaagcctt cctacaagag     480
tttgtgctac ctcctgtaca actgccacaa tacttcactt ttgatctgac agcgctgaag     540
ctgatcaccc agccactccc agcggcaacc tggacagatg aaactccagc tgtgtcaact     600
ggcacgctcc gcccagggat ctcattccat cccaaattaa ggcctatcct gctaccagga     660
agagctggaa agaagggctc caactccgat ctaacatctc ctgacaaaat ccaggctata     720
atgaatttcc tacaagacct caaaattgta ccaatcgatc caaccaagaa tatcatgggt     780
attgaagtgc agaactcct ggttcacagg ctgactggga agaagacaac taccaagaat     840
ggtcaaccaa tcattccaat tctgctacca agtacattg gtcttgatcc tctatctcaa     900
ggtgatctca atggtgat cactcaggac tgtgattcct gccactcccc ggccagtctt     960
cccccagtca atgaaaaatg a                                              981
```

<210> SEQ ID NO 20
<211> LENGTH: 326
<212> TYPE: PRT
<213> ORGANISM: Ebola virus

<400> SEQUENCE: 20

| | | | | | | | | | | | | | | |
|---|---|---|---|---|---|---|---|---|---|---|---|---|---|---|
|Met|Arg|Arg|Ile|Ile|Leu|Pro|Thr|Ala|Pro|Glu|Tyr|Met|Glu|Ala|
|1| | | |5| | | | |10| | | | |15|
|Val|Tyr|Pro|Met|Arg|Thr|Met|Asn|Ser|Gly|Ala|Asp|Asn|Thr|Ala|Ser|
| | | | |20| | | | |25| | | | |30|
|Gly|Pro|Asn|Tyr|Thr|Thr|Thr|Gly|Val|Met|Thr|Asn|Asp|Thr|Pro|Ser|
| | | | |35| | | | |40| | | | |45|
|Asn|Ser|Leu|Arg|Pro|Val|Ala|Asp|Asp|Asn|Ile|Asp|His|Pro|Ser|His|
| |50| | | | |55| | | | |60| | | |
|Thr|Pro|Asn|Ser|Val|Ala|Ser|Ala|Phe|Ile|Leu|Glu|Ala|Met|Val|Asn|
|65| | | | |70| | | | |75| | | | |80|
|Val|Ile|Ser|Gly|Pro|Lys|Val|Leu|Met|Lys|Gln|Ile|Pro|Ile|Trp|Leu|
| | | | |85| | | | |90| | | | |95| |
|Pro|Leu|Gly|Val|Ser|Asp|Gln|Lys|Thr|Tyr|Ser|Phe|Asp|Ser|Thr|Thr|
| | | |100| | | | |105| | | | |110| | |
|Ala|Ala|Ile|Met|Leu|Ala|Ser|Tyr|Thr|Ile|Thr|His|Phe|Gly|Lys|Thr|
| | | |115| | | | |120| | | | |125| | |
|Ser|Asn|Pro|Leu|Val|Arg|Ile|Asn|Arg|Leu|Gly|Pro|Gly|Ile|Pro|Asp|
| |130| | | | |135| | | | |140| | | | |
|His|Pro|Leu|Arg|Leu|Leu|Arg|Ile|Gly|Asn|Gln|Ala|Phe|Leu|Gln|Glu|
|145| | | | |150| | | | |155| | | | |160|
|Phe|Val|Leu|Pro|Pro|Val|Gln|Leu|Pro|Gln|Tyr|Phe|Thr|Phe|Asp|Leu|
| | | | |165| | | | |170| | | | |175| |
|Thr|Ala|Leu|Lys|Leu|Ile|Thr|Gln|Pro|Leu|Pro|Ala|Ala|Thr|Trp|Thr|
| | | |180| | | | |185| | | | |190| | |
|Asp|Glu|Thr|Pro|Ala|Val|Ser|Thr|Gly|Thr|Leu|Arg|Pro|Gly|Ile|Ser|
| | | |195| | | | |200| | | | |205| | |
|Phe|His|Pro|Lys|Leu|Arg|Pro|Ile|Leu|Leu|Pro|Gly|Arg|Ala|Gly|Lys|
| | | |210| | | | |215| | | | |220| | |
|Lys|Gly|Ser|Asn|Ser|Asp|Leu|Thr|Ser|Pro|Asp|Lys|Ile|Gln|Ala|Ile|
|225| | | | |230| | | | |235| | | | |240|
|Met|Asn|Phe|Leu|Gln|Asp|Leu|Lys|Ile|Val|Pro|Ile|Asp|Pro|Thr|Lys|
| | | | |245| | | | |250| | | | |255| |
|Asn|Ile|Met|Gly|Ile|Glu|Val|Pro|Glu|Leu|Leu|Val|His|Arg|Leu|Thr|
| | | |260| | | | |265| | | | |270| | |
|Gly|Lys|Lys|Thr|Thr|Thr|Lys|Asn|Gly|Gln|Pro|Ile|Ile|Pro|Ile|Leu|
| | | |275| | | | |280| | | | |285| | |
|Leu|Pro|Lys|Tyr|Ile|Gly|Leu|Asp|Pro|Leu|Ser|Gln|Gly|Asp|Leu|Thr|
| |290| | | | |295| | | | |300| | | | |
|Met|Val|Ile|Thr|Gln|Asp|Cys|Asp|Ser|Cys|His|Ser|Pro|Ala|Ser|Leu|
|305| | | | |310| | | | |315| | | | |320|
|Pro|Pro|Val|Asn|Glu|Lys|
| | | |325| | |

<210> SEQ ID NO 21
<211> LENGTH: 2220
<212> TYPE: DNA
<213> ORGANISM: Ebola virus

<400> SEQUENCE: 21

```
atggagagtc gggcccacaa agcatggatg acgcacaccg catcaggttt cgaaacagat      60
taccataaga ttttaacagc aggattgtca gtccaacaag gcattgtgag acaacgggtc     120
attcaagtcc accaggttac aaacctagaa gaaatatgcc aattgatcat tcaagccttt    180
```

```
gaagctggtg ttgattttca agagagtgca gacagtttct tgctgatgct atgtttacat    240
catgcttatc agggtgacta caagcaattc ttggaaagca atgcagtcaa gtaccttgag    300
ggtcatggct ttcgctttga ggtcaggaaa aaggaaggag tcaagcgact cgaagaattg    360
cttcctgctg catccagtgg caagagcatc aggagaacac tggctgcaat gcctgaagag    420
gagacaacag aagcaaatgc cggacagttc ctctcttttg ctagcttatt tcttcctaag    480
ctagttgtcg gagaaaaagc ctgtctagaa aaggtgcagc ggcaaattca agttcattct    540
gagcagggat tgatccaata ccccacagcc tggcagtcag ttggacacat gatggtcatt    600
ttcagactga tgaaacaaa ttttctaatt aagttcctcc ttatacatca agggatgcat    660
atggtagcag acacgatgc taacgatgct gtcatcgcaa actctgtagc tcaagcacgt    720
ttttcaggat tattgatcgt taaaacagtg ctagatcaca tccttcagaa aacagagcac    780
ggagtgcgtc ttcatccttt ggcaagaact gctaaggtca gaacgaagt aaattccttt    840 aaggctgccc ttagctcgct agcacaacat ggagagtatg ctccttttgc tcgcttgctg    900
aatctttctg gagtcaacaa tctcgagcac ggactgtttc ctcagctttc tgcaattgcc    960
ctaggtgtcg caacggcaca cggcagtacc ctggcaggag taaatgtggg ggaacagtat   1020
cagcaactac gagaagcagc cactgaggca gaaaaacaat gcagaaata cgctgaatct   1080 cgcgagcttg accatctagg tctcgatgat caagagaaga gatcttgaa agacttccat   1140 cagaagaaaa atgaaatcag cttccagcag acaacagcca tggtcacact acggaaggaa   1200
aggctagcca agctcactga ggcaatcacc tccacatccc ttctcaagac aggaaaacag   1260
tatgatgatg acaacgatat cccctttcct gggcccatca tgataacga aaactcagaa   1320 cagcaagacg atgatccaac agattctcag gacactacca tccctgatat cattgttgac   1380
ccggatgatg gcagatacaa caattatgga gactatccta gtgagacggc gaatgcccct   1440
gaagaccttg ttcttttga ccttgaagat ggtgacgagg atgatcaccg accgtcaagt   1500
tcatcagaga caacaacaa acacagtctt acaggaactg acagtaacaa acaagtaac   1560 tggaatcgaa acccgactaa tatgccaaag aaagactcca cacaaaacaa tgacaatcct   1620
gcacagcggg ctcaagaata cgccagggat aacatccagg atacaccaac accccatcga   1680
gctctaactc ccatcagcga agaaaccggc tccaatggtc acaatgaaga tgacattgat   1740
agcatccctc ctttggaatc agacgaagaa acaacactg acaaccat taccaccaca   1800 aaaaatacca ctgctccacc agcacctgtt tatcggagta attcagaaaa ggagcccctc   1860
ccgcaagaaa atcccagaa gcaaccaaac caagtgagtg gtagtgagaa taccgacaat   1920
aaacctcact cagagcaatc agtggaagaa atgtatcgac acatcctcca aacacaagga   1980
ccatttgatg ccatcctata ctattacatg atgacggagg agccgattgt ctttagcact   2040
agtgatggga agaatacgt ataccctgat tctcttgaag gggagcatcc accgtggctc   2100
agtgaaaaag aggccttgaa tgaggacaat aggtttatca caatggatga tcaacaattc   2160
tactggcctg taatgaatca caggaacaaa ttcatggcta tccttcagca ccacaagtaa   2220
```

<210> SEQ ID NO 22
<211> LENGTH: 739
<212> TYPE: PRT
<213> ORGANISM: Ebola virus

<400> SEQUENCE: 22

Met Glu Ser Arg Ala His Lys Ala Trp Met Thr His Thr Ala Ser Gly
1               5                   10                  15

```
Phe Glu Thr Asp Tyr His Lys Ile Leu Thr Ala Gly Leu Ser Val Gln
             20                  25                  30

Gln Gly Ile Val Arg Gln Arg Val Ile Gln Val His Gln Val Thr Asn
         35                  40                  45

Leu Glu Glu Ile Cys Gln Leu Ile Ile Gln Ala Phe Glu Ala Gly Val
 50                  55                  60

Asp Phe Gln Glu Ser Ala Asp Ser Phe Leu Leu Met Leu Cys Leu His
 65                  70                  75                  80

His Ala Tyr Gln Gly Asp Tyr Lys Gln Phe Leu Glu Ser Asn Ala Val
                 85                  90                  95

Lys Tyr Leu Glu Gly His Gly Phe Arg Phe Glu Val Arg Lys Lys Glu
            100                 105                 110

Gly Val Lys Arg Leu Glu Glu Leu Pro Ala Ala Ser Ser Gly Lys
        115                 120                 125

Ser Ile Arg Arg Thr Leu Ala Ala Met Pro Glu Glu Thr Thr Glu
130                 135                 140

Ala Asn Ala Gly Gln Phe Leu Ser Phe Ala Ser Leu Phe Leu Pro Lys
145                 150                 155                 160

Leu Val Val Gly Glu Lys Ala Cys Leu Glu Lys Val Gln Arg Gln Ile
                165                 170                 175

Gln Val His Ser Glu Gln Gly Leu Ile Gln Tyr Pro Thr Ala Trp Gln
            180                 185                 190

Ser Val Gly His Met Met Val Ile Phe Arg Leu Met Arg Thr Asn Phe
        195                 200                 205

Leu Ile Lys Phe Leu Leu Ile His Gln Gly Met His Met Val Ala Gly
210                 215                 220

His Asp Ala Asn Asp Ala Val Ile Ala Asn Ser Val Ala Gln Ala Arg
225                 230                 235                 240

Phe Ser Gly Leu Leu Ile Val Lys Thr Val Leu Asp His Ile Leu Gln
                245                 250                 255

Lys Thr Glu His Gly Val Arg Leu His Pro Leu Ala Arg Thr Ala Lys
            260                 265                 270

Val Lys Asn Glu Val Asn Ser Phe Lys Ala Ala Leu Ser Ser Leu Ala
        275                 280                 285

Gln His Gly Glu Tyr Ala Pro Phe Ala Arg Leu Leu Asn Leu Ser Gly
290                 295                 300

Val Asn Asn Leu Glu His Gly Leu Phe Pro Gln Leu Ser Ala Ile Ala
305                 310                 315                 320

Leu Gly Val Ala Thr Ala His Gly Ser Thr Leu Ala Gly Val Asn Val
                325                 330                 335

Gly Glu Gln Tyr Gln Gln Leu Arg Glu Ala Ala Thr Glu Ala Glu Lys
            340                 345                 350

Gln Leu Gln Lys Tyr Ala Glu Ser Arg Glu Leu Asp His Leu Gly Leu
        355                 360                 365

Asp Asp Gln Glu Lys Lys Ile Leu Lys Asp Phe His Gln Lys Lys Asn
370                 375                 380

Glu Ile Ser Phe Gln Gln Thr Thr Ala Met Val Thr Leu Arg Lys Glu
385                 390                 395                 400

Arg Leu Ala Lys Leu Thr Glu Ala Ile Thr Ser Ser Leu Leu Lys
                405                 410                 415

Thr Gly Lys Gln Tyr Asp Asp Asp Asn Asp Ile Pro Phe Pro Gly Pro
            420                 425                 430
```

```
Ile Asn Asp Asn Glu Asn Ser Glu Gln Gln Asp Asp Pro Thr Asp
            435                 440                 445

Ser Gln Asp Thr Thr Ile Pro Asp Ile Ile Val Asp Pro Asp Gly
    450                 455                 460

Arg Tyr Asn Asn Tyr Gly Asp Tyr Pro Ser Glu Thr Ala Asn Ala Pro
465                 470                 475                 480

Glu Asp Leu Val Leu Phe Asp Leu Glu Asp Gly Asp Glu Asp His
                485                 490                 495

Arg Pro Ser Ser Ser Glu Asn Asn Lys His Ser Leu Thr Gly
            500                 505                 510

Thr Asp Ser Asn Lys Thr Ser Asn Trp Asn Arg Asn Pro Thr Asn Met
            515                 520                 525

Pro Lys Lys Asp Ser Thr Gln Asn Asn Asp Asn Pro Ala Gln Arg Ala
            530                 535                 540

Gln Glu Tyr Ala Arg Asp Asn Ile Gln Asp Thr Pro Thr Pro His Arg
545                 550                 555                 560

Ala Leu Thr Pro Ile Ser Glu Glu Thr Gly Ser Asn Gly His Asn Glu
                565                 570                 575

Asp Asp Ile Asp Ser Ile Pro Pro Leu Glu Ser Asp Glu Glu Asn Asn
                580                 585                 590

Thr Glu Thr Thr Ile Thr Thr Thr Lys Asn Thr Thr Ala Pro Pro Ala
                595                 600                 605

Pro Val Tyr Arg Ser Asn Ser Glu Lys Glu Pro Leu Pro Gln Glu Lys
            610                 615                 620

Ser Gln Lys Gln Pro Asn Gln Val Ser Gly Ser Glu Asn Thr Asp Asn
625                 630                 635                 640

Lys Pro His Ser Glu Gln Ser Val Glu Glu Met Tyr Arg His Ile Leu
                645                 650                 655

Gln Thr Gln Gly Pro Phe Asp Ala Ile Leu Tyr Tyr Tyr Met Met Thr
            660                 665                 670

Glu Glu Pro Ile Val Phe Ser Thr Ser Asp Gly Lys Glu Tyr Val Tyr
            675                 680                 685

Pro Asp Ser Leu Glu Gly Glu His Pro Pro Trp Leu Ser Glu Lys Glu
690                 695                 700

Ala Leu Asn Glu Asp Asn Arg Phe Ile Thr Met Asp Gln Gln Phe
705                 710                 715                 720

Tyr Trp Pro Val Met Asn His Arg Asn Lys Phe Met Ala Ile Leu Gln
                725                 730                 735

His His Lys

<210> SEQ ID NO 23
<211> LENGTH: 465
<212> TYPE: DNA
<213> ORGANISM: Ebola virus

<400> SEQUENCE: 23
gaaacccaga accaggtcct tgacacgaca gcgacggtct ctcctcccat ctccgcccac    60
aaccacgcag ccgaagacca caagaattg gtttcagagg attccactcc agtggttcag    120
atgcaaaaca tcaagggaaa ggacacaatg ccaaccacag tgacgggtgt accaacaacc    180
acaccctctc catttccaat caatgctcgc aacactgatc ataccaaatc atttatcggc    240 ctggagggc cccaagaaga ccacagcacc acacagcctg ccaagaccac agccaacca    300 accaacagca cagaatcgac gacactaaac ccaacatcag agccctccag tagaggcacg    360
```

| | | |
|---|---|---|
| ggaccatcca gccccacggt ccccaacacc acagaaagcc acgccgaact tggcaagaca | | 420 |
| accccaacca cactcccaga acagcacact gccgccagtt agtag | | 465 |

<210> SEQ ID NO 24
<211> LENGTH: 153
<212> TYPE: PRT
<213> ORGANISM: Ebola virus

<400> SEQUENCE: 24

Glu Thr Gln Asn Gln Val Leu Asp Thr Thr Ala Thr Val Ser Pro Pro
1               5                   10                  15

Ile Ser Ala His Asn His Ala Ala Glu Asp His Lys Glu Leu Val Ser
            20                  25                  30

Glu Asp Ser Thr Pro Val Val Gln Met Gln Asn Ile Lys Gly Lys Asp
        35                  40                  45

Thr Met Pro Thr Thr Val Thr Gly Val Pro Thr Thr Thr Pro Ser Pro
    50                  55                  60

Phe Pro Ile Asn Ala Arg Asn Thr Asp His Thr Lys Ser Phe Ile Gly
65                  70                  75                  80

Leu Glu Gly Pro Gln Glu Asp His Ser Thr Thr Gln Pro Ala Lys Thr
                85                  90                  95

Thr Ser Gln Pro Thr Asn Ser Thr Glu Ser Thr Thr Leu Asn Pro Thr
            100                 105                 110

Ser Glu Pro Ser Ser Arg Gly Thr Gly Pro Ser Ser Pro Thr Val Pro
        115                 120                 125

Asn Thr Thr Glu Ser His Ala Glu Leu Gly Lys Thr Thr Pro Thr Thr
    130                 135                 140

Leu Pro Glu Gln His Thr Ala Ala Ser
145                 150

<210> SEQ ID NO 25
<211> LENGTH: 996
<212> TYPE: DNA
<213> ORGANISM: Ebola virus

<400> SEQUENCE: 25

| | | |
|---|---|---|
| atgagacgcg gagtgttacc aacggctcct ccagcatata tgatatttgc atacctatg | | 60 |
| agcatactcc caacccgacc aagtgtcata gtcaatgaga ccaaatcaga tgtactggca | | 120 |
| gtgccagggg cagatgttcc atcaaactcc atgagaccag tggctgatga taacattgat | | 180 |
| cactcaagcc atactccaag cggagtagct tctgccttta tattggaagc tacagtgaat | | 240 |
| gtaatttcgg gaacaaaagt cctgatgaag caaatacccta tttggcttcc actgggtgta | | 300 |
| gctgatcaga gatatacag ctttgattca acaacagccg caattatgtt ggcttcctac | | 360 |
| acagtgacac acttcgggaa gatatctaac ccgctggtac gtgtcaacag gctaggccca | | 420 |
| ggaatacccg atcatcccgct acgactccta aggttgggca atcaggcatt ccttcaagag | | 480 |
| tttgttcttc caccagtcca gcttccccag tatttcacat tgatctaac agctctaaag | | 540 |
| ctcatcactc aaccattgcc agctgcaacc tggacagacg aaactccagc aggagcagtc | | 600 |
| aatgctcttc gtcctgggct ctcactccat cccaagcttc gtccaattct cctgccgggg | | 660 |
| aagacaggaa agaaaggaca tgcttcagac ttaacatcac ctgacaagat tcaaacaatc | | 720 |
| atgaatgcaa taccggacct caaaattgtc ccgattgatc caaccaagaa catagttgga | | 780 |
| attgaggttc cagaattact agttcaaagg ctgaccggga aaaaaccaca acccaaaaat | | 840 |
| ggccaaccaa ttattccagt tcttcttccg aaatatgttg gacttgatcc tatatcgcca | | 900 |

```
ggggacttaa ctatggttat cacccaggat tgtgattcat gccactctcc agccagccat    960
ccgtatcaca tggacaagca ggatagttac caataa                              996
```

<210> SEQ ID NO 26
<211> LENGTH: 331
<212> TYPE: PRT
<213> ORGANISM: Ebola virus

<400> SEQUENCE: 26

```
Met Arg Arg Gly Val Leu Pro Thr Ala Pro Ala Tyr Asn Asp Ile
1               5                   10                  15

Ala Tyr Pro Met Ser Ile Leu Pro Thr Arg Pro Ser Val Ile Val Asn
                20                  25                  30

Glu Thr Lys Ser Asp Val Leu Ala Val Pro Gly Ala Asp Val Pro Ser
            35                  40                  45

Asn Ser Met Arg Pro Val Ala Asp Asp Asn Ile Asp His Ser Ser His
        50                  55                  60

Thr Pro Ser Gly Val Ala Ser Ala Phe Ile Leu Glu Ala Thr Val Asn
65                  70                  75                  80

Val Ile Ser Gly Thr Lys Val Leu Met Lys Gln Ile Pro Ile Trp Leu
                85                  90                  95

Pro Leu Gly Val Ala Asp Gln Lys Ile Tyr Ser Phe Asp Ser Thr Thr
            100                 105                 110

Ala Ala Ile Met Leu Ala Ser Tyr Thr Val Thr His Phe Gly Lys Ile
        115                 120                 125

Ser Asn Pro Leu Val Arg Val Asn Arg Leu Gly Pro Gly Ile Pro Asp
        130                 135                 140

His Pro Leu Arg Leu Leu Arg Leu Gly Asn Gln Ala Phe Leu Gln Glu
145                 150                 155                 160

Phe Val Leu Pro Pro Val Gln Leu Pro Gln Tyr Phe Thr Phe Asp Leu
                165                 170                 175

Thr Ala Leu Lys Leu Ile Thr Gln Pro Leu Pro Ala Ala Thr Trp Thr
            180                 185                 190

Asp Glu Thr Pro Ala Gly Ala Val Asn Ala Leu Arg Pro Gly Leu Ser
        195                 200                 205

Leu His Pro Lys Leu Arg Pro Ile Leu Leu Pro Gly Lys Thr Gly Lys
        210                 215                 220

Lys Gly His Ala Ser Asp Leu Thr Ser Pro Asp Lys Ile Gln Thr Ile
225                 230                 235                 240

Met Asn Ala Ile Pro Asp Leu Lys Ile Val Pro Ile Asp Pro Thr Lys
                245                 250                 255

Asn Ile Val Gly Ile Glu Val Pro Glu Leu Leu Val Gln Arg Leu Thr
            260                 265                 270

Gly Lys Lys Pro Gln Pro Lys Asn Gly Gln Pro Ile Ile Pro Val Leu
        275                 280                 285

Leu Pro Lys Tyr Val Gly Leu Asp Pro Ile Ser Pro Gly Asp Leu Thr
        290                 295                 300

Met Val Ile Thr Gln Asp Cys Asp Ser Cys His Ser Pro Ala Ser His
305                 310                 315                 320

Pro Tyr His Met Asp Lys Gln Asp Ser Tyr Gln
                325                 330
```

<210> SEQ ID NO 27
<211> LENGTH: 2220

<212> TYPE: DNA
<213> ORGANISM: Ebola virus

<400> SEQUENCE: 27

```
atggatcgtg ggaccagaag aatctgggtg tcgcaaaatc aaggtgatac tgatttagat      60
tatcataaaa ttttgacagc tggccttact gttcaacagg gaattgtcag gcagaaaata     120
atttctgtat atcttgttga taacttggag gctatgtgtc aattggtaat acaagccttt     180
gaggccggaa ttgatttcca agaaaatgcc gacagcttcc ttctgatgct ttgcctacat     240
catgcttacc aaggtgacta taaattgttc ttggagagca atgctgtaca gtatttggaa     300
ggtcatggat tcaaatttga gctccggaag aaggacggtg tcaatcggct cgaggaattg     360
cttcctgctg caacgagtgg aaaaaacatc aggcgtacgt tggccgcact gcctgaagag     420
gagactacag aagcaaatgc agggcaattt ctctcatttg cgagtttgtt tcttcccaaa     480
ctggttgtgg gagagaaggc ttgcttggaa aaagtccagc gacaaattca ggttcatgca     540
gaacagggtt taattcaata tcccactgca tggcaatcag ttggacacat gatggtaatc     600
ttcagattga tgaggactaa tttcttgatt aaatatttac tgatccacca gggtatgcat     660
atggtagctg ccacgatgc caatgatgct gtcattgcta attcagttgc tcaggctcgc     720
ttttcaggac tcctaattgt caaaaccgtt cttgatcata ttctgcaaaa aaccgaccaa     780
ggagtaagac ttcacccttt ggcccgaaca gccaaagtgc gtaatgaggt taatgcattt     840
aaggccgccc taagctcact tgctaagcat ggggaatatg cccctttgc tcgccttctc     900
aatctctcgg gagttaacaa cctagaacat ggtctctacc cacagttatc agcaattgct     960
cttggagttg ccacagcaca tggtagcacc cttgcaggag ttaatgttgg tgagcagtat    1020
cagcagctta gagaggctgc cactgaagct gagaagcaac tccaacaata tgctgagtcc    1080
agagaactcg acagcctagg cctggacgat caggaaagaa gaatactaat gaacttccat    1140
cagaagaaaa acgaaattag tttccagcag accaatgcaa tggtaaccct taggaaagag    1200
cgactggcta aattaacaga agctataacg ctggcctcaa gacctaaccct cgggtctaga    1260
caagacgacg gcaatgaaat accgttccct gggcctataa gcaacaaccc agaccaagat    1320
catctggagg atgatcctag agactccaga gacaccatca ttcctaatgg tgcaattgac    1380
cccgaggatg tgattttga aaattacaat ggctatcatg atgatgaagt tgggacggca    1440
ggtgacttgg tcctgttcga tcttgacgat catgaggatg acaataaagc ttttgagcca    1500
caggacagct cgccacaatc ccaaagggaa atagagagag aaagattaat tcatccaccc    1560
ccaggcaaca caaggacga caatcgagcc tcagacaaca atcaacaatc agcagattct    1620
gaggaacaag gaggtcaata caactggcac cgaggcccag aacgtacgac cgccaatcga    1680
agactctcac cagtgcacga agaggacacc cttatggatc aaggcgatga tgatccctca    1740
agcttacctc cgctggaatc tgatgatgac gatgcatcaa gtagccaaca agatccgat    1800
tatacagctg ttgccctcc tgctcctgta taccgcagtg cagaagccca cgagcctccc    1860
cacaaatcct cgaacgagcc agctgaaaca tcacaattga atgaagaccc tgatatcggt    1920
caatcaaagt ctatgcaaaa attagaagag acatatcacc atctgctgag aactcaaggt    1980
ccatttgaag ccatcaatta ttatcacatg atgaaggatg agccggtaat atttagcact    2040
gatgatggga aggaatacac ctacccggat tcacttgagg aagcctatcc tccatggctc    2100
accgagaaag aacgactgga caaagagaat cgctacattt acataaataa tcaacagttc    2160
ttctggcctg tcatgagtcc cagagacaaa tttcttgcaa tcttgcagca ccatcagtaa    2220
```

<210> SEQ ID NO 28
<211> LENGTH: 739
<212> TYPE: PRT
<213> ORGANISM: Ebola virus

<400> SEQUENCE: 28

```
Met Asp Arg Gly Thr Arg Arg Ile Trp Val Ser Gln Asn Gln Gly Asp
1               5                   10                  15

Thr Asp Leu Asp Tyr His Lys Ile Leu Thr Ala Gly Leu Thr Val Gln
            20                  25                  30

Gln Gly Ile Val Arg Gln Lys Ile Ile Ser Val Tyr Leu Val Asp Asn
        35                  40                  45

Leu Glu Ala Met Cys Gln Leu Val Ile Gln Ala Phe Glu Ala Gly Ile
    50                  55                  60

Asp Phe Gln Glu Asn Ala Asp Ser Phe Leu Leu Met Leu Cys Leu His
65                  70                  75                  80

His Ala Tyr Gln Gly Asp Tyr Lys Leu Phe Leu Glu Ser Asn Ala Val
                85                  90                  95

Gln Tyr Leu Glu Gly His Gly Phe Lys Phe Glu Leu Arg Lys Lys Asp
            100                 105                 110

Gly Val Asn Arg Leu Glu Glu Leu Leu Pro Ala Ala Thr Ser Gly Lys
        115                 120                 125

Asn Ile Arg Arg Thr Leu Ala Ala Leu Pro Glu Glu Thr Thr Glu
    130                 135                 140

Ala Asn Ala Gly Gln Phe Leu Ser Phe Ala Ser Leu Phe Leu Pro Lys
145                 150                 155                 160

Leu Val Val Gly Glu Lys Ala Cys Leu Glu Lys Val Gln Arg Gln Ile
                165                 170                 175

Gln Val His Ala Glu Gln Gly Leu Ile Gln Tyr Pro Thr Ala Trp Gln
            180                 185                 190

Ser Val Gly His Met Met Val Ile Phe Arg Leu Met Arg Thr Asn Phe
        195                 200                 205

Leu Ile Lys Tyr Leu Leu Ile His Gln Gly Met His Met Val Ala Gly
    210                 215                 220

His Asp Ala Asn Asp Ala Val Ile Ala Asn Ser Val Ala Gln Ala Arg
225                 230                 235                 240

Phe Ser Gly Leu Leu Ile Val Lys Thr Val Leu Asp His Ile Leu Gln
                245                 250                 255

Lys Thr Asp Gln Gly Val Arg Leu His Pro Leu Ala Arg Thr Ala Lys
            260                 265                 270

Val Arg Asn Glu Val Asn Ala Phe Lys Ala Ala Leu Ser Ser Leu Ala
        275                 280                 285

Lys His Gly Glu Tyr Ala Pro Phe Ala Arg Leu Leu Asn Leu Ser Gly
    290                 295                 300

Val Asn Asn Leu Glu His Gly Leu Tyr Pro Gln Leu Ser Ala Ile Ala
305                 310                 315                 320

Leu Gly Val Ala Thr Ala His Gly Ser Thr Leu Ala Gly Val Asn Val
                325                 330                 335

Gly Glu Gln Tyr Gln Gln Leu Arg Glu Ala Ala Thr Glu Ala Glu Lys
            340                 345                 350

Gln Leu Gln Gln Tyr Ala Glu Ser Arg Glu Leu Asp Ser Leu Gly Leu
        355                 360                 365

Asp Asp Gln Glu Arg Arg Ile Leu Met Asn Phe His Gln Lys Lys Asn
    370                 375                 380
```

Glu Ile Ser Phe Gln Gln Thr Asn Ala Met Val Thr Leu Arg Lys Glu
385                 390                 395                 400

Arg Leu Ala Lys Leu Thr Glu Ala Ile Thr Leu Ala Ser Arg Pro Asn
            405                 410                 415

Leu Gly Ser Arg Gln Asp Asp Gly Asn Glu Ile Pro Phe Pro Gly Pro
        420                 425                 430

Ile Ser Asn Asn Pro Asp Gln Asp His Leu Glu Asp Asp Pro Arg Asp
    435                 440                 445

Ser Arg Asp Thr Ile Ile Pro Asn Gly Ala Ile Asp Pro Glu Asp Gly
450                 455                 460

Asp Phe Glu Asn Tyr Asn Gly Tyr His Asp Glu Val Gly Thr Ala
465                 470                 475                 480

Gly Asp Leu Val Leu Phe Asp Leu Asp Asp His Glu Asp Asn Lys
            485                 490                 495

Ala Phe Glu Pro Gln Asp Ser Ser Pro Gln Ser Gln Arg Glu Ile Glu
        500                 505                 510

Arg Glu Arg Leu Ile His Pro Pro Gly Asn Asn Lys Asp Asp Asn
    515                 520                 525

Arg Ala Ser Asp Asn Asn Gln Gln Ser Ala Asp Ser Glu Glu Gln Gly
530                 535                 540

Gly Gln Tyr Asn Trp His Arg Gly Pro Glu Arg Thr Thr Ala Asn Arg
545                 550                 555                 560

Arg Leu Ser Pro Val His Glu Glu Asp Thr Leu Met Asp Gln Gly Asp
            565                 570                 575

Asp Asp Pro Ser Ser Leu Pro Pro Leu Glu Ser Asp Asp Asp Ala
        580                 585                 590

Ser Ser Ser Gln Gln Asp Pro Asp Tyr Thr Ala Val Ala Pro Pro Ala
    595                 600                 605

Pro Val Tyr Arg Ser Ala Glu Ala His Glu Pro Pro His Lys Ser Ser
610                 615                 620

Asn Glu Pro Ala Glu Thr Ser Gln Leu Asn Glu Asp Pro Asp Ile Gly
625                 630                 635                 640

Gln Ser Lys Ser Met Gln Lys Leu Glu Glu Thr Tyr His His Leu Leu
            645                 650                 655

Arg Thr Gln Gly Pro Phe Glu Ala Ile Asn Tyr Tyr His Met Met Lys
        660                 665                 670

Asp Glu Pro Val Ile Phe Ser Thr Asp Asp Gly Lys Glu Tyr Thr Tyr
    675                 680                 685

Pro Asp Ser Leu Glu Glu Ala Tyr Pro Pro Trp Leu Thr Glu Lys Glu
        690                 695                 700

Arg Leu Asp Lys Glu Asn Arg Tyr Ile Tyr Ile Asn Asn Gln Gln Phe
705                 710                 715                 720

Phe Trp Pro Val Met Ser Pro Arg Asp Lys Phe Leu Ala Ile Leu Gln
            725                 730                 735

His His Gln

<210> SEQ ID NO 29
<211> LENGTH: 465
<212> TYPE: DNA
<213> ORGANISM: Ebola virus

<400> SEQUENCE: 29
acccacacca acaactcctc agatcagagc ccggcgggaa ctgtccaagg aaaaattagc        60

```
taccacccac ccgccaacaa ctccgagctg gttccaacgg attcccctcc agtagtttca    120
gtgctcactg caggacggac agaggaaatg tcgacccaag gtctaaccaa cggagagaca    180
atcacaggtt tcaccgcgaa cccaatgaca accaccattg ccccaagtcc aaccatgaca    240
agcgaggttg ataacaatgt accaagtgaa caaccgaaca acacagcatc cattgaagac    300
tcccccccat cggcaagcaa cgagacaatt taccactccg agatggatcc gatccaaggc    360
tcgaacaact ccgcccagag cccacagacc aagaccacgc cagcacccac aacatccccg    420
atgacccagg acccgcaaga gacggccaac agcagcaaat agtag                    465
```

<210> SEQ ID NO 30
<211> LENGTH: 153
<212> TYPE: PRT
<213> ORGANISM: Ebola virus

<400> SEQUENCE: 30

Thr His Thr Asn Asn Ser Ser Asp Gln Ser Pro Ala Gly Thr Val Gln
1               5                   10                  15

Gly Lys Ile Ser Tyr His Pro Pro Ala Asn Asn Ser Glu Leu Val Pro
            20                  25                  30

Thr Asp Ser Pro Pro Val Val Ser Val Leu Thr Ala Gly Arg Thr Glu
        35                  40                  45

Glu Met Ser Thr Gln Gly Leu Thr Asn Gly Glu Thr Ile Thr Gly Phe
    50                  55                  60

Thr Ala Asn Pro Met Thr Thr Thr Ile Ala Pro Ser Pro Thr Met Thr
65                  70                  75                  80

Ser Glu Val Asp Asn Asn Val Pro Ser Glu Gln Pro Asn Asn Thr Ala
                85                  90                  95

Ser Ile Glu Asp Ser Pro Pro Ser Ala Ser Asn Glu Thr Ile Tyr His
            100                 105                 110

Ser Glu Met Asp Pro Ile Gln Gly Ser Asn Asn Ser Ala Gln Ser Pro
        115                 120                 125

Gln Thr Lys Thr Thr Pro Ala Pro Thr Thr Ser Pro Met Thr Gln Asp
    130                 135                 140

Pro Gln Glu Thr Ala Asn Ser Ser Lys
145                 150

<210> SEQ ID NO 31
<211> LENGTH: 912
<212> TYPE: DNA
<213> ORGANISM: Marburg virus

<400> SEQUENCE: 31

```
atggccagtt ccagcaatta caacacatac atgcaatact tgaaccccccc tccttatgct    60 gatcacggtg caaaccagtt gatcccggcg gatcagctat caaatcagca gggtataact    120
ccaaattacg tgggtgattt aaacctagat gatcagttca agggaatgt ctgccatgct    180 ttcactttag aggcaataat tgacatatct gcatataacg agcgaacagt caaaggcgtt    240
ccggcatggc tgcctcttgg gattatgagc aattttgaat atcctttagc tcatactgtg    300
gccgcgttgc tcacaggcag ctatacaatc acccaattta ctcacaacgg caaaaattc    360 gtccgtgtta atcgacttgg tacaggaatc ccagcacacc cactcagaat gttgcgtgaa    420
ggaaatcaag cttttattca gaatatggtg atccccagga attttcaac taatcaattc    480 acctacaatc tcactaattt agtattgagt gtgcaaaaac ttcctgatga tgcctggcgc    540
ccatccaagg acaaattaat tgggaacact atgcatccg cagtctccat ccacccgaat    600
```

```
ctgccgccta ttgttctacc aacagtcaag aagcaggctt atcgtcagca caaaaatccc      660
aacaatggac cattgctggc catatctggc atcctccatc aactgagggt cgaaaaagtc      720
ccagagaaga cgagcctgtt taggatctcg cttcctgccg acatgttctc agtaaaagag      780
ggtatgatga agaaaagggg agaaaattcc cccgtggttt attttcaagc acctgagaac      840
ttccctttga atggcttcaa taacagacaa gttgtgctag cgtatgcgaa tccaacgctc      900
agtgccgttt ga                                                         912
```

<210> SEQ ID NO 32
<211> LENGTH: 303
<212> TYPE: PRT
<213> ORGANISM: Marburg virus

<400> SEQUENCE: 32

```
Met Ala Ser Ser Ser Asn Tyr Asn Thr Tyr Met Gln Tyr Leu Asn Pro
1               5                   10                  15

Pro Pro Tyr Ala Asp His Gly Ala Asn Gln Leu Ile Pro Ala Asp Gln
            20                  25                  30

Leu Ser Asn Gln Gln Gly Ile Thr Pro Asn Tyr Val Gly Asp Leu Asn
        35                  40                  45

Leu Asp Asp Gln Phe Lys Gly Asn Val Cys His Ala Phe Thr Leu Glu
    50                  55                  60

Ala Ile Ile Asp Ile Ser Ala Tyr Asn Glu Arg Thr Val Lys Gly Val
65                  70                  75                  80

Pro Ala Trp Leu Pro Leu Gly Ile Met Ser Asn Phe Glu Tyr Pro Leu
                85                  90                  95

Ala His Thr Val Ala Ala Leu Leu Thr Gly Ser Tyr Thr Ile Thr Gln
            100                 105                 110

Phe Thr His Asn Gly Gln Lys Phe Val Arg Val Asn Arg Leu Gly Thr
        115                 120                 125

Gly Ile Pro Ala His Pro Leu Arg Met Leu Arg Glu Gly Asn Gln Ala
    130                 135                 140

Phe Ile Gln Asn Met Val Ile Pro Arg Asn Phe Ser Thr Asn Gln Phe
145                 150                 155                 160

Thr Tyr Asn Leu Thr Asn Leu Val Leu Ser Val Gln Lys Leu Pro Asp
                165                 170                 175

Asp Ala Trp Arg Pro Ser Lys Asp Lys Leu Ile Gly Asn Thr Met His
            180                 185                 190

Pro Ala Val Ser Ile His Pro Asn Leu Pro Pro Ile Val Leu Pro Thr
        195                 200                 205

Val Lys Lys Gln Ala Tyr Arg Gln His Lys Asn Pro Asn Asn Gly Pro
    210                 215                 220

Leu Leu Ala Ile Ser Gly Ile Leu His Gln Leu Arg Val Glu Lys Val
225                 230                 235                 240

Pro Glu Lys Thr Ser Leu Phe Arg Ile Ser Leu Pro Ala Asp Met Phe
                245                 250                 255

Ser Val Lys Glu Gly Met Met Lys Lys Arg Gly Glu Asn Ser Pro Val
            260                 265                 270

Val Tyr Phe Gln Ala Pro Glu Asn Phe Pro Leu Asn Gly Phe Asn Asn
        275                 280                 285

Arg Gln Val Val Leu Ala Tyr Ala Asn Pro Thr Leu Ser Ala Val
    290                 295                 300
```

<210> SEQ ID NO 33
<211> LENGTH: 2088
<212> TYPE: DNA
<213> ORGANISM: Marburg virus

<400> SEQUENCE: 33

```
atggatttac acagtttgtt ggagttgggt acaaaaccca ctgcccctca tgttcgtaat      60
aagaaagtga tattatttga cacaaatcat caggttagta tctgtaatca gataatagat     120
gcaataaact cagggattga tcttggagat ctcctagaag ggggtttgct gacgttgtgt     180
gttgagcatt actataattc tgataaggat aaattcaaca caagtcctat cgcgaagtac     240
ttacgtgatg cgggctatga atttgatgtc atcaagaatg cagatgcaac ccgctttctg     300
gatgtgattc ctaatgaacc tcattacagc cctttaattc tagcccttaa gacattggaa     360
agtactgaat ctcagagggg gagaattggg ctcttttat cattttgcag tcttttcctc     420
ccaaaacttg tcgtcggaga ccgagctagt atcgaaaagg ctttaagaca agtaacagtg     480
catcaagaac aggggatcgt cacataccct aatcattggc ttaccacagg ccacatgaaa     540
gtaattttcg ggattttgag gtccagcttc attttaaagt ttgtgttgat tcatcaagga     600
gtaaatttgg tgacaggtca tgatgcctat gacagtatca ttagtaattc agtaggtcaa     660
actagattct caggacttct tatcgtgaaa acagttctcg agttcatctt gcaaaaaact     720
gattcagggg tgacactaca tcctttggtg cggacctcca aagtaaaaaa tgaagttgct     780
agtttcaagc aggcgttgag caacctagcc cgacatgggg aatacgcacc atttgcacgg     840
gttctgaatt tatcagggat taacaacctc gaacatggac tctatcctca gctttcagca     900
attgcgctgg gtgtggcaac agcacacggc agtacattgg ctggtgtcaa tgttggcgaa     960
caatatcaac aactacgaga ggcggcacat gatgcggaag taaaactaca aaggcgacat    1020
gaacatcagg aaattcaagc tattgccgag gatgacgagg aaaggaagat attagaacaa    1080
ttccaccttc agaaaactga atcacacac agtcagacac tagccgtcct cagccagaaa    1140
cgagaaaaat tagctcgtct cgctgcagaa attgaaaaca atattgtgga agatcaggga    1200
tttaagcaat cacagaatcg ggtgtcacag tcgttttttga atgaccctac acctgtggaa    1260
gtaacggttc aagccaggcc catgaatcga ccaactgctc tgcctccccc agttgacgac    1320
aagattgagc atgaatctac agaagatagc tcttcttcaa gtagctttgt tgacttgaat    1380
gatccatttg cactgctgaa tgaggacgag atactcttg atgacagtgt catgatcccg    1440
ggcacaacat cgagagaatt tcaagggatt cctgaaccgc aagacaatc ccaagacctc    1500
aataacagcc aaggaaagca ggaagatgaa tccacaaatc cgattaagaa acagtttctg    1560
agatatcaag aattgcctcc tgttcaagag gatgatgaat cggaatacac aactgactct    1620
caagaaagca tcgaccaacc aggatccgac aatgaacaag gagttgatct tccacctcct    1680
ccgttgtacg ctcaggaaaa aagacaggac ccaatacagc acccagcagc aaaccctcag    1740
gatcccttcg gcagtattgg tgatgtaaat ggtgatatct tagaacctat aagatcacct    1800
tcttcaccat ctgctcctca ggaagacaca aggatgaggg aagcctatga attgtcgcct    1860
gatttcacaa tgatgagga taatcagcag aattggccac aaagagtggt gacaaagaag    1920
ggtagaactt tccttttatcc taatgatctt ctgcaaacaa tcctccaga gtcacttata    1980
acagccctcg ttgaggaata ccaaaatcct gtctcagcta aggagcttca agcagattgg    2040
cccgacatgt catttgatga aaggagacat gttgcgatga acttgtag              2088
```

<210> SEQ ID NO 34

<211> LENGTH: 695
<212> TYPE: PRT
<213> ORGANISM: Marburg virus

<400> SEQUENCE: 34

Met Asp Leu His Ser Leu Glu Leu Gly Thr Lys Pro Thr Ala Pro
1               5                   10                  15

His Val Arg Asn Lys Lys Val Ile Leu Phe Asp Thr Asn His Gln Val
            20                  25                  30

Ser Ile Cys Asn Gln Ile Ile Asp Ala Ile Asn Ser Gly Ile Asp Leu
        35                  40                  45

Gly Asp Leu Leu Glu Gly Gly Leu Leu Thr Leu Cys Val Glu His Tyr
    50                  55                  60

Tyr Asn Ser Asp Lys Asp Lys Phe Asn Thr Ser Pro Ile Ala Lys Tyr
65                  70                  75                  80

Leu Arg Asp Ala Gly Tyr Glu Phe Asp Val Ile Lys Asn Ala Asp Ala
                85                  90                  95

Thr Arg Phe Leu Asp Val Ile Pro Asn Glu Pro His Tyr Ser Pro Leu
            100                 105                 110

Ile Leu Ala Leu Lys Thr Leu Glu Ser Thr Glu Ser Gln Arg Gly Arg
        115                 120                 125

Ile Gly Leu Phe Leu Ser Phe Cys Ser Leu Phe Leu Pro Lys Leu Val
    130                 135                 140

Val Gly Asp Arg Ala Ser Ile Glu Lys Ala Leu Arg Gln Val Thr Val
145                 150                 155                 160

His Gln Glu Gln Gly Ile Val Thr Tyr Pro Asn His Trp Leu Thr Thr
                165                 170                 175

Gly His Met Lys Val Ile Phe Gly Ile Leu Arg Ser Ser Phe Ile Leu
            180                 185                 190

Lys Phe Val Leu Ile His Gln Gly Val Asn Leu Val Thr Gly His Asp
        195                 200                 205

Ala Tyr Asp Ser Ile Ile Ser Asn Ser Val Gly Gln Thr Arg Phe Ser
    210                 215                 220

Gly Leu Leu Ile Val Lys Thr Val Leu Glu Phe Ile Leu Gln Lys Thr
225                 230                 235                 240

Asp Ser Gly Val Thr Leu His Pro Leu Val Arg Thr Ser Lys Val Lys
                245                 250                 255

Asn Glu Val Ala Ser Phe Lys Gln Ala Leu Ser Asn Leu Ala Arg His
            260                 265                 270

Gly Glu Tyr Ala Pro Phe Ala Arg Val Leu Asn Leu Ser Gly Ile Asn
        275                 280                 285

Asn Leu Glu His Gly Leu Tyr Pro Gln Leu Ser Ala Ile Ala Leu Gly
    290                 295                 300

Val Ala Thr Ala His Gly Ser Thr Leu Ala Gly Val Asn Val Gly Glu
305                 310                 315                 320

Gln Tyr Gln Gln Leu Arg Glu Ala Ala His Asp Ala Glu Val Lys Leu
                325                 330                 335

Gln Arg Arg His Glu His Gln Glu Ile Gln Ala Ile Ala Glu Asp Asp
            340                 345                 350

Glu Glu Arg Lys Ile Leu Glu Gln Phe His Leu Gln Lys Thr Glu Ile
        355                 360                 365

Thr His Ser Gln Thr Leu Ala Val Leu Ser Gln Lys Arg Glu Lys Leu
    370                 375                 380

Ala Arg Leu Ala Ala Glu Ile Glu Asn Asn Ile Val Glu Asp Gln Gly

```
                385                 390                 395                 400
        Phe Lys Gln Ser Gln Asn Arg Val Ser Gln Ser Phe Leu Asn Asp Pro
                            405                 410                 415

Thr Pro Val Glu Val Thr Val Gln Ala Arg Pro Met Asn Arg Pro Thr
                            420                 425                 430

Ala Leu Pro Pro Pro Val Asp Lys Ile Glu His Glu Ser Thr Glu
                        435                 440                 445

Asp Ser Ser Ser Ser Ser Phe Val Asp Leu Asn Asp Pro Phe Ala
                    450                 455                 460

Leu Leu Asn Glu Asp Glu Asp Thr Leu Asp Asp Ser Val Met Ile Pro
        465                 470                 475                 480

Gly Thr Thr Ser Arg Glu Phe Gln Gly Ile Pro Glu Pro Pro Arg Gln
                            485                 490                 495

Ser Gln Asp Leu Asn Asn Ser Gln Gly Lys Gln Glu Asp Glu Ser Thr
                        500                 505                 510

Asn Pro Ile Lys Lys Gln Phe Leu Arg Tyr Gln Glu Leu Pro Pro Val
                    515                 520                 525

Gln Glu Asp Asp Glu Ser Glu Tyr Thr Thr Asp Ser Gln Glu Ser Ile
        530                 535                 540

Asp Gln Pro Gly Ser Asp Asn Glu Gln Gly Val Asp Leu Pro Pro Pro
        545                 550                 555                 560

Pro Leu Tyr Ala Gln Glu Lys Arg Gln Asp Pro Ile Gln His Pro Ala
                            565                 570                 575

Ala Asn Pro Gln Asp Pro Phe Gly Ser Ile Gly Asp Val Asn Gly Asp
                        580                 585                 590

Ile Leu Glu Pro Ile Arg Ser Pro Ser Ser Pro Ser Ala Pro Gln Glu
                    595                 600                 605

Asp Thr Arg Met Arg Glu Ala Tyr Glu Leu Ser Pro Asp Phe Thr Asn
        610                 615                 620

Asp Glu Asp Asn Gln Gln Asn Trp Pro Gln Arg Val Val Thr Lys Lys
        625                 630                 635                 640

Gly Arg Thr Phe Leu Tyr Pro Asn Asp Leu Leu Gln Thr Asn Pro Pro
                            645                 650                 655

Glu Ser Leu Ile Thr Ala Leu Val Glu Glu Tyr Gln Asn Pro Val Ser
                        660                 665                 670

Ala Lys Glu Leu Gln Ala Asp Trp Pro Asp Met Ser Phe Asp Glu Arg
                    675                 680                 685

Arg His Val Ala Met Asn Leu
                690                 695

<210> SEQ ID NO 35
<211> LENGTH: 657
<212> TYPE: DNA
<213> ORGANISM: Marburg virus

<400> SEQUENCE: 35
gggctttcat caacaatgcc acccactccc tcaccacaac caagcacgcc acagcaagga      60
ggaaacaaca caaccattc ccaagatgct gtgactgaac ttgacaaaaa taacacaact     120
gcacaaccgt ccatgccccc tcataacact accacaatct ctactaacaa cacctccaaa    180
cacaacttca gcactctctc tgcaccatta caaaacacca ccaatgacaa cacacagagc    240
acaatcactg aaaatgagca aaccagtgcc cctcgataa caaccctgcc tccaacggga     300
aatcccacca cagcaaagag caccagcagc aaaaaaggcc ccgccacaac ggcaccaaac    360
```

-continued

```
acgacaaatg agcatttcac cagtcctccc cccaccccca gctcgactgc acaacatctt    420
gtatatttca gaagaaagcg aagtatcctc tggagggaag gcgacatgtt ccctttcctg    480
gatgggttaa taaatgctcc aattgatttt gacccagttc caaatacaaa aacaatcttt    540
gatgaatcct ctagttctgg tgcctcggct gaggaagatc aacatgcctc ccccaatatt    600
agtttaactt tatcttattt tcctaatata aatgagaaca ctgcctactc ttagtag       657
```

<210> SEQ ID NO 36
<211> LENGTH: 217
<212> TYPE: PRT
<213> ORGANISM: Marburg virus

<400> SEQUENCE: 36

```
Gly Leu Ser Ser Thr Met Pro Pro Thr Pro Ser Pro Gln Pro Ser Thr
 1               5                  10                  15

Pro Gln Gln Gly Gly Asn Asn Thr Asn His Ser Gln Asp Ala Val Thr
            20                  25                  30

Glu Leu Asp Lys Asn Asn Thr Thr Ala Gln Pro Ser Met Pro Pro His
        35                  40                  45

Asn Thr Thr Thr Ile Ser Thr Asn Asn Thr Ser Lys His Asn Phe Ser
    50                  55                  60

Thr Leu Ser Ala Pro Leu Gln Asn Thr Thr Asn Asp Asn Thr Gln Ser
65                  70                  75                  80

Thr Ile Thr Glu Asn Glu Gln Thr Ser Ala Pro Ser Ile Thr Thr Leu
                85                  90                  95

Pro Pro Thr Gly Asn Pro Thr Thr Ala Lys Ser Thr Ser Ser Lys Lys
            100                 105                 110

Gly Pro Ala Thr Thr Ala Pro Asn Thr Thr Asn Glu His Phe Thr Ser
        115                 120                 125

Pro Pro Pro Thr Pro Ser Ser Thr Ala Gln His Leu Val Tyr Phe Arg
    130                 135                 140

Arg Lys Arg Ser Ile Leu Trp Arg Glu Gly Asp Met Phe Pro Phe Leu
145                 150                 155                 160

Asp Gly Leu Ile Asn Ala Pro Ile Asp Phe Asp Pro Val Pro Asn Thr
                165                 170                 175

Lys Thr Ile Phe Asp Glu Ser Ser Ser Gly Ala Ser Ala Glu Glu
            180                 185                 190

Asp Gln His Ala Ser Pro Asn Ile Ser Leu Thr Leu Ser Tyr Phe Pro
        195                 200                 205

Asn Ile Asn Glu Asn Thr Ala Tyr Ser
    210                 215
```